(12) United States Patent
Schmidt et al.

(10) Patent No.: US 12,161,622 B2
(45) Date of Patent: *Dec. 10, 2024

(54) COMPOSITIONS AND METHODS FOR THE TREATMENT OF DEPRESSION

(71) Applicant: Janssen Pharmaceuticals, Inc., Titusville, NJ (US)

(72) Inventors: Mark Schmidt, Antwerp (BE); Vanina Popova, Nijlen (BE); Adam Savitz, Greenwich, CT (US); Rama Melkote, Basking Ridge, NJ (US); Wayne C. Drevets, Rancho Santa Fe, CA (US); Srihari Gopal, Belle Mead, NJ (US); Darrel Pemberton, Oud Turnhout (BE); Chakradhar Lagishetty, King of Prussia, PA (US); Iva Kezic, Antwerp (BE)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 155 days.

This patent is subject to a terminal disclaimer.

(21) Appl. No.: 17/670,123

(22) Filed: Feb. 11, 2022

(65) Prior Publication Data

US 2022/0370409 A1 Nov. 24, 2022

Related U.S. Application Data

(63) Continuation of application No. 17/307,858, filed on May 4, 2021, now Pat. No. 11,266,627.

(51) Int. Cl.
*A61K 31/40* (2006.01)
*A61K 9/00* (2006.01)
*A61P 25/24* (2006.01)

(52) U.S. Cl.
CPC ............ *A61K 31/40* (2013.01); *A61K 9/0056* (2013.01); *A61P 25/24* (2018.01)

(58) Field of Classification Search
CPC ................................ A61K 31/40; A61P 25/24
See application file for complete search history.

(56) References Cited

U.S. PATENT DOCUMENTS

| | | | |
|---|---|---|---|
| 5,457,208 A | 10/1995 | Portoghese et al. | |
| 6,391,873 B1 | 5/2002 | Jenck et al. | |
| 6,528,518 B2 | 3/2003 | Carlezon, Jr. | |
| 7,196,100 B2 | 3/2007 | Benesh et al. | |
| 7,288,543 B2 | 10/2007 | Broughton et al. | |
| 7,378,448 B2 | 5/2008 | Mitch et al. | |
| 7,381,719 B2 | 6/2008 | Blanco-pillado et al. | |
| 7,381,750 B2 | 6/2008 | De et al. | |
| 7,396,943 B2 | 7/2008 | Benesh et al. | |
| 7,399,774 B2 | 7/2008 | Siegel et al. | |
| 7,414,132 B2 | 8/2008 | De La Torre et al. | |
| 7,531,557 B2 | 5/2009 | Mitch | |
| 7,560,463 B2 | 7/2009 | Mitch et al. | |
| 7,709,522 B2 | 5/2010 | Buezo et al. | |
| 8,063,059 B2 | 11/2011 | Hermann | |
| 8,173,695 B2 | 5/2012 | Diaz et al. | |
| 10,676,469 B2 | 6/2020 | Roberts et al. | |
| 11,266,627 B1 * | 3/2022 | Schmidt | A61K 9/4866 |
| 2002/0052365 A1 | 5/2002 | Hanns et al. | |
| 2004/0082573 A1 | 4/2004 | Cook et al. | |
| 2006/0052439 A1 | 3/2006 | Beguin et al. | |
| 2007/0155793 A1 | 7/2007 | Benesh | |
| 2007/0213394 A1 | 9/2007 | Beguin et al. | |
| 2008/0207701 A1 | 8/2008 | Chappell et al. | |
| 2008/0255152 A1 | 10/2008 | Blanco-pillado et al. | |
| 2008/0269296 A1 | 10/2008 | Blanco-pillado et al. | |
| 2009/0023785 A1 | 1/2009 | Pedregal-tercero et al. | |
| 2009/0186873 A1 | 7/2009 | Buezo et al. | |
| 2009/0196824 A1 | 8/2009 | Wasley et al. | |
| 2010/0197669 A1 | 8/2010 | Diaz Buezo et al. | |
| 2013/0303497 A1 | 11/2013 | Hansen et al. | |
| 2015/0005315 A1 | 1/2015 | Carroll et al. | |
| 2016/0310488 A1 | 10/2016 | Morillo et al. | |
| 2018/0072654 A1 | 3/2018 | Schmidhammer et al. | |
| 2018/0148432 A1 | 5/2018 | Kablaoui et al. | |

(Continued)

FOREIGN PATENT DOCUMENTS

| | | |
|---|---|---|
| CN | 114195693 A | 3/2022 |
| WO | 02053533 A2 | 7/2002 |

(Continued)

OTHER PUBLICATIONS

Caira et al., "Crystalline Polymorphism of Organic Compounds", Topics in Current Chemistry, Springer, Berlin, DE, vol. 198, pp. 163-208, Jan. 1, 1998. XP001156954, ISSN: 0340-1022, DOI:10.1007/3-540-69178-2_S (retrieved on Feb. 26, 1999].

European Clinical Trial Register Protocol for EudraCT No. 2019-000695-41, "A Phase 2a Randomized, Double-blind, Placebo-Controlled, Parallel-Group, Multi-center Study Investigating the Efficacy, Safety, Tolerability and Pharmacokinetics of JNJ-67953964 in Subjects with Major Depressive Disorder", pp. 1-7, Entry Date: Apr. 26, 2019.

(Continued)

*Primary Examiner* — Kevin E Weddington
(74) *Attorney, Agent, or Firm* — BakerHostetler

(57) ABSTRACT

The disclosure provides methods for treating major depressive disorder in a human patient having moderate or severe anhedonia. The methods comprise administering to the patient in need thereof an effective amount of aticaprant, or a pharmaceutically acceptable salt thereof. In some embodiments, the patient had an inadequate response to other antidepressant therapy prior to treatment with aticaprant. In other embodiments, the other antidepressant therapy comprised a selective serotonin reuptake inhibitor (SSRI), serotonin-norepinephrine reuptake inhibitor (SNRI), or a combination thereof.

29 Claims, 14 Drawing Sheets

(56) References Cited

U.S. PATENT DOCUMENTS

| | | |
|---|---|---|
| 2018/0169065 A1 | 6/2018 | Kellar et al. |
| 2019/0008806 A1 | 1/2019 | Singh et al. |
| 2019/0023700 A1 | 1/2019 | Guerrero et al. |
| 2019/0117637 A1 | 4/2019 | Frazer et al. |
| 2019/0240293 A1 | 8/2019 | Weinstein et al. |
| 2019/0255036 A1 | 8/2019 | Kariman |
| 2019/0263781 A1 | 8/2019 | Carroll et al. |
| 2019/0298703 A1 | 10/2019 | Bhide et al. |
| 2020/0121236 A1 | 4/2020 | Gao et al. |
| 2021/0024576 A1 | 1/2021 | Aldrich et al. |
| 2021/0047310 A1 | 2/2021 | Roberts et al. |
| 2023/0233525 A1 | 7/2023 | Schmidt et al. |
| 2023/0277499 A1 | 9/2023 | Fernandes et al. |
| 2023/0277500 A1 | 9/2023 | Goyvaerts et al. |

FOREIGN PATENT DOCUMENTS

| | | |
|---|---|---|
| WO | 2004026305 A1 | 4/2004 |
| WO | 2008021849 A2 | 2/2008 |
| WO | 2008021851 A2 | 2/2008 |
| WO | 2008032156 A1 | 3/2008 |
| WO | 2009/094260 | 7/2009 |
| WO | 2015/091833 A1 | 6/2015 |
| WO | 2016/156396 A1 | 10/2016 |
| WO | 2016/191763 A2 | 12/2016 |
| WO | 2017/218518 A1 | 12/2017 |
| WO | 2018/022664 A1 | 2/2018 |
| WO | 2018/022666 A1 | 2/2018 |
| WO | 2018/022668 A2 | 2/2018 |
| WO | 2018/053222 A1 | 3/2018 |
| WO | 2018/096510 A1 | 5/2018 |
| WO | 2018/170492 A1 | 9/2018 |
| WO | 2019/183556 A1 | 9/2019 |
| WO | 2020/086729 A1 | 4/2020 |
| WO | 2022234457 A1 | 11/2022 |

OTHER PUBLICATIONS

European Clinical Trial Register Results for EudraCT No. 2019-000695-41, "A Phase 2a Randomized, Double-blind, Placebo-Controlled, Parallel-Group, Multi-center Study Investigating the Efficacy, Safety, Tolerability and Pharmacokinetics of JNJ-67953964 in Subjects with Major Depressive Disorder", pp. 1-20, Publication Date: May 21, 2021.

International Search Report and Written Opinion received for PCT Application No. PCT/IB2023/052088, Mailed on May 31, 2023, 17 pages.

US Clinical Trial Posting for NCT01913535, "Proof-of-Concept Trial of LY2456302 Augmentation of Antidepressant Therapy in Treatment-Resistant Depression", pp. 1-10, Submission Date: Apr. 7, 2015, Estimated Posting Date: Apr. 9, 2015.

US Clinical Trial Posting for NCT01913535, "Proof-of-Concept Trial of LY2456302 Augmentation of Antidepressant Therapy in Treatment-Resistant Depression", pp. 1-38, Submission Date: May 31, 2017, Posting Date: Jul. 2, 2017.

US Clinical Trial Posting for NCT01913535, "Proof-of-Concept Trial of LY2456302 Augmentation of Antidepressant Therapy in Treatment-Resistant Depression", pp. 1-5, Submission Date: Jul. 30, 2013, Estimated: Posting Date Aug. 1, 2013.

US Clinical Trial Posting for NCT03559192, "A Phase 2a Randomized, Double-blind, Placebo-Controlled, Parallel-Group, Multi-center Study Investigating the Efficacy, Safety, Tolerability and Pharmacokinetics of JNJ-67953964 in Subjects With Major Depressive Disorder", pp. 1-13, Submission Date: Dec. 4, 2018, Posting Date: Dec. 5, 2018.

US Clinical Trial Posting for NCT03559192, "A Phase 2a Randomized, Double-blind, Placebo-Controlled, Parallel-Group, Multi-center Study Investigating the Efficacy, Safety, Tolerability and Pharmacokinetics of JNJ-67953964 in Subjects With Major Depressive Disorder", pp. 1-14, Submission Date: Apr. 22, 2019, Posting Date: Apr. 23, 2019.

US Clinical Trial Posting for NCT03559192, "A Phase 2a Randomized, Double-blind, Placebo-Controlled, Parallel-Group, Multi-center Study Investigating the Efficacy, Safety, Tolerability and Pharmacokinetics of JNJ-67953964 in Subjects With Major Depressive Disorder", pp. 1-4, Submission Date: Jun. 6, 2018, Posting Date: Jun. 18, 2018.

"Co-occurring Alcohol Use Disorder and Schizophrenia", Health, Retrieved from: https://athealth.com/topics/co-occurring-alcohol-use-disorder-and-schizophrenia-2/, 9 pages, 2013.

"Diagnostic and Statistical Manual of Mental Disorders", DSM-IV-TR., Revised 4th Ed., Text Revision, 4 pages, 2000.

"Guidance for Industry—Q3A Impurities in New Drug Substances", U.S. Department of Health and Human Services, ICH, 17 pages, Jun. 2008.

"Referencing Approved Drug Products in ANDA Submissions—Guidance for Industry", U.S. Department of Health and Human Services, Generics, 18 pages, Oct. 2020.

"The International Classification of Diseases, Tenth Revision (ICD-10)", National Centre for Health Statistics, 2 pages.

A-Hakeim H, et al, "In major depression, increased serum dynorphin and kappa opioid receptor levels are positively associated with mu opioid receptor levels and immune activation and are attenuated by nicotine dependence", ResearchGate, XP093024086, 39 pages, Apr. 1, 2019.

Anton et al., "American College of Neuropsychopharmacology", Annual Meeting Abstracts—13, Nashville, TN, ACNP, 12 pages, vol. 13, Issue 3, 2007.

Avis et al., "Pharmaceutical Dosage Forms", Parenteral Medications, vols. 1-2, 9 pages.

Beardsley, et al., "Differential effects of the novel kappa opioid receptor antagonist, JDTic, on reinstatement of cocaine-seeking induced by footshock stressors vs cocaine primes and its antidepressant-like effects in rats", Psychopharmacology, vol. 183, pp. 118-126, 2005.

Berge et al., "Pharmaceutical Salts", Journal of Pharmaceutical Sciences, vol. 66 No. 1, pp. 1-19, Jan. 1977.

Berman et al., "The Efficacy and Safety of Aripiprazole as Adjunctive Therapy in Major Depressive Disorder: A Multicenter, Randomized, Double-Blind, Placebo-Controlled Study", J Clin Psychiatry, vol. 68 Issue 6, pp. 843-853, 2007.

Blendov et al., "Reduced alcohol consumption in mice lacking preprodynorphin", Alcohol, vol. 40 No. 2, 23 pages, Oct. 2006.

Bortolato et al., "Kappa Opioid Receptor Activation Disrupts Prepulse Inhibition of the Acoustic Startle in Rats", Biol. Psychiatry, vol. 57 Issue 12, 6 pages, Jun. 15, 2005.

Bouwknecht et al., "The stress-induced hyperthermia paradigm as a physiological animal model for anxiety: A review of pharmacological and genetic studies in the mouse", Neuroscience and Biobehavioral Reviews, vol. 31 Issue 1, 6 pages, 2007.

Carey et al., "Advanced Organic Chemistry. Part B: Reactions and Synthesis. Fourth Edition", Molecules, vol. 6, 3 pages, 2001.

Carroll et al., "N-Substituted 4β-Methyl-5-(3-hydroxyphenyl)-7α-amidomorphans Are Potent, Selective κ Opioid Receptor Antagonists", J. Med. Chem., vol. 49 No. 5, pp. 1781-1791, 2006.

Cheng Y, et al., "Relationship Between the Inhibition Constant (K1) And the Concentration of Inhibitor which causes 50 per cent Inhibition ((I50) an Enzymatic Reaction", Biochem Pharmacol., vol. 22, pp. 3099-3108, 1973.

Chow, "Bioavailability and Bioequivalence in Drug Development", Wiley interdisciplinary reviews, Computational statistics, vol. 6, pp. 304-312, 2014.

Cornelius et al., "Alcohol and psychiatric comorbidity", Recent Dev. Alcoholism, vol. 16, pp. 361-374, 2003.

DeLapp et al., "Determination of [35S] Guanosine-5'-O-(3-thio) Triphosphate Binding Mediated by Cholinergic Muscarinic Receptors in Membranes from Chinese Hamster Ovary Cells and Rat Striatum Using an Anti-G Protein Scintillation Proximity Assay1", Journal of Pharmacology and Experimental Therapeutics, JPET, vol. 289 No. 2, pp. 946-955, 1999.

Dolle et al., "Nascent Structure-Activity Relationship Study of a Diastereomeric Series of Kappa Opioid Receptor Antagonists Derived from CJ-15,208", Bioorganic & Medicinal Chemistry Letters, vol. 19 Issue 13, 4 pages, Jul. 2009.

(56) References Cited

OTHER PUBLICATIONS

El-Khalili et al., "Extended-release quetiapine fumarate (quetiapine XR) as adjunctive therapy in major depressive disorder (MDD) in patients with an inadequate response to ongoing antidepressant treatment: a multicentre, randomized, double-blind, placebo-controlled study", Internatinal J Neuropsychopharmacol., vol. 13, pp. 917-932, 2010.
Emmerson et al., "Characterization of Opioid Agonist Efficacy in a C6 Glioma Cell Line Expressing the μ Opioid Receptor1", J. Pharm Exp Ther., vol. 278 No. 3, pp. 1121-1127, 1996.
Geyer et al., "Pharmacological studies of prepulse inhibition models of sensorimotor gating deficits in schizophrenia: a decade in review", Psychopharmacology, vol. 156, pp. 117-154, 2001.
Grant et al., "Prevalence and Co-occurrence of Substance Use Disorders and Independent Mood and Anxiety Disorders", Arch Gen Psychiatry, vol. 61, pp. 807-816, Aug. 2004.
Gregg et al., "Reasons for increased substance use in psychosis", Clinical Psychology Review, vol. 27, pp. 494-510, 2007.
International Search Report and Written Opinion received for PCT Application No. PCT/IB2022/054085, mailed on Sep. 9, 2022, 14 pages.
International Search Report and Written Opinion received for PCT Application No. PCT/IB2023/050170, Mailed on Feb. 23, 2023, 15 pages.
International Search Report and Written Opinion received for PCT Application No. PCT/US2009/030811, Mailed on Apr. 8, 2009, 9 pages.
Jones et al., "5'-Guanidinonaltrindole, a highly selective and potent κ-opioid receptor antagonist", European Journal of Pharmacology, vol. 396, Issue 1, 6 pages, May 2000.
Knoll et al., "Anxiolytic-Like Effects of K-Opioid Receptor Antagonists in Models of Unlearned and Learned Fear in Rats", J Phrmacol. Experimental Therapeutics., vol. 323, No. 3, pp. 838-845, 2007.
Kovacs et al., "Decreased Oral Self-Administration of Alcohol in κ-Opioid Receptor Knock-Out Mice", Alcoholism: Clinical and Experimental Research, vol. 29, No. 5, pp. 730-738, May 2005.
Lieberman et al., "Pharmaceutical Dosage Forms: Disperse Systems", vols. 1-2, published by Marcel Dekker Inc., 10 pages, 1990.
Lieberman et al., "Pharmaceutical Dosage Forms: Tablets, Second Edition", Revised and Expanded, vols. 1-3, 9 pages, 1990.
Macrae et al., "Mercury: Visualization and analysis of crystal structures", J. Appl. Cryst., vol. 39 Part 3, 8 pages, Jun. 2006.
Mague, et al., "Antidepressant-Like Effects of κ-Opioid Receptor Antagonists in the Forced Swim Test in Rats," The Journal of Pharmacology and Experimental Therapeutics, vol. 305, No. 1, pp. 323-330, 2003.
Marcus et al., "The Efficacy and Safety of Aripiprazole as Adjunctive Therapy in Major Depressive Disorder, A Second Multicenter, Randomized, Double-Blind, Placebo-Controlled Study", J. Clin. Psychopharmacol, vol. 28 No. 2, pp. 156-165, Apr. 2008.
McCann, "Potential of Buprenorphine/Naltrexone in Treating Polydrug Addiction and Co-occurring Psychiatric Disorders", Clinical Pharmacology & Therapeutics, vol. 83, No. 4, pp. 627-630, Apr. 2008.
McLaughlin et al., "κ Opioid Receptor Antagonism and Prodynorphin Gene Disruption Block Stress-Induced Behavioral Responses", The Journal of Neuroscience, vol. 23, No. 13, pp. 5674-5683, Jul. 2, 2003.
National Institute of Mental Health, "Depression, Bethesda: National Institute of Mental Health Publication No. 02-3561", 25 pages, 2002.
Olivier et al., "Stress-induced hyperthermia and anxiety: pharmacological validation", European Journal of Pharmacology, vol. 463, pp. 117-132, 2003.
Pae et al., "Aripiprazole as Adjunctive Therapy for Patients with Major Depressive Disorder: Overview and Implications of Clinical Trial Data", CNS Drugs, vol. 25 No. 2, pp. 109-127, 2011.
Paulekuhn et al., "Trends in Active Pharmaceutical Ingredient Salt Selection based on Analysis of the Orange Book Database", J. Med. Chem., vol. 50 No. 26, pp. 6665-6672, 2007.
Petit-Demouliere, et al., "Forced swimming test in mice: a review of antidepressant activity", Psychopharmacology, vol. 177, pp. 245-255, 2005.
Portoghese, et al., "Binaltorphimine-Related Bivalent Ligands and Their Kappa Opioid Receptor Antagonist Selectivity", J. Med. Chem., vol. 31 No. 4, 13 pages, 1988.
Roman M, et al: "Novel neuroimmunologic therapeuticsin depression: A clinical perspective on what we know so far", Brain, Behavior and Immunity, Academic Press, San Diego, CA, US, vol. 83, pp. 7-21, XP085943201, Sep. 21, 2019.
Rothman, et al., "An open-label study of a functional opioid κ antagonist in the treatment of opioid dependence", Journal of Substance Abuse Treatment, vol. 18, pp. 277-281, 2000.
Schuckit, "Comorbidity between substance use disorders and psychiatric conditions", Addiction, vol. 101, Suppl, 1, pp. 76-88, 2006.
Shippenberg, et al., "Dynorphin and the pathophysiology of drug addiction", Pharmacology & Therapeutics, vol. 116 No.2, 30 pages, 2007.
Smith et al., "March's Advanced Organic Chemistry, Reactions Mechanisms, and Structure, 5th Edition", Molecules, vol. 6, Wiley Interscience, pp. 10164-10165, 2001.
Stahl et al., "Handbook of Pharmaceutical Salts", International Union of Pure and Applied Chemistry, Index, pp. 1-3, 2002.
Stevens, et al., "Potent and Selective Indolomorphinan Antagonists of the Kappa-Opioid Receptor", J. Med. Chem., vol. 43, pp. 2759-2769, 2000.
Swerdlow, et al., "Neural circuit regulation of prepulse inhibition of startle in the rat: current knowledge and future challenges", Psychopharmacology, vol. 156, pp. 194-215, 2001.
Thase et al., "Adjunctive Brexpiprazole 1 and 3 mg for Patients with Major Depressive Disorder Following Inadequate Response to Antidepressants: A Phase 3, Randomized, Double-Blind Study", J Clinical Psychiatry, vol. 76 No. 9, 17 pages, 2015.
Thase et al.,"Efficacy and Safety of Adjunctive Brexpiprazole 2 mg in Major Depressive Disorder", J Clinical Psychiatry, vol. 76 No. 9, 15 pages, 2015.
Thomas, et al., "Discovery of an Opioid κ Receptor Selective Pure Antagonist from a Library of N-Substituted 4β-Methyl-5-(3-hydroxyphenyl) morphans", J. Med. Chem., vol. 45, pp. 3524-3530, 2002.
Thomas, et al., "Identification of (3R)-7-Hydroxy-N-((1S)-1--2-methylpropy1)-1,2,3,4-tetrahydro-3-isoquinolinecarboxamide as a Novel Potent and Selective Opioid κ Receptor Antagonist", J. Med. Chem., vol. 46 No. 14, pp. 3127-3137, 2003.
Thomas, et al., "Importance of Phenolic Address Groups in Opioid Kappa Receptor Selective Antagonists", J. Med. Chem, vol. 47 No. 4, pp. 1070-1073, 2004.
U.S. Department of Health and Human Services, "National Institutes of Health NIH Publication 06-3879", Rockville, MD, 28 pages, 2006.
Vidal, et al., "Assignment of Absolute Configuration on the Basis of the Conformational Effects Induced by Chiral Derivatizing Agents: The 2-Arylpyrrolidine Case", Organic Letters, vol. 9 No. 21, 6 pages, 2007.
Walker, et al., "Pharmacological Evidence for a Motivational Role of κ-Opioid Systems in Ethanol Dependence", Neuropsychopharmacology, vol. 33, pp. 643-652, 2008.
"Impurities: Guide for Residual Solvents Q3C(R8)", ICH Harmonised Guideline, 50 pages, Apr. 22, 2021.
Borbely et al., "Novel drug developmental strategies for treatment-resistant depression," Br. J. Pharmacol., 2022; 179:1146-1186.
Healey et al., "Pharmaceutical solvates, hydrates and amorphous forms: A special emphasis on cocrystals", Advanced Drug Delivery Reviews, vol. 117, Mar. 22, 2017, pp. 25-46.
Peckham, "Kappa opioid receptor antagonism: Are opioids the answer for treatment resistant depression?," Review of Drugs/Pharmacotherapy, 8(4): 175-183, 2018.
Reed et al., "Kappa Opioid Receptor Antagonists as Potential Therapeutics for Mood and Substance Use Disorders". In: Handbook of Experimental Pharmacology, vol. 271, Springer, Cham., 2020.
Surmont, U.S. Appl. No. 18/179,025, "Pure Forms of Crystalline Aticaprant", filed Mar. 6, 2023.

(56) References Cited

OTHER PUBLICATIONS

Browne, et al., "Targeting opioid dysregulation in depression for the development of novel therapeutics", Pharmacol Ther. Sep. 2019; 201: 51-76.

Custodio-Patsey et al., "Sex differences in kappa opioid receptor inhibition of latent postoperative pain sensitization in dorsal horn", Neuropharmacology, 163, 2020, 107726.

Domi et al., "Preclinical evaluation of the kappa-opioid receptor antagonist CERC-501 as a candidate therapeutic for alcohol use disorders", Neuropsychopharmacology, 2018, 43, 1805-1812.

Fava M, et al., "Double-blind, placebo-controlled, proof-of-concept trial of a kappa-selective opioid receptor antagonist augmentation in treatment-resistant depression", Annals of Clinical Psychiatry: Official Journal of the American Academy of Clinical Psychiatrists. Nov. 1, 2020;32(4):e16-e24.

Jackson et al., "Effects of orally-bioavailable short-acting kappa opioid receptor-selective antagonist LY2456302 on nicotine withdrawal in mice", Neuropharmacology, 2015, 270-274.

Jacobson et al., "Sex differences in the modulation of mouse nest building behavior by Kappa Opioid receptor signaling", Neuropharmacology, 2020, 177, 108254, 9 pages.

Jacobson et al., "The kappa opioid receptor antagonist aticaprant reverses behavioral effects from unpredictable chronic mild stress in male nice", Psychopharmacology, 2020, 237, 3715-3728.

Jones et al., "A randomized, double-blind, placebo-controlled study of the kappa opioid receptor antagonist, CERC-501, in a human laboratory model of smoking behavior", Addiction Biology, Jun. 2019, e12799; 9 pages.

Krystal et al., "A randomized proof-of-mechanism trail applying the 'fast-fail' approach to evaluating K-opioid antagonism as a treatment for anhedonia", Nature Medicine, May 2020, vol. 26, 760-768.

Krystal, et al., ACNP 58th Annual Meeting: Panels, Mini-Panels and Study Groups, Neuropsychopharmacology, (2019) 44:1-77.

Li et al., "A Novel 18F-labeled kappa opioid receptor antagonist as PET radiotracer: Synthesis and in vivo Evaluation", The Journal of Nuclear Medicine, May 2016, 57 (supplement 2) 159, 3 pages.

Li et al., "Development and In Vivo Evaluation of a K-Opioid Receptor Agonist as a PET Radiotracer with Superior Imaging Characteristics", The Journal of Nuclear Medicine, Jul. 2019, vol. 60, No. 7, 1023-1030.

Li et al., "Novel 18F-Labeled κ-Opioid Receptor Antagonist as PET Radiotracer: Synthes and In Vivo Evaluation of 18F-LY2459989 in Nonhuman Primates", The Journal of Nuclear Medicine, Jan. 2018, vol. 69, No. 1, 140-146.

Pizzagalli, et al. "Selective kappa-opioid antagonism ameliorates anhedonic behavior: evidence from the Fast-fail Trial in Mood and Anxiety Spectrum Disorders (FAST-MAS)," Neuropsychopharmacol. 45, 1656-1663 (2020).

Reed et al., "Repeated Administration of Opra Kappa (LY2456302), a Novel Short-Acting, Selective KOP-r Antagonist, in Persons with and without Cocaine Dependence", Neuropsychopharmacology, 2018, No. 43, 739-750.

Rorick-Kehn et al., "Determining Pharmacological Selectivity of the Kappa Opioid Receptor Antagonist LY2456302 Using Pupillometry as a Translational Biomarker in Rat and Human", International Journal of Neuropsychopharmacology, 2015, 1-11.

Rorick-Kehn et al., "LY2456302 is a novel, potent, orally-bioavailable small molecule kappa-selective antagonist with activity in animal models predictive of efficacy in mood and addictive disorders", Neuropharmacology, 2014, 77, 131-144.

Undurraga et al., "Randomized, Placebo-Controlled Trials of Antidepressants for Acute Major Depression: Thirty-Year Meta-Analytic Review", Neuropsychopharmacology, vol. 37, No. 4, pp. 851-864 (2012).

Urbano et al., "Antagonists of the kappa opioid receptor", Bioorganic & Medicinal Chemistry Letters, 2014, 24, 2021-2032.

Williams, et al., "Acute inhibition of kappa opioid receptors before stress blocks depression like behaviors in California mice", Progress in Neuropsychopharmacology & Biological Psychiatry, 86 (2018) 166-174.

Zheng et al., "Synthesis and Evaluation of 11C-LY2795050 as a κ-Opioid Receptor Antagonist Radiotracer for PET Imaging", The Journal Nuclear Medicine, Mar. 2013, vol. 54, No. 3, 455-4633.

* cited by examiner

COMPOSITIONS AND METHODS FOR THE TREATMENT OF DEPRESSION

CROSS REFERENCE TO RELATED APPLICATIONS

This application is a continuation of U.S. patent application Ser. No. 17/307,858, filed May 4, 2021, the entire contents of which are incorporated herein by reference.

TECHNICAL FIELD

The present disclosure relates to methods for treating depression using aticaprant.

BACKGROUND

Kappa opioid receptors (KOR) and their native ligand dynorphin are localized in areas of the brain that effect reward and stress and may play a key role in mood, stress, and addictive disorders. Chronic stress, substance abuse, and acute withdrawal lead to increased dynorphin expression, activating KORs and subsequent downstream signaling pathways to inhibit mesolimbic dopamine surge, contributing to negative affective states. The behavioral pharmacology of KOR antagonism has been tested in animal models of anhedonia, depression, and anxiety and found to have meaningful effects that may translate to therapeutic benefit in humans. KOR antagonists may be effective for the treatment of patients with mood disorders, perhaps by modulating the negative affective state associated with stress response.

Anhedonia is one of the core symptoms of depression. At least mild symptoms of anhedonia are present in about 90% of patients suffering from major depressive disorder (MDD). Only about 50% of patients with MDD show a meaningful response (>50% improvement to a first line antidepressant treatment), leaving many patients with substantial persistent impairment. Therapeutic strategies such as switching antidepressants and using adjuvant drug treatments can improve response, however almost 40% of patients remain symptomatic and fail to achieve full remission.

What is needed are treatments for patients having depression and anhedonia.

SUMMARY

In some aspects, the present disclosure is directed to methods for treating major depressive disorder in a human patient having moderate or severe anhedonia, comprising administering to the patient in need thereof an effective amount of aticaprant, or a pharmaceutically acceptable salt thereof. In certain embodiments, the patient has had an inadequate response to other antidepressant therapy prior to treatment with aticaprant, including, for example, an inadequate response to a selective serotonin reuptake inhibitor (SSRI), serotonin-norepinephrine reuptake inhibitor (SNRI), or a combination thereof.

In other aspects, the methods comprise adjunctive treatment with one or more antidepressants. The one or more antidepressants can include, for example, a selective serotonin reuptake inhibitor (SSRI), serotonin-norepinephrine reuptake inhibitor (SNRI), or a combination thereof.

In further aspects, the disclosure relates to aticaprant, or a pharmaceutically acceptable salt thereof, for use in a method of treating major depressive disorder in a human patient having moderate or severe anhedonia, in particular, comprising administering to the patient in need thereof an effective amount of aticaprant, or a pharmaceutically acceptable salt thereof.

In yet other aspects, the disclosure also relates to aticaprant, or a pharmaceutically acceptable salt thereof, for use in the treatment of major depressive disorder in a human patient having moderate or severe anhedonia, in particular, comprising administration of an effective amount of aticaprant, or a pharmaceutically acceptable salt thereof.

In still further aspects, the disclosure also relates to the use of aticaprant, or a pharmaceutically acceptable salt thereof, in the manufacture of a medicament for the treatment of major depressive disorder in a human patient having moderate or severe anhedonia, in particular, wherein the treatment comprises administration of an effective amount of aticaprant, or a pharmaceutically acceptable salt thereof.

In other aspects, the disclosure further relates to a package or pharmaceutical product comprising aticaprant, or a pharmaceutically acceptable salt thereof, together with instructions for the treatment of major depressive disorder in a human patient having moderate or severe anhedonia, in particular, wherein the treatment comprises administration of an effective amount of aticaprant, or a pharmaceutically acceptable salt thereof.

DETAILED DESCRIPTION OF ILLUSTRATIVE EMBODIMENTS

Figure 1:
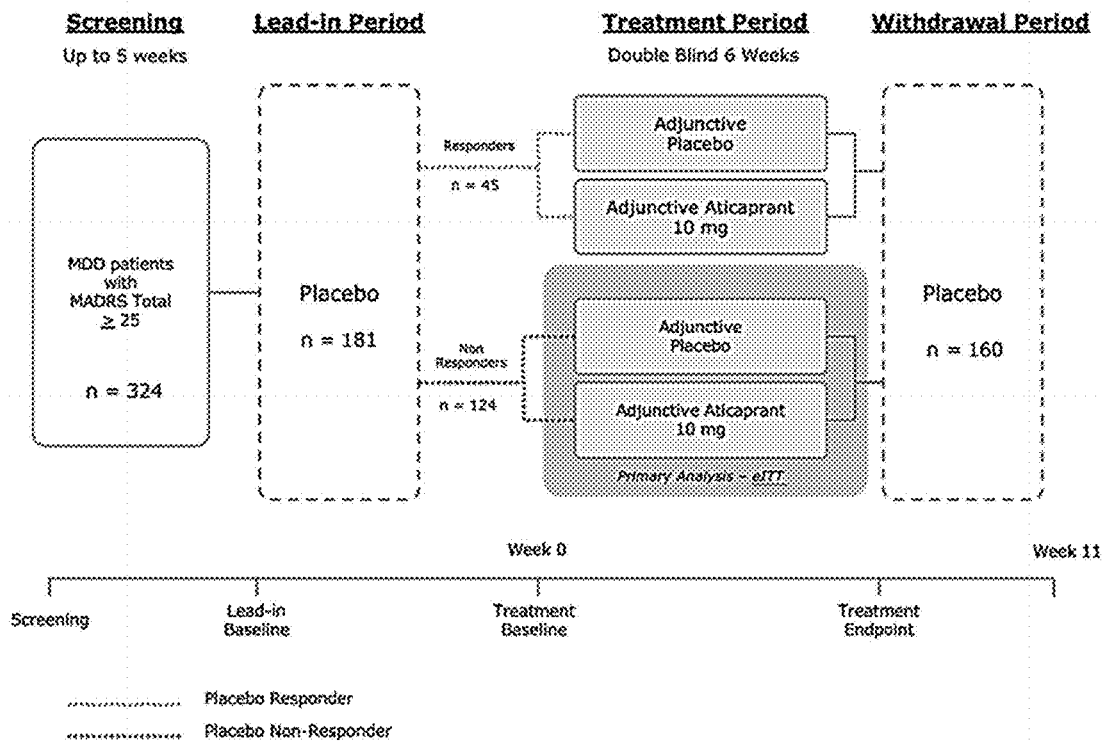
FIG. 1 is the trial design of Example 1.

All individual features (e.g., particular embodiments or specific preferred features) mentioned herein may be taken in isolation or in combination with any other feature (including particular embodiment or preferred feature) mentioned herein; hence, preferred features may be taken in conjunction with other preferred features, or independently of them (and likewise with particular embodiments).

In one aspect of the present invention, methods are provided for treating patients having a more severe type of depression, i.e., major depressive disorder, and experiencing moderate to severe anhedonia. Because MDD alone is difficult to treat, treatment patients having anhedonia are even more problematic since their ability to gauge pleasure is impaired. Thus, such patients often receive inadequate treatment due to ineffective medications, repeated and unnecessary medical appointments, lack of patient compliance, overall patient frustration, among others. Further, antidepressants are known to have a variety of side effects such as weight gain, metabolic side effects, extrapyramidal symptoms, akathisia, cognitive impairment, among others. Thus, patients may choose to refrain from or stop taking antidepressants to avoid or prevent any side-effects.

The methods described herein are effective in managing the patient's depression and anhedonia using aticaprant. Desirably, the methods successfully permit the patient to manage their depression while simultaneously reducing anhedonia. In particular embodiments, the patients treated according to the described methods have moderate to severe anhedonia. The term "anhedonia" as used herein refers to the lack of or decreased ability to experience pleasure in daily activities. The term anhedonia includes loss of pleasure in sensory experiences (i.e., touch, taste, smell), as well as social interactions. In some embodiments, anhedonia and depressed mood are diagnostic criteria for a major depressive episode as part of MDD. Anhedonia also describes deficits in one or more components of reward-related behavior, also known as the pleasure cycle, such as wanting, liking, and learning. The pleasure cycle can be divided into three phases: the appetitive phase (dominated by wanting), the consummatory phase (dominated by liking), and the satiety phase (dominated by learning). The appetitive phase is characterized by the initial energy expenditure to attain a reward; the consummatory phase is enjoyment of the reward; and the satiety phase is characterized by learning and feedback integration.

To assess a potential effect on anhedonia, an anhedonia scale may be used. For example, the Snaith-Hamilton Pleasure Scale (SHAPS) analysis is a validated scale for the measurement of anhedonia. The SHAPS is a subject completed scale in which subjects score whether or not they experience pleasure in performing a list of activities or experiences. The SHAPS is a self-reported 14-item instrument, developed for the assessment of hedonic capacity. Subjects score whether they experience pleasure in performing a list of activities or experiences. Subjects can rate the answers as 1-4 where 1 indicates "Definitely agree", 2 indicates "Agree", 3 indicates "Disagree" and 4 indicates "Definitely disagree". The subject's item responses are summed to provide a total score ranging from 14 to 56. A higher total SHAPS score indicates higher levels of current anhedonia. Physician/clinical judgment can be used to assess anhedonia separately or in conjunction with an anhedonia scale.

In some embodiments, the patient has moderate anhedonia. In other embodiments, the patient has severe anhedonia. An assessment of moderate or severe anhedonia is typically determined physician/clinical judgment and/or by one or more tests that provide insight into whether a patient has anhedonia. For example, the severity of the anhedonia may be determined using the SHAPS method. In some embodiments, a patient with moderate or severe anhedonia is considered to have a high level of anhedonia. For example, a patient with a SHAPS score of 38 or greater is considered to have moderate to severe anhedonia that can be considered a high level of anhedonia. In some embodiments, a high level of anhedonia is reflected by a SHAPS score of at least about 40, about 42, about 44, about 46, about 48, about 50, about 52, about 54, about 56, about 58, or higher. A patient with mild or no anhedonia would be considered to have a low level of anhedonia that is assessed by physician/clinical judgment and/or one or more tests. For example, a patient with a SHAPS score of less than 38 is considered to have low anhedonia. In certain embodiments, a patient with mild anhedonia may have a SHAPS score of 20 to less than 38, for example, a SHAPS score of 20 to about 36, about 22 to about 36, about 24 to about 36, about 26 to about 36, about 26 to about 34, about 26 to about 32, about 26 to about 30, about 26 to about 28, about 28 to about 36, about 28 to about 36, about 30, to about 36, about 32 to about 36, about 34 to about 36, about 20 to about 34, about 22 to about 34, about 24 to about 34, about 26 to about 32, about 26 to about 30, about 26 to about 28, about 28 to about 36, about 28 to about 34, about 28 to about 32, about 28 to about 30, about 30 to about 36, about 30 to about 34, about 30 to about 32, about 32 to about 36, about 32 to about 34, or about 34 to about 36. Typically, a SHAPS score of less than 20 can be considered to correspond to normal hedonic functioning, and for purposes of this disclosure, would fall into the low category of anhedonia, e.g., a SHAPS score of less than 38.

In some embodiments, the patient's anhedonia is reduced from a high level of anhedonia to a low level of anhedonia. In yet other embodiments, the patient's anhedonia is reduced by at least about 40%, as measured by the change from baseline in total score in an anhedonia scale following treatment with aticaprant. In yet other embodiments, the patient's anhedonia is reduced by at least about 40%, about 50%, about 60%, about 70%, about 80%, about 90%, or about 95%, as measured by the change from baseline in total score in an anhedonia scale following treatment with aticaprant. In still further embodiments, In yet other embodiments, the patient's anhedonia is reduced by about 40 to about 90%, about 50 to about 90%, about 60 to about 90%, about 70 to about 90%, about 80 to about 90%, about 40 to about 80%, about 50 to about 80%, about 60 to about 80%, about 70 to about 80%, about 40 to about 70%, about 50 to about 70%, about 60 to about 70%, about 40 to about 60%, about 50 to about 60%, or about 50 to about 60%, as measured by the change from baseline in total score in an anhedonia scale following treatment with aticaprant. In other embodiments, the patient's anhedonia is ameliorated, i.e., reduced by 100%, as measured by the change from baseline in total score in an anhedonia scale following treatment with aticaprant.

Reduction of anhedonia after initiating treatment with aticaprant may be measured relative to the anhedonia of the patient as measured before treatment with aticaprant, i.e., a baseline anhedonia measurement. In doing so, the treating clinician is able to calculate the change of anhedonia from the baseline to the real time anhedonia measurement at any point after treatment with aticaprant. Thus, standard methods for measuring anhedonia may be used, such as an anhedonia scale, e.g., SHAPS.

Desirably, a baseline anhedonia measurement is obtained no more than about 1 week before initiating treatment with aticaprant. In some embodiments, a baseline anhedonia measurement is obtained about 7 days, about 6 days, about 5 days, about 4 days, about 3 days, about 2 days, or about 1 day before treatment with aticaprant. In further embodiments, a baseline anhedonia measurement is obtained about 24 hours, about 18 hours, about 12 hours, about 8 hours, about 4 hours, about 2 hours, about 1 hours, about 30 minutes, or about 15 minutes before initiating treatment with aticaprant.

The patient's change of anhedonia will depend on several factors including, without limitation, anhedonia severity, patient's sensitivity to aticaprant, other pharmaceutical agents being administered, among others. In some embodiments, the patient's anhedonia is reduced after about 3 weeks of aticaprant treatment. In other embodiments, the patient's anhedonia is reduced after about 3 weeks of aticaprant treatment. In further embodiments, the patient's anhedonia is reduced after about 3 weeks to about 6 weeks, and, in certain embodiments, through week 6, of aticaprant treatment. In certain embodiments, the patient's anhedonia is reduced by at least about 40%, as measured by the change from baseline in total score in an anhedonia scale following about 6 weeks of the treatment with aticaprant. In further embodiments, the anhedonia of the patient is reduced within about 3 weeks, and in some embodiments within about 3 weeks to about 6 weeks, as measured by the change from baseline in total score in an anhedonia scale and/or by physician/clinical judgement.

The methods described herein were found to not only improve the patient's depression and anhedonia symptoms, but resulted in fewer antidepressant side effects. Doing so resulted in less absenteeism (i.e., more visits or interactions with physicians), greater cognitive functioning, improvements in health-related quality of life, more interest and engagement in everyday activities, improvement in family and inter-personal relationships, ability to function in the workplace, fewer hospitalizations, among others.

As used herein, unless otherwise noted, the terms "subject" and "patient" refer to a human, who has been the object of treatment, observation or experiment. Preferably, the patient has experienced and/or exhibited at least one symptom of the disease or disorder to be treated and/or prevented. In some embodiments, the patient is an adult. As used herein, the term "adult" as used herein refers to a human that is about 18 years of age or older. In certain aspects, the patient is an elderly adult, i.e., greater than or equal to 65 years of age.

As used herein, unless otherwise noted, the terms "treating", "treatment" and the like, shall include the management and care of a subject or patient (preferably mammal, more preferably human) for the purpose of combating a disease, condition, or disorder and includes the administration of a compound described herein to prevent the onset of the symptoms or complications, alleviate one or more of the symptoms or complications, or eliminate the disease, condition, or disorder.

As used herein, the term "depression" (also referred to as depressive disorder) includes major depressive disorder, persistent depressive disorder, seasonal affective disorder, postpartum depression, premenstrual dysphoric disorder, situational depression, anhedonia, melancholic, mid-life depression, late-life depression, bipolar depression, depression due to identifiable stressors, treatment resistant depression, or combinations thereof. In certain embodiments, the depression is major depressive disorder. In other embodiments, the major depressive disorder is with melancholic features or anxious distress. In further embodiments, the depression is treatment-resistant depression. In other embodiments, the depression is major depressive disorder with suicidal ideation.

As known in the art, a patient is considered to have major depressive disorder if exhibiting five or more symptoms during the same two week period that are a change from previous functioning; depressed mood and/or loss of interest/pleasure must be present; excluding symptoms clearly attributable to another medical condition. See, e.g., Table A.

TABLE A

1. Depressed mood: Most of the day, nearly every day; may be subjective (e.g., feels sad, empty, hopeless) or observed by others (e.g., appears tearful); in children and adolescents, can be irritable mood TABLE A-continued 2. Loss of interest/pleasure: Markedly diminished interest/pleasure in all (or almost all) activities most of the day, nearly every day; may be subjective or observed by others
3. Weight loss or gain: Significant weight loss (without dieting) or gain (change of >5% body weight in a month), or decrease or increase in appetite nearly every day; in children, may be failure to gain weight as expected
4. Insomnia or hypersomnia: Nearly every day
5. Psychomotor agitation or retardation: Nearly every day and observable by others (not merely subjectively restless or slow)
6. Fatigue: Or loss of energy, nearly every day
7. Feeling worthless or excessive/inappropriate guilt: Nearly every day; guilt may be delusional; not merely self-reproach or guilt about being sick
8. Decreased concentration: Nearly every day; may be indecisiveness; may be subjective or observed by others
9. Thoughts of death/suicide" Recurrent thoughts of death (not just fear of dying), recurrent suicidal ideation without specific plan, or suicide attempt, or a specific plan for suicide In some embodiments, to be diagnosed with MDD, the following criteria also are met:
1. Symptoms cause clinically significant distress or impairment in social, occupational, or other important areas of functioning
2. Episode not attributable to physiological effects of a substance or another medical condition
3. Episode not better explained by schizoaffective disorder, schizophrenia, schizophreniform disorder, delusional disorder, or other specified and unspecified schizophrenia spectrum and other psychotic disorders
4. No history of manic or hypomanic episode Major depressive disorder may be categorized as mild, moderate, or severe. In some embodiments, the MDD is mild. In other embodiments, the MDD is moderate. In further embodiments, the MDD is severe. As used herein, "mild MDD" applies to a patient having few, if any, symptoms in excess of those required to make the diagnosis, the intensity of the symptoms is distressing but manageable, and the symptoms result in minor impairment in social or occupational functioning. The mild MDD may be a single episode (ICD-10 F32.0) or a recurrent episode (ICD-10 F33.0). "Moderate MDD" applies to a patient having a number of symptoms, intensity of symptoms, and/or functional impairment are between those specified for "mild" and "severe." The moderate MDD may be a single episode (ICD-10 F32.1) or a recurrent episode (ICD-10 F33.1). "Severe MDD" applies to a patient where the number of symptoms is substantially in excess of that required to make the diagnosis, the intensity of symptoms is seriously distressing and unmanageable, and the symptoms markedly interfere with social and occupational functioning, and urgent symptom control is necessary. In some embodiments, the severe MDD may be a single episode (ICD-10 F32.2) or a recurrent episode (ICD-10 F33.2). In other embodiments, MDD is classified according to the DSM-5 definition of Table B.

TABLE B

DSM-5 Criteria for MDD

| | |
|---|---|
| 1. Depressed Mood | At least 1 |
| 2. Loss of interest/pleasure (anhedonia) | |
| 1. Weight loss or gain | At least 5 |
| 2. Sleep problems | |
| 3. Psychomotor agitation or retardation | |
| 4. Guilt or worthlessness | |
| 5. Decreased concentration | |
| 6. Suicidality | |

TABLE B-continued

DSM-5 Criteria for MDD

| | |
|---|---|
| 7. Fatigue | |
| 1. Symptoms cause significant distress or impairment | Must have all 4 |
| 2. Not attributable to medical condition | |
| 3. Exclude schizophrenia disorders | |
| 4. No hx of mania or hypomania | |

Several scales are known in the art that may be utilized to diagnose or monitor patients with MDD. Examples of these scales include, without limitation, the Montgomery-Åsberg Depression Rating Scale (MADRS), Clinical Global Impression-Severity (CGI-S) scale, Symptoms of Major Depressive Disorder Scale (SMDDS), Self-Assessment of Treatment Experience (SATE) scale, and Massachusetts General Hospital (MGH) Antidepressant Treatment Response Questionnaire (ATRQ), i.e., MGH-ATRQ.

In some embodiments, MADRS is utilized to diagnose and/or monitor the patient. MADRS is a 10-item rating scale that is used in antidepressant studies. It is clinician-administered and designed to be used in subjects with MDD to measure the overall severity of depressive symptoms. The MADRS scale is validated, reliable, and acceptable to regulatory health authorities as a primary scale to determine efficacy in major depression. In some embodiments, MADRS is administered using the Structured Interview Guide for the MADRS (SIGMA). The scale consists of 10 items, each of which is scored from 0 (item not present or normal) to 6 (severe or continuous presence of the symptoms), summed for a total possible score of 60. Higher scores represent a more severe condition. The MADRS evaluates apparent sadness, reported sadness, inner tension, sleep appetite, concentration, lassitude, inability to feel (interest level), pessimistic thoughts, and suicidal thoughts.

In other embodiments, CGI-S is utilized to diagnose and/or monitor the patient's depression. CGI-S is a scale that rates the severity of the subject's illness at the time of assessment, relative to the clinician's past experience with subjects who have the same diagnosis and improvement with treatment. CGI-S provides an overall clinician-determined summary measure of severity of subject's illness that considers all available information, including knowledge of subject's history, psychosocial circumstances, symptoms, behavior, and impact of symptoms on subject's ability to function. CGI-S evaluates severity of psychopathology on scale of 0 to 7. Subject is assessed on severity of mental illness at time of rating according to: 0=not assessed; 1=normal (not at all ill); 2=borderline mentally ill; 3=mildly ill; 4=moderately ill; 5=markedly ill; 6=severely ill; 7=among most extremely ill patients.

In further embodiments, SMDDS is utilized to diagnose and/or monitor the patient's depression. SMDDS is a subjective rating of the patient. The SMDDS is a 16-item PRO measure. Each item is rated by the subject according to a 5-point Likert scale. Subjects respond to each question using a rating scale between 0 ("Not at all" or "Never") to 4 ("Extremely" or "Always"). The total score ranges from 0 to 60. The SMDDS uses a 7-day recall period and verbal rating scales. Higher score indicates more severe depressive symptomatology.

In yet other embodiments, SATE is utilized to diagnose and/or monitor the patient's depression. SATE is a one to three questionnaire administered when the subject is unable to complete other evaluations, i.e., away from the clinical setting such as at home. SATE is useful to evaluate improvement or deterioration of depressive symptoms of the subjects over a short period of time. For rating overall depression, subject selected one option out of Improved, not changed or got worse; for depression improvement, subject selected one option out of slightly improved, much improved, very much improved and for depression worsen subject selected slightly worse, much worse, very much worse. See, Table C.

TABLE C

SATE Questionnaire

Question 1: Since starting this study medication, overall would you say your depression is:
  Improved
  Got worse
  Not changed
If the subject selects answer 1 (Improved), following question is asked:
Question 2: How much did your depression improve?
  Slightly improved
  Much improved
  Very much improved
If the subject selects answer 3 (Got worse), following question is asked:
Question 3: How much did your depression worsen?
  Slightly worse
  Much worse
  Very much worse The MGH-ATRQ is a self-rated scale used to determine treatment resistance in patient's having MDD. This questionnaire examines the antidepressant treatment history, using specific anchor points to define the adequacy of both dose and duration of each antidepressant trial, and the degree of symptomatic improvement. The MGH-ATRQ permits determining treatment resistance in depression and is known to those skilled in the art.

In certain embodiments, the patient had an inadequate response to other antidepressant therapy (i.e., antidepressant medication or treatment used to treat depression other than aticaprant). "Inadequate response" as used herein refers to a patient experiencing a less than about 50% reduction in depressive symptom severity from the start of initiating treatment. Typically, the inadequate response is during a current/active episode of the depression. In some embodiments, an inadequate response refers to a patient experiencing about 26 to less than about 50% reduction in depressive symptom severity from the start of initiating treatment. In other embodiments, an inadequate response refers to a patient experiencing about 26 to about 49, about 26 to about 45, about 26 to about 40, about 26 to about 35, about 26 to about 30, about 30 to about 49, about 30 to about 45, about 30 to about 40, about 30 to about 35, about 35 to about 49, about 35 to about 45, about 35 to about 40, about 40 to about 49, or about 40 to about 45% reduction in depressive symptom severity from the start of initiating treatment. A patient's response may be measured by one or more scales described herein and/or by physician/clinical judgment. In some embodiments, an inadequate response is measured by MGH-ATRQ, MADRS, or SHAPS. In further embodiments, an inadequate response is measured by MGH-ATRQ.

To the extent a patient is said to have a partial response to treatment, this refers to some minor to moderate symptomatic improvement since the initiation of treatment, but some of the initial symptoms are still present and troubling to the patient and these persistent symptoms still affect behavior and function. For instance, the patient's motivation, productivity, and interest in his or her usual activities may still be impaired.

Antidepressant therapy refers to any pharmaceutical agent which can be used to treat depression. Suitable examples include, without limitation, mono-amine oxidase inhibitors, tricyclics, tetracyclics, non-cyclics, triazolopyridines, selective serotonin reuptake inhibitors (SSRI), serotonin receptor antagonists, serotonin noradrenergic reuptake inhibitors (SNRI), noradrenergic and specific serotonergic agents, noradrenaline reuptake inhibitors, or antipsychotics (typical or atypical antipsychotics). Examples of mono-amine oxidase inhibitors include phenelzine, tranylcypromine, moclobemide, and the like. Examples of tricyclics include imipramine, amitriptyline, desipramine, nortriptyline, doxepin, protriptyline, trimipramine, clomipramine, amoxapine, and the like. Examples of tetracyclics includes maprotiline, and the like. Examples of non-cyclics include nomifensine, and the like. Examples of triazolopyridines include trazodone, and the like. Examples of SSRIs include fluoxetine, sertraline, paroxetine, citalopram, citalopram, escitalopram, fluvoxamine, and the like. Examples of serotonin receptor antagonists include nefazadone, and the like. Examples of SNRIs include venlafaxine, milnacipran, desvenlafaxine, duloxetine, levomilnacipran and the like. Examples of noradrenergic and specific serotonergic agents include mirtazapine, and the like. Examples of noradrenaline reuptake inhibitors include reboxetine, edivoxetine and the like. Examples of typical antipsychotics include phenothiazines (e.g., chlorpromazine, thioridazine, fluphenazine, perphenazine, trifluoperazine, levomepromazin), thioxanthenes (e.g., thiothixene, flupentixol), butyrophenones (e.g., haloperidol), dibenzoxazepines (e.g., loxapine), dihydroindolones (e.g., molindone), substituted benzamides (e.g., sulpride, amisulpride), and the like. Examples of atypical antipsychotics include paliperidone, clozapine, risperidone, olanzapine, quetiapine, zotepine, ziprasidone, iloperidone, perospirone, blonanserin, sertindole, ORG-5222, sonepiprazole, aripiprazole, nemonapride, SR-31742, CX-516, SC-111, NE-100, divalproate (mood stabilizer) and the like. In further embodiments, the antidepressant therapy includes natural products such as Kava-Kava, St. John's Wort, and the like or dietary supplements such as s-adenosylmethionine, and the like. In yet other embodiments, the antidepressant therapy includes neuropeptides such as thyrotropin-releasing hormone and the like or compounds targeting neuropeptide receptors such as neurokinin receptor antagonists and the like. In still further embodiments, the antidepressant therapy is a hormone such as triiodothyronine, and the like. In other embodiments, the antidepressant therapy is SSRI, SNRI, or a combination thereof. Preferably, the antidepressant is a SSRI that is escitalopram, sertraline, paroxetine, fluoxetine or citalopram. In other embodiments, the antidepressant is a SNRT that is venlafaxine, duloxetine, vortioxeine or desvenlafaxine. There are also non-pharmacologic treatments, such as psychotherapy and transcranial magnetic stimulation, that are also available and options for adjunctive therapy.

Therapeutically effective amounts/dosage levels and dosage regimens for the other antidepressant therapy may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http:///www.pdrel.com) or other sources.

In some embodiments, other antidepressant therapy may include one antidepressant medication. In other embodiments, other antidepressant therapy includes two or more antidepressant medications. In further embodiments, other antidepressant therapy includes two antidepressant medications. In yet other embodiments, other antidepressant therapy includes three antidepressant medications. The attending physician would be able to select suitable antidepressant therapies for use as described herein.

In certain embodiments, the patient was receiving treatment with other antidepressant therapy prior to receiving aticaprant. In some embodiments, the patient was receiving treatment with other antidepressant therapy that comprised a SSRI, SNRI, or a combination thereof. In other embodiments, the patient stopped treatment with other antidepressant therapy before initiating treatment with aticaprant.

Also encompassed by the methods described herein include adjunctive treatment with an effective amount of one or more antidepressants. As used herein, the term "adjunctive treatment" and "adjunctive therapy" shall mean treatment of a patient in need thereof by administering aticaprant in combination with one or more antidepressant(s), wherein aticaprant and the antidepressant(s) are administered by any suitable means, simultaneously, sequentially, separately, or in a single pharmaceutical formulation.

In some aspects, aticaprant is administered adjunctively with other antidepressant(s) currently being administered to the patient, including current antidepressant(s) to which the patient had an inadequate response. In other embodiments, aticaprant is administered adjunctively with an antidepressant(s) not previously administered to the patient. In still other embodiments, aticaprant is administered in a regimen with an antidepressant(s) previously administered to the patient.

Where aticaprant and other antidepressant(s) are administered in separate dosage forms, the number of dosages administered per day for each active compound may be the same or different and more typically different. The antidepressant may be dosed as prescribed by the attending physician and/or by its label and aticaprant is dosed as described herein. Typically, a patient is under concurrent treatment with both an antidepressant and aticaprant, where both are administered by their prescribed dosing regimens. The aticaprant and antidepressant(s) may be administered according to simultaneous or alternating regimens, at the same or different times during the course of the therapy, concurrently in divided or single forms.

Aticaprant and the antidepressant(s) may be administered via the same or different routes of administration. Examples of suitable methods of administration include, but are not limited to, oral, intravenous (iv), intranasal (in) intramuscular (im), subcutaneous (sc), transdermal, buccal, or rectal. In some embodiments, aticaprant is administered orally.

Treatment with aticaprant as described herein has several advantages over the treatments in the art. In some embodiments, the patient does not experience many of the side effects that are associated with other antidepressants, i.e., antidepressants other than aticaprant. In certain aspects, the patient does not experience weight gain during the treatment with aticaprant. As used herein, the term "weight gain" refers to an increase in the weight of patient, relative to the weight of the patient before taking aticaprant or the weight of the patient that is assessed at the time of the initial administration of the aticaprant. In certain embodiments, the patient may actually see a decrease in overall weight, relative to the weight of the patient before taking aticaprant. In further embodiments, the patient's weight is stable, i.e., does not increase or decrease. In certain embodiments, the patient does not experience a clinically relevant weight gain which is characterized as a weight increase of ≥7%.

This is contrary to many other antidepressants where weight gain, including clinically relevant weight gain, is a common, but unfortunate, side-effect.

In further aspects, the patient does not experience a decrease in sexual functioning during the treatment with aticaprant. As used herein, the term "decrease in sexual functioning" refers to reducing or lessening of one or more components of the human sex drive, i.e., sexual functioning. In some embodiments, the sexual functioning comprises one or more of sexual drive, sexual arousal, vaginal lubrication, erection, orgasm achievement, or orgasm satisfaction. In other embodiments, the sexual functioning comprises sexual drive. In further embodiments, the sexual functioning comprises vaginal lubrication satisfaction. In further embodiments, the sexual functioning comprises orgasm achievement. In yet other embodiments, the sexual functioning comprises orgasm satisfaction. Desirably, the patient's sexual functioning is assessed at the time of initial administration of the aticaprant. Thus, the patient's sexual functioning while taking aticaprant can be compared to the patient's sexual functioning before administration of aticaprant. Sexual functioning may be assessed by using standard scales and techniques such as the Arizona Sexual Experience Scale (ASEX). The ASEX is used to investigate whether aticaprant has a further positive or negative effect on sexual function. The ASEX is 5 item rating scale administered to patients that quantifies sexual drive, sexual arousal, vaginal lubrication or penile erection, ability to reach orgasm and satisfaction. Scores range from 5 to 30, and two different versions of the scale are available (males and females).

Other scales may be utilized to determine the effectiveness of the methods used herein to treat the patient. Examples include the Cognitive and Physical Functioning Questionnaire (CPFQ), Karolinska Sleepiness Scale (KSS), and Temporal Experience of Pleasure Scale (TEPS). The CPFQ is a brief self-report scale that provides additional information regarding the impact of adjunctive treatment on aspects of cognitive and executive function including attention, memory and mental acuity. Subjects with MDD are often reported to have difficulties with functioning in this area. The KSS is a subject-reported assessment used to rate sleepiness on a scale of 1 to 9, ranging from "extremely alert" (1) to "very sleepy, great effort to keep awake, fighting sleep" (9). The TEPS includes 18 items, 2 subscales designed to distinguish between anticipatory and consummatory pleasure.

As used herein, unless otherwise noted, the term "aticaprant" refers to 3-fluoro-4-4-2-(3,5-dimethylphenyl)pyrrolidin-1-yl-methylphenoxybenzamide, i.e., the following compound:

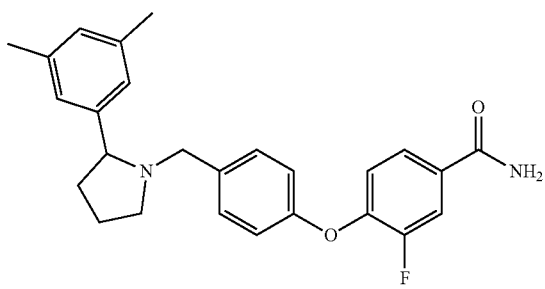 [SMILES: Cc1cc(C)cc(C2CCCN2Cc2ccc(Oc3ccc(C(N)=O)cc3F)cc2)c1]

and is also known as JNJ-67953964, CERC-501, and LY-2456302. In some embodiments, "aticaprant" refers to the (S)-enantiomer of aticaprant, i.e., the following compound:

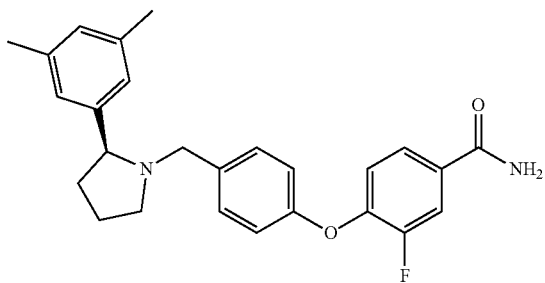 [SMILES: Cc1cc(C)cc([C@@H]2CCCN2Cc2ccc(Oc3ccc(C(N)=O)cc3F)cc2)c1]

also known as (S)-aticaprant or (S)-3-fluoro-4-4-2-(3,5-dimethylphenyl)pyrrolidin-1-yl-methylphenoxybenzamide. In other embodiments, the aticaprant used in the methods described herein is substantially free of the (R)-enantiomer, i.e., (R)-aticaprant or (R)-3-fluoro-4-4-2-(3,5-dimethylphenyl)pyrrolidin-1-yl-methylphenoxybenzamide having the following structure:

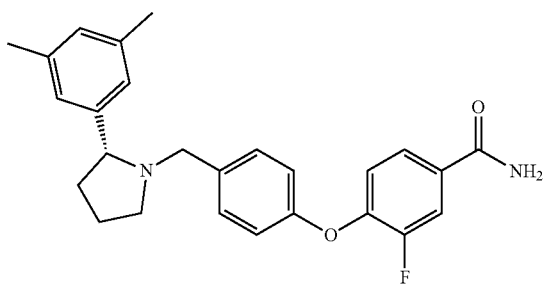 [SMILES: Cc1cc(C)cc([C@H]2CCCN2Cc2ccc(Oc3ccc(C(N)=O)cc3F)cc2)c1]

In other embodiments, the aticaprant contains less than about 10% by weight, based on the weight of the aticaprant, of the (R)-enantiomer of aticaprant. In further embodiments, the aticaprant contains less than about 10, about 9, about 8, about 7, about 6, about 5, about 4, about 3, about 2, about 1, about 0.5, about 0.1, about 0.005, or about 0.001% by weight, based on the weight of the aticaprant, of the (R)-enantiomer of aticaprant. In yet other embodiments, the aticaprant contains about 0.001 to about 10% by weight, based on the weight of the aticaprant, of the (R)-enantiomer of aticaprant. In still further embodiments, the aticaprant contains about 0.001 to about 10%, about 0.001 to about 5%, about 0.001 to about 1, about 0.001 to about 0.5, about 0.001 to about 0.1, about 0.1 to about 5, about 0.1 to about 1, about 0.1 to about 5, or about 0.5 to about 5% by weight, based on the weight of the aticaprant, of the (R)-enantiomer of aticaprant.

Pharmaceutically acceptable salts of aticaprant are also contemplated by the present invention, which may be readily selected by those skilled in the art. A "pharmaceutically acceptable salt" refers a salt of aticaprant that is non-toxic, biologically tolerable, or otherwise biologically suitable for administration to the subject. See, generally, G. S. Paulekuhn, "Trends in Active Pharmaceutical Ingredient Salt Selection based on Analysis of the Orange Book Database", J. Med. Chem., 2007, 50:6665-72, S. M. Berge, "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002. Examples of pharmaceutically acceptable salts are those that are pharmacologically effective and suitable for administration to patients without undue toxicity, irritation, or allergic response.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, bromides (such as hydrobromides), iodides (such as hydroiodides), acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propane-sulfonates, naphthalene-1-sulfonates, naphthalene-2-sulfonates, and mandelates.

The methods described herein include administering an effective amount of aticaprant, or a pharmaceutically acceptable salt thereof to the patient. The term "effective amount" as used herein, means that amount of active compound or pharmaceutical agent that elicits the biological or medicinal response in a human that is being sought by a researcher, medical doctor or other clinician, which includes alleviation of one or more of the symptoms of the disease or disorder being treated. In some embodiments, aticaprant is utilized in an effective amount as determined by the attending physician. In other embodiments, other antidepressant(s) is utilized in an effective amount either separately or in combination with aticaprant.

The amount of aticaprant for administration according to the methods described herein may be determined by one skill in the art and, unless otherwise noted, are set forth on an aticaprant free base basis. That is, the amounts indicate that amount of the aticaprant molecule administered, exclusive of, for example, solvent (such as in solvates) or counterions (such as in pharmaceutically acceptable salts). In some embodiments, the effective amount of aticaprant is less than about 60 mg. In other embodiments, the effective amount of aticaprant is about 0.5 mg, about 1 mg, about 2 mg, about 4 mg, about 5 mg, about 10 mg, about 15 mg, about 20 mg, 25 mg, about 30 mg, about 35 mg, about 40 mg, about 45 mg, about 50 mg, about 55 mg, or about 60 mg. In further embodiments, the effective amount of aticaprant is about 1 to about 50 mg, about 5 to about 50 mg, about 10 to about 50 mg, about 20 to about 50 mg, about 30 to about 50 mg, about 40 to about 50 mg, about 1 to about 45 mg, about 2 to about 45 mg, about 5 to about 45 mg, about 10 to about 45 mg, about 20 to about 45 mg, about 30 to about 45 mg, about 30 to about 40 mg, about 30 to about 35 mg, about 1 to about 40 mg, about 5 to about 40 mg, about 10 to about 40 mg, about 20 to about 40 mg, about 30 to about 40 mg, about 1 to about 35 mg, about 2 to about 35 mg, about 5 to about 35 mg, about 10 to about 35 mg, about 20 to about 35 mg, about 25 to about 35 mg, about 30 to about 35 mg, about 1 to about 30, about 2 to about 30 mg, about 5 to about 30 mg, about 10 to about 30 mg, about 20 to about 30 mg, about 25 to about 30 mg, about 1 to about 20 mg, about 2 to about 20 mg, about 5 to about 20 mg, about 10 to about 20 mg, about 15 to about 20 mg, about 1 to about 15 mg, about 2 to about 15 mg, about 5 to about 15 mg, about 10 to about 15 mg, about 1 to about 10 mg, about 2 to about 10 mg, or about 5 to about 10 mg. In yet other embodiments, the effective amount of aticaprant is about 5 to about 15 mg. In still further embodiments, the effective amount of aticaprant is about 10 mg.

As used herein, the term "composition" is intended to encompass a product comprising the specified ingredients in the specified amounts, as well as any product which results, directly or indirectly, from combinations of the specified ingredients in the specified amounts. The preferred pharmaceutical composition contains aticaprant as the active ingredient intimately admixed with a pharmaceutical carrier according to conventional pharmaceutical compounding techniques, which carrier may take a wide variety of forms depending of the form of preparation desired for administration. Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

In certain embodiments, pharmaceutical composition for use herein, the composition further comprises one or more buffers, preservatives, penetration agents, wetting agents, surfactants, solubilizing agents, thickening agents, colorant agents, antioxidants, emulsifying agents, isotonizing agents, suspending agents, and/or viscosity increasing agents.

In some embodiments, the pharmaceutical compositions comprises one or more buffers and/or buffer systems (i.e. conjugate acid-base-pairs). As used herein, the term "buffer" shall mean any solid or liquid composition (preferably an aqueous, liquid composition) which when added to an aqueous formulation adjusts the pH of said formulation. One skilled in the art will recognize that a buffer may adjust the pH of the aqueous formulation in any direction (toward more acidic, more basic or more neutral pH). Preferably, the buffer is pharmaceutically acceptable. Suitable examples of buffers which may be used in the aqueous formulations described herein include, but are not limited to citric acid, sodium dihydrogen phosphate, disodium hydrogen phosphate, acetic acid, boric acid, sodium borate, succinic acid, tartaric acid, malic acid, lactic acid, fumaric acid, and the like.

Optionally, the pharmaceutical compositions herein may contain a preservative. As used herein, unless otherwise noted, the terms "antimicrobial preservative" and "preservative" refer to any substance that is added to pharmaceutical compositions in order to preserve them against microbial degradation or microbial growth. In this regard, microbial growth typically plays an essential role, i.e., the preservative serves the main purpose of avoiding microbial contamination. It may also be desirable to avoid any effect of the microbes on the active ingredients and excipients, respectively, i.e., to avoid microbial degradation. Representative examples of preservatives include, but are not limited to, benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

As used herein, the terms "penetration agent", "penetration enhancer", and "penetrant" refer to any substance that increases or facilitates absorption and/or bioavailability of aticaprant. Preferably, the penetration agent increases or facilitates absorption and/or bioavailability of aticaprant, following administration. Suitable examples include, but are not limited to tetradecyl maltoside, sodium glycocholate, tauroursodeoxycholic acid, lecithines, and the like; and chitosan (and salts), and surface active ingredients such as benzalkonium chloride, sodium dodecyl sulfate, sodium docusate, polysorbates, laureth-9, oxtoxynol, sodium deoxycholate, polyarginine, and the like. Preferably, the penetration agent is selected to meet one or more of the following general requirements:

(a) It is effective at increasing absorption of aticaprant, preferably in a temporary and/or reversible manner;
    (b) It is pharmacologically inert;
    (c) It is non-allergic, non-toxic and/or non-irritating;
    (d) It is highly potent (effective in small amounts);
    (e) It is compatible with the other components of the pharmaceutical composition;
    (f) It is odorless, colorless and/or tasteless;
    (g) It is accepted by regulatory agencies; and
    (h) It is inexpensive and available in high purity.

The pharmaceutical compositions for use herein may further contain one or more additional excipients for example, wetting agents, surfactant components, solubilizing agents, thickening agents, colorant agents, antioxidant components, and the like.

Examples of a suitable antioxidant component, if used, include, but are not limited to one or more of the following: sulfites; ascorbic acid; ascorbates, such as sodium ascorbate, calcium ascorbate, or potassium ascorbate; ascorbyl palmitate; fumaric acid; ethylene diamine tetraacetic acid or its sodium or calcium salts; tocopherol; gallates, such as propyl gallate, octyl gallate, or dodecyl gallate; vitamin E; and mixtures thereof. The antioxidant component provides long term stability to the liquid compositions.

Solubilizing and emulsifying agents can be included to facilitate more uniform dispersion of the active ingredient or other excipient that is not generally soluble in the liquid carrier. Examples of a suitable emulsifying agent, if used, include, but are not limited to, for example, gelatin, cholesterol, acacia, tragacanth, pectin, methyl cellulose, carbomer, and mixtures thereof. Examples of suitable solubilizing agents include polyethylene glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof. The solubilizing or emulsifying agent may be present in an amount sufficient to dissolve or disperse the active ingredient, i.e., aticaprant, in the carrier.

A suitable isotonizing agent, if used, may include sodium chloride, glycerin, D-mannitol, D-sorbitol, glucose, and mixtures thereof.

Suspending agents or viscosity increasing agents may also be added to the pharmaceutical compositions. Suitable examples include, but are not limited to, hydroxypropyl methylcellulose, sodium carmellose, microcrystalline cellulose, carbomer, pectin, sodium alginate, chitosan salts, gellan gum, poloxamer, polyvinyl pyrrolidone, xanthan gum, and the like.

Advantageously, aticaprant may be administered once daily, or the total daily dosage may be administered in divided doses of two, three or four times daily.

As described herein, in particular, the patient had an inadequate response to other antidepressant therapy prior to treatment with aticaprant. Thus, in a particular embodiment, the disclosure relates to aticaprant, or a pharmaceutically acceptable salt thereof, for use as described herein, wherein the patient had an inadequate response to other antidepressant therapy prior to treatment with aticaprant. In a further particular embodiment, the disclosure also relates to the use of aticaprant, or a pharmaceutically acceptable salt thereof, in the manufacture of a medicament, as described herein, wherein the patient had an inadequate response to other antidepressant therapy prior to treatment with aticaprant. In a further particular embodiment, the disclosure further relates to a package or pharmaceutical product as described herein, wherein the patient had an inadequate response to other antidepressant therapy prior to treatment with aticaprant. Such antidepressant therapy can be in particular selected from a selective serotonin reuptake inhibitor (SSRI), serotonin-norepinephrine reuptake inhibitor (SNRI), or a combination thereof.

As described herein, aticaprant may be used as adjunctive treatment, or in other words, in conjunction, as an add-on, or in combination with one or more antidepressants, for example, the patient may be already, or also, administered one or more antidepressants. Thus, in a further particular embodiment, the disclosure relates to aticaprant, or a pharmaceutically acceptable salt thereof, for use as described herein, comprising administration of aticaprant, or a pharmaceutically acceptable salt thereof, as adjunctive treatment with an effective amount of one or more antidepressants. In a further particular embodiment, the disclosure relates to aticaprant, or a pharmaceutically acceptable salt thereof, for use as described herein, comprising administration of aticaprant, or a pharmaceutically acceptable salt thereof, in conjunction with an effective amount of one or more antidepressants. In a further particular embodiment, the disclosure relates to aticaprant, or a pharmaceutically acceptable salt thereof, for use as described herein, comprising administration of aticaprant, or a pharmaceutically acceptable salt thereof, in combination with an effective amount of one or more antidepressants. In a further particular embodiment, the disclosure also relates to the use of aticaprant, or a pharmaceutically acceptable salt thereof, in the manufacture of a medicament, as described herein, wherein the treatment comprises administration of an effective amount of aticaprant, or a pharmaceutically acceptable salt thereof, as adjunctive treatment with an effective amount of one or more antidepressants. In a further particular embodiment, the disclosure also relates to the use of aticaprant, or a pharmaceutically acceptable salt thereof, as described herein, wherein the treatment comprises administration of an effective amount of aticaprant, or a pharmaceutically acceptable salt thereof, in conjunction with an effective amount of one or more antidepressants. In a further particular embodiment, the disclosure also relates to the use of aticaprant, or a pharmaceutically acceptable salt thereof, as described herein, wherein the treatment comprises administration of an effective amount of aticaprant, or a pharmaceutically acceptable salt thereof, in combination with an effective amount of one or more antidepressants. In a further particular embodiment, the disclosure further relates to a package or pharmaceutical product as described herein, wherein the instructions for treatment direct the administration of an effective amount of aticaprant, or a pharmaceutically acceptable salt thereof, as adjunctive treatment with an effective amount of one or more antidepressants. In a further particular embodiment, the disclosure further relates to a package or pharmaceutical product as described herein, wherein the instructions for treatment direct the administration of an effective amount of aticaprant, or a pharmaceutically acceptable salt thereof, in conjunction with an effective amount of one or more antidepressants. In a further particular embodiment, the disclosure further relates to a package or pharmaceutical as described herein, wherein the instructions for treatment direct administration of an effective amount of aticaprant, or a pharmaceutically acceptable salt thereof, in combination with an effective amount of one or more antidepressants. Such one or more antidepressants can be selected from a selective serotonin reuptake inhibitor (SSRI), serotonin-norepinephrine reuptake inhibitor (SNRI), or a combination thereof.

As already described, the disclosure relates to aticaprant, or a pharmaceutically acceptable salt thereof, for use as described herein. In a particular embodiment, aticaprant is S-aticaprant, or a pharmaceutically acceptable salt thereof. In a further embodiment of the disclosure, aticaprant, in particular S-aticaprant, or a pharmaceutically acceptable salt thereof, for use as described herein, is to be administered in an amount of about 2 to about 35 mg, more in particular, of about 10 mg. In a yet further embodiment, aticaprant, in particular S-aticaprant, or a pharmaceutically acceptable salt thereof, for use as described herein, is administered orally. Furthermore, in a further particular embodiment, the disclosure relates to aticaprant, in particular S-aticaprant, or a pharmaceutically acceptable salt thereof, for use as described herein, administered once daily. The disclosure also relates to the use of aticaprant, or a pharmaceutically acceptable salt thereof, in the manufacture of a medicament, as described herein. In a particular embodiment, aticaprant is S-aticaprant, or a pharmaceutically acceptable salt thereof. In a further embodiment of the use as described herein, about 2 to about 35 mg aticaprant is to be administered, more in particular, about 10 mg. In a yet further embodiment of the use, aticaprant is to be administered orally. Furthermore, in a further particular embodiment of the use the aticaprant, in particular S-aticaprant, or a pharmaceutically acceptable salt thereof, is to be administered once daily. In a further particular embodiment, the disclosure further relates to a package or pharmaceutical product as described herein, wherein aticaprant is in particular S-aticaprant, or a pharmaceutically acceptable salt thereof. In a further embodiment of the package or pharmaceutical product as described herein, the instructions for treatment direct administration of about 2 to about 35 mg aticaprant, more in particular, about 10 mg. In a yet further embodiment of the package or pharmaceutical product as described herein, the instructions for treatment direct aticaprant, in particular S-aticaprant, or a pharmaceutically acceptable salt thereof, is for oral administration. Furthermore, in a further particular embodiment of the package or pharmaceutical product, as described herein, the instructions for treatment direct aticaprant, in particular S-aticaprant, or a pharmaceutically acceptable salt thereof, is for once daily administration.

Advantageously, administration of aticaprant does not result in weight gain during treatment, including clinically relevant weight gain. Thus, in a further particular embodiment, the disclosure relates to aticaprant, or a pharmaceutically acceptable salt thereof, for use as described herein, wherein the patient does not experience weight gain during the treatment with aticaprant. In a further particular embodiment, the disclosure relates to a use as defined herein, wherein the patient does not experience weight gain during the treatment with aticaprant. In a further particular embodiment, the disclosure further relates to a package or pharmaceutical product as described herein, wherein the patient does not experience weight gain during the treatment with aticaprant. The body weight of the patient can in particular be assessed at the time of the initial administration of aticaprant.

It was also unexpectedly observed that, based on assessment at the time of initial administration, the patient does not experience a decrease in sexual functioning during the treatment with aticaprant. Thus, in further particular embodiment, the disclosure relates to aticaprant, or a pharmaceutically acceptable salt thereof, for use as described herein, wherein the patient does not experience a decrease in sexual functioning during the treatment with aticaprant. In a further particular embodiment, the disclosure relates to a use as described herein, wherein the patient does not experience a decrease in sexual functioning during the treatment with aticaprant. In a further particular embodiment, the disclosure relates to a package or pharmaceutical product as described herein, wherein the patient does not experience a decrease in sexual functioning during the treatment with aticaprant. Such term "sexual functioning" comprises sexual drive, sexual arousal, vaginal lubrication, erection, orgasm achievement, or orgasm satisfaction. Sexual satisfaction can be assessed by methods known to the skilled person, for example, by applying the Arizona Sexual Experience Scale (ASEX).

As already described, the patient has moderate or severe anhedonia. Anhedonia can be measured, through an anhedonia scale, for example, the Snaith Hamilton Pleasure Scale (SHAPS). Thus, in a particular embodiment, the disclosure relates to aticaprant, or a pharmaceutically acceptable salt thereof, for use as described herein, wherein the anhedonia of the patient is reduced by at least 40%, as measured by the change from baseline in total score in an anhedonia scale following 6 weeks of the treatment with aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS). Thus, in a particular embodiment, the disclosure relates to the use as described herein, wherein the anhedonia of the patient is reduced by at least 40%, as measured by the change from baseline in total score in an anhedonia scale following 6 weeks of the treatment with aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS). In a further particular embodiment, the disclosure relates to the package or pharmaceutical product as described herein, wherein the anhedonia of the patient is reduced by at least 40%, as measured by the change from baseline in total score in an anhedonia scale following 6 weeks of the treatment with aticaprant, more in particular, the anhedonia of the patient is reduced within about 3 weeks to about 6 weeks as measured by the change from baseline in total score in an anhedonia scale. In a further particular embodiment, the anhedonia scale is the Snaith Hamilton Pleasure Scale (SHAPS).

Aspects

Aspect 1: A method for treating major depressive disorder in a human patient having moderate or severe anhedonia, comprising administering to the patient in need thereof an effective amount of aticaprant, or a pharmaceutically acceptable salt thereof.

Aspect 2: The method of Aspect 1, wherein the patient had an inadequate response to other antidepressant therapy prior to treatment with aticaprant.

Aspect 3: The method of Aspect 2, wherein the other antidepressant therapy comprised a selective serotonin reuptake inhibitor (SSRI), serotonin-norepinephrine reuptake inhibitor (SNRI), or a combination thereof.

Aspect 4: The method of any one of the preceding Aspects, further comprising adjunctive treatment with an effective amount of one or more antidepressants.

Aspect 5: The method of Aspect 4, wherein the one or more antidepressants is a selective serotonin reuptake inhibitor (SSRI), serotonin-norepinephrine reuptake inhibitor (SNRI), or a combination thereof.

Aspect 6: The method of any one of the preceding Aspects, wherein the aticaprant is S-aticaprant, or a pharmaceutically acceptable salt thereof.

Aspect 7: The method of any one of the preceding Aspects, wherein the effective amount of aticaprant is about 2 to about 35 mg.

Aspect 8: The method of Aspect 7, wherein the effective amount of aticaprant is about 10 mg.

Aspect 9: The method of any one of the preceding Aspects, wherein the aticaprant is administered orally.

Aspect 10: The method of any one of the preceding Aspects, wherein the aticaprant is administered once daily.

Aspect 11: The method of any one of the preceding Aspects, wherein the patient has moderate anhedonia.

Aspect 12: The method of any one of Aspects 1 to 11, wherein the patient has severe anhedonia.

Aspect 13: The method of any one of the preceding Aspects, wherein the patient does not experience weight gain during the treatment with aticaprant.

Aspect 14: The method of Aspect 13, wherein patient's body weight is assessed at the time of the initial administration of the aticaprant.

Aspect 15: The method of any one of the preceding Aspects, wherein the patient does not experience a decrease in sexual functioning during the treatment with aticaprant.

Aspect 16: The method of Aspect 15, wherein the sexual functioning of the patient is assessed at the time of initial administration of the aticaprant.

Aspect 17: The method of Aspect 15 or 16, wherein the sexual functioning comprises sexual drive, sexual arousal, vaginal lubrication, erection, orgasm achievement, or orgasm satisfaction.

Aspect 18: The method of any one of Aspects 15-17, wherein sexual functioning is assessed by the Arizona Sexual Experience Scale (ASEX).

Aspect 19: The method of any one of the preceding Aspects, wherein the anhedonia of the patient is reduced by at least 40%, as measured by the change from baseline in total score in an anhedonia scale following 6 weeks of the treatment with aticaprant.

Aspect 20: The method of any one of the preceding Aspects, wherein the anhedonia of the patient is reduced within about 3 weeks to about 6 weeks as measured by the change from baseline in total score in an anhedonia scale.

Aspect 21: The method of Aspect 19 or 20, wherein the anhedonia scale is the Snaith Hamilton Pleasure Scale (SHAPS).

Aspect 22: The method of any one of the preceding Aspects, wherein the administration of the aticaprant achieves a maximum plasma concentration (Cmax) of aticaprant of about 20 to about 45 ng/mL.

Aspect 23: The method of any one of the preceding Aspects, wherein the administration of the aticaprant achieves a maximum plasma concentration (Cmax) of aticaprant of about 25 to about 35 ng/mL.

Aspect 24: The method of any one of the preceding Aspects, wherein the administration of the aticaprant achieves a maximum plasma concentration (Cmax) of aticaprant of about 30 to about 35 ng/mL.

Aspect 25: Aticaprant, or a pharmaceutically acceptable salt thereof, for use in the treatment of major depressive disorder in a human patient having moderate or severe anhedonia.

Aspect 26: Aticaprant, or a pharmaceutically acceptable salt thereof, for use according to Aspect 25, wherein the treatment comprises administration of an effective amount of aticaprant, or a pharmaceutically acceptable salt thereof.

Aspect 27: Aticaprant, or a pharmaceutically acceptable salt thereof, for use according to Aspect 25 or 26, wherein the patient had an inadequate response to other antidepressant therapy prior to treatment with aticaprant.

Aspect 28: Aticaprant, or a pharmaceutically acceptable salt thereof, for use according to any one of Aspects 25 to 27, wherein the other antidepressant therapy comprised a selective serotonin reuptake inhibitor (SSRI), serotonin-norepinephrine reuptake inhibitor (SNRI), or a combination thereof.

Aspect 29: Aticaprant, or a pharmaceutically acceptable salt thereof, for use according to any one of Aspects 25 to 28, further comprising adjunctive treatment with an effective amount of one or more antidepressants.

Aspect 30: Aticaprant, or a pharmaceutically acceptable salt thereof, for use according to any one of Aspects 25 to 29, wherein the one or more antidepressants is a selective serotonin reuptake inhibitor (SSRI), serotonin-norepinephrine reuptake inhibitor (SNRI), or a combination thereof.

Aspect 31: Aticaprant, or a pharmaceutically acceptable salt thereof, for use according to any one of Aspects 25 to 30, wherein the aticaprant is S-aticaprant, or a pharmaceutically acceptable salt thereof.

Aspect 32: Aticaprant, or a pharmaceutically acceptable salt thereof, for use according to any one of Aspects 25 to 31, wherein the effective amount of aticaprant is about 2 to about 35 mg.

Aspect 33: Aticaprant, or a pharmaceutically acceptable salt thereof, for use according to Aspect 32, wherein the effective amount of aticaprant is about 10 mg.

Aspect 34: Aticaprant, or a pharmaceutically acceptable salt thereof, for use according to any one of Aspects 25 to 33, wherein the aticaprant is administered orally.

Aspect 35: Aticaprant, or a pharmaceutically acceptable salt thereof, for use according to any one of Aspects 25 to 34, wherein the aticaprant is administered once daily.

Aspect 36: Aticaprant, or a pharmaceutically acceptable salt thereof, for use according to any one of Aspects 25 to 35, wherein the patient has moderate anhedonia.

Aspect 37: Aticaprant, or a pharmaceutically acceptable salt thereof, for use according to any one of Aspects 25 to 35, wherein the patient has severe anhedonia.

Aspect 38: Aticaprant, or a pharmaceutically acceptable salt thereof, for use according to any one of Aspects 25 to 37, wherein the patient does not experience weight gain during the treatment with aticaprant.

Aspect 39: Aticaprant, or a pharmaceutically acceptable salt thereof, for use according to Aspect 38, wherein patient's body weight is assessed at the time of the initial administration of the aticaprant.

Aspect 40: Aticaprant, or a pharmaceutically acceptable salt thereof, for use according to any one of Aspects 25 to 39, wherein the patient does not experience a decrease in sexual functioning during the treatment with aticaprant.

Aspect 41: Aticaprant, or a pharmaceutically acceptable salt thereof, for use according to Aspect 40, wherein the sexual functioning of the patient is assessed at the time of initial administration of the aticaprant.

Aspect 42: Aticaprant, or a pharmaceutically acceptable salt thereof, for use according to Aspect 40 or 41, wherein the sexual functioning comprises sexual drive, sexual arousal, vaginal lubrication, erection, orgasm achievement, or orgasm satisfaction.

Aspect 43: Aticaprant, or a pharmaceutically acceptable salt thereof, for use according to any one of Aspects 40 to 42, wherein sexual functioning is assessed by the Arizona Sexual Experience Scale (ASEX).

Aspect 44: Aticaprant, or a pharmaceutically acceptable salt thereof, for use according to any one of Aspects 25 to 43, wherein the anhedonia of the patient is reduced by at least 40%, as measured by the change from baseline in total score in an anhedonia scale following 6 weeks of the treatment with aticaprant.

Aspect 45: Aticaprant, or a pharmaceutically acceptable salt thereof, for use according to any one of Aspects 25 to 44, wherein the anhedonia of the patient is reduced within about 3 weeks to about 6 weeks as measured by the change from baseline in total score in an anhedonia scale.

Aspect 46: Aticaprant, or a pharmaceutically acceptable salt thereof, for use according to Aspect 44 or 45, wherein the anhedonia scale is the Snaith Hamilton Pleasure Scale (SHAPS).

Aspect 47: Aticaprant, or a pharmaceutically acceptable salt thereof, for use according to any one of Aspects 25 to 46, wherein the aticaprant achieves a maximum plasma concentration (Cmax) of aticaprant of about 20 to about 45 ng/mL.

Aspect 48: Aticaprant, or a pharmaceutically acceptable salt thereof, for use according to any one of Aspects 25 to 47, wherein the aticaprant achieves a maximum plasma concentration (Cmax) of aticaprant of about 25 to about 35 ng/mL.

Aspect 49: Aticaprant, or a pharmaceutically acceptable salt thereof, for use according to any one of Aspects 25 to 48, wherein the aticaprant achieves a maximum plasma concentration (Cmax) of aticaprant of about 30 to about 35 ng/mL.

Aspect 50: Use of aticaprant, or a pharmaceutically acceptable salt thereof, in the manufacture of a medicament for the treatment of major depressive disorder in a human patient having moderate or severe anhedonia.

Aspect 51: Use according to Aspect 50, wherein the treatment comprises administration of an effective amount of aticaprant, or a pharmaceutically acceptable salt thereof.

Aspect 52: Use according to Aspect 50 or 51, wherein the patient had an inadequate response to other antidepressant therapy prior to treatment with aticaprant.

Aspect 53: Use according to any one of Aspects 50 to 52, wherein the other antidepressant therapy comprised a selective serotonin reuptake inhibitor (SSRI), serotonin-norepinephrine reuptake inhibitor (SNRI), or a combination thereof.

Aspect 54: Use according to any one of Aspects 50 to 53, further comprising adjunctive treatment with an effective amount of one or more antidepressants.

Aspect 55: Use according to any one of Aspects 50 to 54, wherein the one or more antidepressants is a selective serotonin reuptake inhibitor (SSRI), serotonin-norepinephrine reuptake inhibitor (SNRI), or a combination thereof.

Aspect 56: Use according to any one of Aspects 50 to 55, wherein the aticaprant is S-aticaprant, or a pharmaceutically acceptable salt thereof.

Aspect 57: Use according to Aspect 50 to 51, wherein the amount of aticaprant is about 2 to about 35 mg.

Aspect 58: Use according to Aspect 57, wherein the amount of aticaprant is about 10 mg.

Aspect 59: Use according to any one of Aspects 50 to 58, wherein the aticaprant is to be administered orally.

Aspect 60: Use according to any one of Aspects 50 to 59, wherein the aticaprant is to be administered once daily.

Aspect 61: Use according to any one of Aspects 50 to 60, wherein the patient has moderate anhedonia.

Aspect 62: Use according to any one of Aspects 50 to 60, wherein the patient has severe anhedonia.

Aspect 63: Use according to any one of Aspects 50 to 62, wherein the patient does not experience weight gain during the treatment with aticaprant.

Aspect 64: Use according to Aspect 63, wherein patient's body weight is assessed at the time of the initial administration of the aticaprant.

Aspect 65: Use according to any one of Aspects 50 to 64, wherein the patient does not experience a decrease in sexual functioning during the treatment with aticaprant.

Aspect 66: Use according to Aspect 65, wherein the sexual functioning of the patient is assessed at the time of initial administration of the aticaprant.

Aspect 67: Use according to Aspect 65 or 66, wherein the sexual functioning comprises sexual drive, sexual arousal, vaginal lubrication, erection, orgasm achievement, or orgasm satisfaction.

Aspect 68: Use according to any one of Aspects 65 to 67, wherein sexual functioning is assessed by the Arizona Sexual Experience Scale (ASEX).

Aspect 69: Use according to any one of Aspects 50 to 68, wherein the anhedonia of the patient is reduced by at least 40%, as measured by the change from baseline in total score in an anhedonia scale following 6 weeks of the treatment with aticaprant.

Aspect 70: Use according to any one of Aspects 50 to 69, wherein the anhedonia of the patient is reduced within about 3 weeks to about 6 weeks as measured by the change from baseline in total score in an anhedonia scale.

Aspect 71: Use according to Aspect 69 or 70, wherein the anhedonia scale is the Snaith Hamilton Pleasure Scale (SHAPS).

Aspect 72: Use according to any one of Aspects 50 to 71, wherein the aticaprant achieves a maximum plasma concentration (Cmax) of aticaprant of about 20 to about 45 ng/mL.

Aspect 73: Use according to any one of Aspects 50 to 72, wherein the aticaprant achieves a maximum plasma concentration (Cmax) of aticaprant of about 25 to about 35 ng/mL.

Aspect 74: Use according to any one of Aspects 50 to 73, wherein the aticaprant achieves a maximum plasma concentration (Cmax) of aticaprant of about 30 to about 35 ng/mL.

The following Examples are set forth to aid in the understanding of the invention, and are not intended and should not be construed to limit in any way the invention set forth in the claims which follow thereafter.

| | Abbreviations |
|---|---|
| AE | Adverse Event |
| AESI | Adverse Event of special interest |
| ALKS | Alkermes |
| ALT | Alanine Aminotransferase |
| Anti-HEV (IgM) | Anti-hepatitis E Virus (Immunoglobulin M) |
| ASEX | Arizona Sexual Experiences Scale |
| AST | Aspartate Transaminase |
| ATRQ | Antidepressant Treatment History Questionnaire |
| BMI | Body Mass Index |
| CBD | Cannabidiol |
| CERC | Cerecor |
| CGI-S | Clinical Global Impression - Severity |
| CI | Confidence Interval |
| CPFQ | Cognitive and Physical Functioning Questionnaire |
| C-SSRS | Columbia Suicide Severity Rating Scale |
| DCS | Direct Current Stimulation |
| DSM-IV/5 | Diagnostic and Statistical Manual of Mental Disorders $4^{th}/5^{th}$ edition |
| ECG | Electrocardiogram |
| EQ-5D-5L | European Quality of Life, 5 Dimension, 5-Level |
| eITT | Enriched Intent-To-Treat (population) |
| EOT | End-Of-Treatment |
| FAS | Full Safety Analysis Set |
| FDA | Food and Drug Administration |
| fITT | Full Intent-To-Treat (population) |
| FSH | Follicle Stimulating Hormone |
| FT4 | Free Thyroxine |
| G17 | Gastrin-17 |
| GAD | General Anxiety Disorder |
| GAD-7 | Generalized Anxiety Disorder 7-item Scale |
| GI | Gastrointestinal |
| HAM-A \| HDRS-17 | Hamilton Depression Rating Scale |
| HAM-A6 | 6 Item Subscale from HAM-A |
| HPA | Hypothalamus Pituitary Adrenal |
| Hp IgG | Helicobacter IgG antibodies |
| KOR | Kappa Opioid Receptor |
| KSS | Karolinska Sleepiness Scale |
| LS | Least Squares |
| MADRS | Montgomery Asberg Depression Rating Scale |
| MAOI | Monoamine Oxidase Inhibitor |
| MDMA | Methylenedioxymethamphetamine |
| MCI | Mild Cognitive Impairment |
| MDD | Major Depressive Disorder |
| MDE | Maximum Desired Mean Exposure |
| MedDRA | Medical Dictionary for Regulatory Activities |
| MINI | Mini International Neuropsychiatric Interview |
| MMRM | Mixed-effects Model for Repeated Measures |
| NSAID | Nonsteroidal Anti-Inflammatory Drug |
| PCP | Phencyclidine |
| PGI | Pepsinogen I |
| PGII | Pepsinogen II |
| PGI-S | Patient Global Impression of Severity |
| PK | Pharmacokinetic |
| PPI | Proton Pump Inhibitor |
| PRO | Patient Reported Outcome |
| PWC-20 | Physician Withdrawal Checklist 20-items |
| QD | Once Daily |
| SAMe | S-Adenosyl Methionine |
| SCID-CT | Structured Clinical Interview for DSM-5 Axis I Disorders Clinical Trials |
| SATE | Self-Assessment of Treatment Experience |
| SD | Standard Deviation |
| SDS | Sheehan Disability Scale |
| SHAPS | Snaith-Hamilton Pleasure Scale |
| SIGH-A | Structured Interview Guide for the Hamilton Anxiety scale |
| SIGMA | The Structured Interview Guide for the MADRS |
| SMDDS | Symptoms of Major Depressive Disorder Scale |

-continued

| Abbreviations | |
|---|---|
| SNRI | Serotonin-Norepinephrine Reuptake Inhibitor |
| SSRI | Selective Serotonin Reuptake Inhibitor |
| T3 | Thyroxine/triiodothyronine |
| TEAE | Treatment-Emergent Adverse Event |
| TMS | Transcranial Magnetic Stimulation |
| TSH | Thyroid-Stimulating Hormone |
| ULN | Upper Limit of Normal |
| WOCBP | Women of Childbearing Potential |

Example 1

This was a multi-center, placebo-controlled, randomized, double-blind study in subjects with MDD who have had an inadequate response to SSRI/SNRI treatment. Aticaprant was evaluated as an adjunctive therapy; therefore, eligible subjects were maintained on their SSRI/SNRT treatment without change throughout the study. At least 50% of recruited subjects had to be anhedonic (as measured by SHAPS total score≥20).

A. Objectives

The primary objective was to evaluate the efficacy of aticaprant compared to placebo when administered as adjunctive treatment in subjects with MDD partially responsive to SSRI/SNRI treatment in terms of reduction of symptoms of depression, as assessed by the change from baseline on the MADRS in non-responders during the placebo lead-in period.

The secondary objectives are:
  i. To evaluate the efficacy of aticaprant compared to placebo when administered as adjunctive treatment in subjects with MDD partially responsive to SSRI/SNRI treatment in terms of reduction of symptoms of depression, as assessed by the change from baseline on the MADRS in both responders and non-responders during the placebo lead-in period.
  ii. To investigate the overall safety and tolerability of treatment with adjunctive aticaprant in subjects with MDD when used in combination with a SSRI or SNRI.
  iii. To investigate the effect of aticaprant versus placebo on depression related anhedonia as assessed by the SHAPS.
  iv. To investigate the effect of aticaprant on symptoms of depression using the Clinical Global Impression-Severity (CGI-S), the patient reported Symptoms of Major Depressive Disorder Scale (SMDDS) and the self-assessment of treatment experience (SATE).
  v. To investigate the effect of aticaprant on symptoms of anxiety using the HAM-A and on core symptoms of anxiety using the HAM-A$_6$ subscale.
  vi. To assess the plasma PK of aticaprant in subjects with MDD and explore its relationship with efficacy and safety parameters.

Secondary exploratory objectives include:
  i. To explore the effect of aticaprant on aspects of cognitive and executive function using the CPFQ.
  ii. To explore mood-related biomarkers (including but not limited to growth factors, HPA axis markers, immune system activation, metabolic markers) and genetic/epigenetic variation that may be related to clinical response, nonresponse, or safety and tolerability parameters of aticaprant.

B. Study Design

For each subject, the study consisted of two phases: a screening phase of up to 5 weeks and a double-blind treatment phase lasting 11 weeks. See, FIG. 1.

Subjects with MDD who have had treatment initiated with a permitted SSRI/SNRI and have had an inadequate or only partial response to this treatment were screened. Assessments include the MINI, Antidepressant Treatment History Questionnaire (TRQ), and MADRS.

The treatment phase consisted of 3 periods. A placebo lead-in period of concealed duration, after which subjects entered the double-blind treatment period when they were randomly assigned to 10 mg aticaprant (two 5 mg capsules) or continue placebo for 6 weeks. Each capsule contained aticaprant (5 mg), microcrystalline cellulose (94.95 mg), and magnesium stearate (0.05 mg) in a hard gelatin capsule. Subjects who completed the treatment period, entered the withdrawal period and were treated with placebo for the remaining time of the treatment phase. The total duration for each subject was approximately 16 weeks. There were 11 scheduled visits, including screening. An overall flow diagram is shown in FIG. 1.

Subjects were screened within 35 to 2 days prior to Day 1 to ascertain their eligibility per the inclusion and exclusion criteria. The symptoms of depression were assessed using the structured interview guide for the MADRS.

Double-Blind Treatment Phase

The duration of the double-blind treatment phase was 11 weeks divided into 3 periods. The subject received medication after completion of the visit on Day 1. The first dose was taken at home on Day 2. All medication was taken in fasting condition. At Visits 3, 4 and 5, the subjects were re-randomized to blind subjects the duration of the placebo lead-in period. During the double-blind phase, the subjects visited the center for out-patient visits every 1 to 2 weeks. See, Table 1.

TABLE 1

Time and Events Schedule (TES)

| | Phase | | | | | | | | | | |
|---|---|---|---|---|---|---|---|---|---|---|---|
| | Screening | $^a$Double-blind treatment phase Visit number | | | | | | | | | |
| | 1 | 2 | 3 | 4 | 5 | 6 | 7 | 8 | 9 | 10 | $^b$11 or EW |
| Week (end of) | −5 to 0 | 0 | 1 | 2 | 3 | 4 | 6 | 7 | 8 | 9 | 11 |
| Day | −35 to −2 | 1 | 8 | 15 | 22 | 29 | 43 | 50 | 57 | 64 | 78 |
| Safety assessments | | | | | | | | | | | |
| Physical and neurological examination | X | X | | | X | | | | | | X |

TABLE 1-continued

Time and Events Schedule (TES)

| | Screening | [a]Double-blind treatment phase Visit number | | | | | | | | | |
|---|---|---|---|---|---|---|---|---|---|---|---|
| | 1 | 2 | 3 | 4 | 5 | 6 | 7 | 8 | 9 | 10 | [b]11 or EW |
| ASEX | | X | | | X | X | X | | | X | X |
| KSS | | X | | | X | X | X | | | X | X |
| Suicidality by C-SSRS | X | X | X | X | X | X | X | X | X | X | X |
| Dosing | | | | | | | | | | | |
| Randomization | | X | X | X | X | | | | | | |
| Supply new medication | | X | X | X | X | X | X | X | X | X | |
| Oral dose medication[d] | | | Day 2 until and including Day 78[e] | | | | | | | | |
| Meal after dosing | | X[l] | X[l] | X[l] | X[l] | X[l] | X[l] | X[l] | X[l] | X[l] | X[l] |
| Clinical Assessments | | | | | | | | | | | |
| Structured Interview Guide MADRS | X[j] | X | X | X | X | X | X | X | X | X | X |
| Structured Interview Guide SIGH-A | | X | X | X | X | X | X | X | X | X | X |
| CGI-S | | X | X | X | X | X | X | X | X | X | X |
| SMDDS | | X | | | X | X | X | | | X | |
| CPFQ | | X | | | X | X | X | | | X | |
| SHAPS | X | X | X | X | X | X | X | X | X | X | X |
| SATE[k] | | | | | once weekly while at home | | | | | | |
| Ongoing subject review | | | | | | | | | | | |
| Assessment of subject engagement[k] | X | | | | up to 3 occasion when at home | | | | | | |
| Adverse events | | | | | Continuous | | | | | | |
| Concomitant medication | | | | | Continuous | | | | | | |

EW = early withdrawal;
[a]Visits should be conducted ±3 days of the scheduled day (based on Visit 2, not based on previous visit).
[b]If a subject discontinues treatment before the end of the double-blind treatment phase, EW visit should be completed.
[d]At home: In fasting condition. At clinic visit days: Use blisters dispensed at the previous visit. In fasting condition after completion of predose assessments.
[e]When Visit 11 is planned up to 3 days later, continue medication.
[j]During the first screening visit and by telephone up to 4 days before Visit 2, if 2 weeks or more elapse between the MADRS rating at screening and Visit 2.
[k]Using Q1.6-app on subjects' smartphone.
[l]Breakfast, lunch or dinner after drug intake at site.

Lead-in period: Subjects who successfully complete the baseline examination visit at the clinical site/unit, were treated with placebo for the entire duration of the lead-in period.

Treatment period: At the end of the lead-in period both placebo lead-in responders and placebo lead-in non-responders were randomized to receive either placebo or 10 mg aticaprant in a 1:1 ratio for 6 weeks. Subjects remained blinded to exact timing of the randomization, response criterion and drug treatment assignment for each subject.

Withdrawal period: Subjects who completed the double-blind treatment period prior to the end of Week 11 entered the withdrawal period where they were treated with placebo for the remaining time of the treatment phase.

C. Dosage and Administration

Aticaprant was supplied as 5-mg capsules. Placebo was supplied as matching capsules. All subjects took 2 capsules QD. The capsules were taken daily from Day 2 to Day 78 in fasting condition with some water (fasting for at least 4 hours before dosing). Medication was taken before breakfast. If the subject has forgotten to take the medication before breakfast, this was done before the next following meal, at the latest at dinner of the same day. If the subject remembered later than dinner, the dose of that day was omitted, and the subject took the dose before breakfast on the next day.

When Visit 11 was planned up to 3 days later, the subject continued medication until Visit 11.

The capsules were swallowed whole and not chewed, divided, dissolved or crushed. After having taken the medication, subjects did not to eat or drink for at least 30 minutes.

The first dose was taken in fasting condition on Day 2 of the double-blind phase. The dose of the medication was:
10 mg aticaprant: 2 capsules of 5 mg aticaprant
Placebo: 2 placebo capsules.

Medication dose was adjusted as needed to 5 mg QD based on the results of a blinded review of the safety data. When a dose reduction has been decided on, this only applied to new subjects and the dose of medication was:
5 mg aticaprant: 1 capsule of 5 mg aticaprant
Placebo: 1 placebo capsule.

As used herein, the Enriched ITT Analysis Set (eITT) is defined as all enrolled lead-in placebo non-responders who were randomized into a treatment period, received at least one dose of study medication in the treatment period and have at least one post-baseline MADRS assessment during the treatment period. Similarly, the Full ITT Analysis Set (fITT) is defined as all enrolled subjects who were randomized into a treatment period, received at least one dose of study medication in the treatment period and have at least one post-treatment baseline assessment of MADRS during the treatment period.

D. Clinical assessments (i) Depression: Montgomery-Åsberg Depression Rating Scale (MADRS), Clinical Global Impression-Severity (CGI-S), Symptoms of Major Depressive Disorder Scale (SMDDS), and Self-assessment of treatment experience (SATE)

(ii) Anhedonia: Snaith-Hamilton Pleasure Scale (SHAPS)

(iii) Anxiety: Structured Interview Guide for the Hamilton Anxiety scale (SIGH-A) and HAM-A6

(iv) Effects on Cognition: The Cognitive and Physical Functioning Questionnaire (CPFQ)

(v) Safety assessments

Standard safety assessments including physical and neurological examination, vital signs, 12-lead ECG, clinical chemistry, hematology, and urinalysis was performed. Based on observations of GI complaints in previous studies, a panel including PGI, PGII, G17 and Hp IgG was added to the clinical laboratory test panel to test for stomach mucosa status.

(vi) Suicidal ideation: C-SSRS (vii) Exploratory: CPFQ (viii) Central sedating effects: Karolinska Sleepiness Scale (ix) Sexual dysfunction: ASEX E. Patient Population Of 184 subjects, 169 were randomized into the treatment period and included in the safety population, while 166 subjects were considered for the full ITT population. Out of the 166 subjects in the full ITT population, 121 (73%) were lead-in placebo non-responders (enriched ITT population) and the remaining 45 (27%) were lead-in placebo responders. Of the 121 subjects in the enriched population, 112 (92.6%) were white and 84 (69.4%) were female. The mean age was 41.6 years, ranging from 19 to 64 years. All subjects had anhedonia (defined as SHAPS total score≥20) at treatment baseline. A high anhedonia level (defined as SHAPS total score≥38) was observed in 43.8% of the subjects. In general, the treatment groups were similar with respect to the baseline characteristics. Subject demographics for the eITT and safety analysis are provided in Tables 2 and 3.

TABLE 2

Summary of Demographics and Baseline Characteristics; Full Safety Analysis

| | Placebo (N = 84) | aticaprant 10 mg (N = 85) | Total (N = 169) |
|---|---|---|---|
| Age (Years) | | | |
| N | 84 | 85 | 169 |
| Mean (SD) | 42.1 (12.54) | 43.0 (12.81) | 42.6 (12.65) |
| Median | 43.5 | 43.0 | 43.0 |
| Range | (19; 64) | (21; 64) | (19; 64) |
| Gender | | | |
| N | 84 | 85 | 169 |
| Female | 62 (73.8%) | 60 (70.6%) | 122 (72.2%) |
| Male | 22 (26.2%) | 25 (29.4%) | 47 (27.8%) |
| Race | | | |
| N | 84 | 85 | 169 |
| American Indian or Alaska Native | 1 (1.2%) | 0 | 1 (0.6%) |
| Asian | 2 (2.4%) | 2 (2.4%) | 4 (2.4%) |
| Black or African American | 2 (2.4%) | 5 (5.9%) | 7 (4.1%) |
| White | 79 (94.0%) | 78 (91.8%) | 157 (92.9%) |

TABLE 2-continued

Summary of Demographics and Baseline Characteristics; Full Safety Analysis

| | Placebo (N = 84) | aticaprant 10 mg (N = 85) | Total (N = 169) |
|---|---|---|---|
| Ethnicity | | | |
| N | 84 | 85 | 169 |
| Hispanic or Latino | 10 (11.9%) | 13 (15.3%) | 23 (13.6%) |
| Not Hispanic or Latino | 74 (88.1%) | 72 (84.7%) | 146 (86.4%) |
| Country | | | |
| N | 84 | 85 | 169 |
| Germany | 4 (4.8%) | 5 (5.9%) | 9 (5.3%) |
| Moldova | 15 (17.9%) | 14 (16.5%) | 29 (17.2%) |
| Russia | 25 (29.8%) | 21 (24.7%) | 46 (27.2%) |
| Ukraine | 9 (10.7%) | 7 (8.2%) | 16 (9.5%) |
| United Kingdom | 10 (11.9%) | 15 (17.6%) | 25 (14.8%) |
| United States | 21 (25.0%) | 23 (27.1%) | 44 (26.0%) |
| Baseline Height (cm) | | | |
| N | 84 | 85 | 169 |
| Mean (SD) | 167.4 (7.91) | 168.2 (8.64) | 167.8 (8.27) |
| Median | 167.5 | 167.6 | 167.6 |
| Range | (150; 183) | (152; 195) | (150; 195) |
| Baseline Weight (kg) | | | |
| N | 84 | 85 | 169 |
| Mean (SD) | 76.2 (14.73) | 78.7 (15.23) | 77.4 (14.99) |
| Median | 75.3 | 78.9 | 77.1 |
| Range | (47; 116) | (42; 119) | (42; 119) |
| Baseline BMI (kg/m$^2$) | | | |
| N | 84 | 85 | 169 |
| Mean (SD) | 27.2 (4.92) | 27.7 (4.56) | 27.5 (4.73) |
| Median | 26.6 | 28.1 | 27.6 |
| Range | (19; 35) | (18; 35) | (18; 35) |
| Presence of Anhedonia at Baseline | | | |
| N | 84 | 85 | 169 |
| No | 0 | 1 (1.2%) | 1 (0.6%) |
| Yes | 84 (100.0%) | 84 (98.8%) | 168 (99.4%) |
| Lead-in response status | | | |
| N | 84 | 85 | 169 |
| No | 62 (73.8%) | 62 (72.9%) | 124 (73.4%) |
| Yes | 22 (26.2%) | 23 (27.1%) | 45 (26.6%) |

TABLE 3

Summary of Demographics and Baseline Characteristics; eITT

| | Placebo (N = 61) | aticaprant 10 mg (N = 60) | Total (N = 121) |
|---|---|---|---|
| Age (Years) | | | |
| N | 61 | 60 | 121 |
| Mean (SD) | 41.6 (12.34) | 41.6 (12.78) | 41.6 (12.51) |
| Median | 43.0 | 40.5 | 42.0 |
| Range | (19; 64) | (21; 64) | (19; 64) |
| Gender | | | |
| N | 61 | 60 | 121 |
| Female | 42 (68.9%) | 42 (70.0%) | 84 (69.4%) |
| Male | 19 (31.1%) | 18 (30.0%) | 37 (30.6%) |

TABLE 3-continued

Summary of Demographics and Baseline Characteristics; eITT

| | Placebo (N = 61) | aticaprant 10 mg (N = 60) | Total (N = 121) |
|---|---|---|---|
| Race | | | |
| N | 61 | 60 | 121 |
| American Indian or Alaska Native | 1 (1.6%) | 0 | 1 (0.8%) |
| Asian | 2 (3.3%) | 1 (1.7%) | 3 (2.5%) |
| Black or African American | 2 (3.3%) | 3 (5.0%) | 5 (4.1%) |
| White | 56 (91.8%) | 56 (93.3%) | 112 (92.6%) |
| Ethnicity | | | |
| N | 61 | 60 | 121 |
| Hispanic or Latino | 3 (4.9%) | 7 (11.7%) | 10 (8.3%) |
| Not Hispanic or Latino | 58 (95.1%) | 53 (88.3%) | 111 (91.7%) |
| Country | | | |
| N | 61 | 60 | 121 |
| Germany | 4 (6.6%) | 4 (6.7%) | 8 (6.6%) |
| Moldova | 15 (24.6%) | 14 (23.3%) | 29 (24.0%) |
| Russia | 19 (31.1%) | 18 (30.0%) | 37 (30.6%) |
| Ukraine | 7 (11.5%) | 5 (8.3%) | 12 (9.9%) |
| United Kingdom | 6 (9.8%) | 10 (16.7%) | 16 (13.2%) |
| United States | 10 (16.4%) | 9 (15.0%) | 19 (15.7%) |
| Baseline Height (cm) | | | |
| N | 61 | 60 | 121 |
| Mean (SD) | 168.1 (8.19) | 167.3 (8.10) | 167.7 (8.13) |
| Median | 168.0 | 166.3 | 167.0 |
| Range | (151; 183) | (152; 186) | (151; 186) |
| Baseline Weight (kg) | | | |
| N | 61 | 60 | 121 |
| Mean (SD) | 74.7 (14.19) | 76.8 (15.12) | 75.7 (14.63) |
| Median | 74.2 | 77.1 | 75.6 |
| Range | (47; 116) | (42; 119) | (42; 119) |
| Baseline BMI (kg/m$^2$) | | | |
| N | 61 | 60 | 121 |
| Mean (SD) | 26.4 (4.67) | 27.3 (4.36) | 26.9 (4.52) |
| Median | 25.7 | 27.8 | 26.7 |
| Range | (19; 35) | (18; 35) | (18; 35) |
| Presence of Anhedonia at Baseline | | | |
| N | 61 | 60 | 121 |
| No | 0 | 0 | 0 |
| Yes | 61 (100.0%) | 60 (100.0%) | 121 (100.0%) |
| Lead-in response status | | | |
| N | 61 | 60 | 121 |
| No | 61 (100.0%) | 60 (100.0%) | 121 (100.0%) |
| Yes | 0 | 0 | 0 |

E. Evaluations of Efficacy

At the end of the lead-in period, response status of the subjects was assessed according to the double-blind response criteria based on reduction in MADRS relative to lead-in baseline. Both lead-in placebo responders and lead-in placebo non-responders were randomly assigned in a 1:1 ratio to either aticaprant or placebo in the treatment period. The randomization was stratified by lead-in response status (non-responders: <30% reduction from baseline in MADRS total score at the end of the lead-in period vs responders: ≥30% reduction from baseline at the end of the lead-in period) and presence/absence of anhedonia (presence defined as SHAPS total score≥20).

Treatment duration: The study consisted of two periods: a screening phase of up to 5 weeks and a double-blind treatment phase of 11 weeks. The double-blind treatment phase of the trial consisted of 3 periods. The first period was a placebo lead-in of 3 weeks, after which subjects entered the treatment period when they were randomly assigned to aticaprant or continuation on placebo for 6 weeks. Subjects who successfully completed the treatment period were treated with placebo during a 2-week withdrawal period, i.e., Period 3. The total duration for each subject was approximately 16 weeks.

Primary analysis set for efficacy: The efficacy analysis is based on the eITT set defined as all enrolled lead-in placebo non-responders who were randomized into the treatment period, received at least one dose of medication, and have at least one post-baseline MADRS assessment during the treatment period. The primary analysis set is used for all efficacy endpoints.

Secondary analysis set for efficacy: A secondary analysis set is the fITT set defined as all enrolled subjects who were randomized into the treatment period, received at least one dose of medication, and have at least one post-baseline MADRS assessment during the treatment period. The secondary analysis set is used for all efficacy endpoints to examine the effect in the general population, which may be useful for designing subsequent studies in the development program.

Analysis set for safety: The safety analysis is based on the full safety analysis set, defined as all enrolled subjects who received at least one dose of medication in the treatment period.

The efficacy endpoints were presented for both the eITT and the fITT.

Level of significance: The analysis of primary efficacy endpoint was performed at a significance level of 0.20 (one-sided). The analysis of secondary efficacy endpoints was performed at a significance level of 0.20 (two-sided). No adjustment for multiple comparisons was performed.

Figure 2:
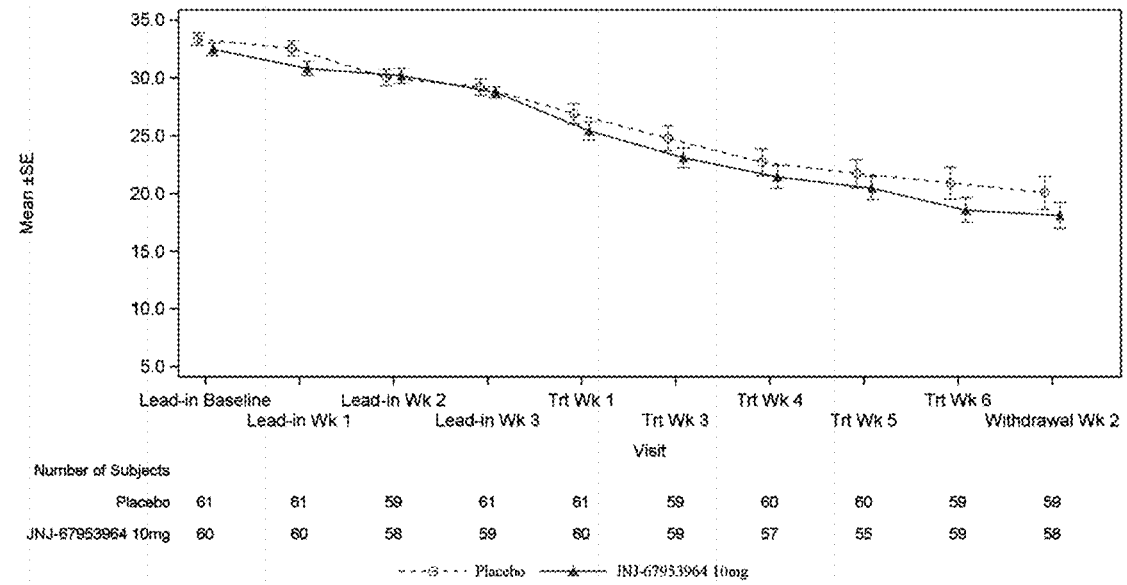
FIG. 2 is a line graph showing the MADRS (Montgomery-Åsberg Depression Rating Scale) total score: least squares mean changes from baseline (±SE) during the treatment period for the enriched intent-to-treat (eITT) analysis set.
Figure 6:
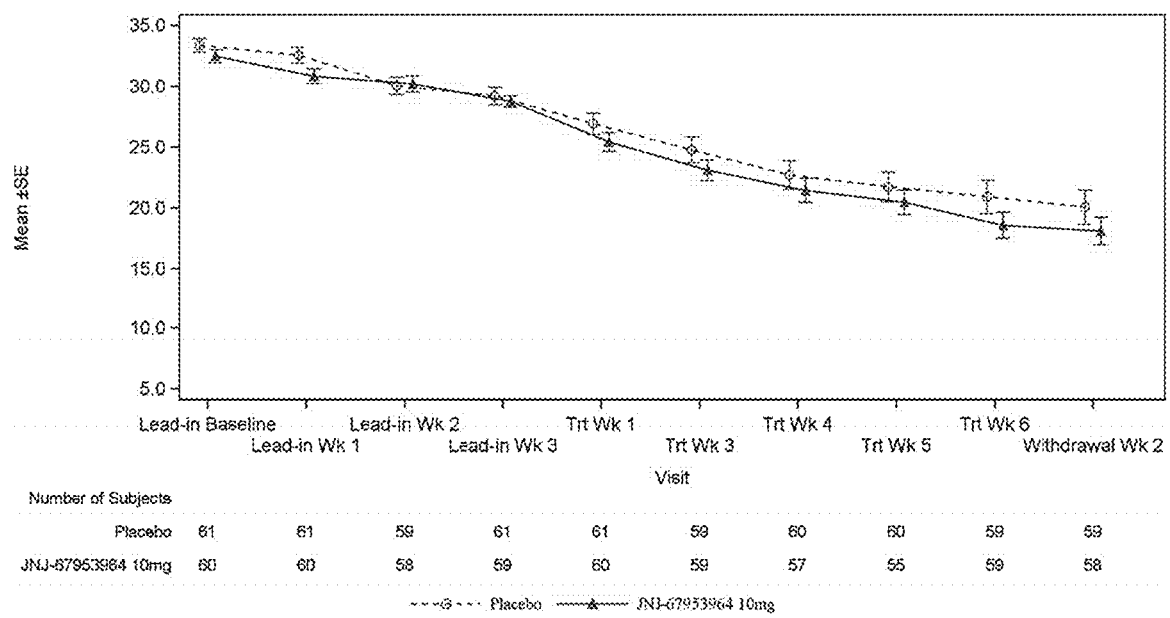
FIG. 6 is a line graph showing MADRS total score: mean values (±SE) over time for the eITT analysis set.

F. Results (i) Primary Endpoint: Change from Treatment Baseline in MADRS Total Score at Treatment Week 6 in Non-Responders during Placebo Lead-in Period Enriched ITT Analysis Set The mean (SD) MADRS total score at treatment baseline was 29.0 (4.61), ranging from 19 to 41. See, FIG. 2. The mean change from treatment baseline (SD) in MADRS total score at treatment week 6 was −10.2 (8.44) for aticaprant and −8.2 (8.53) for placebo. The observed effect size was 0.23. See, Tables 4-6 and FIG. 6.

TABLE 4

Summary of Baseline Psychiatry Rating Scales at the Start of the Lead-in and Treatment Periods; eITT Analysis Set

| | MADRS Total Score | | | SHAPS Total Score | | |
|---|---|---|---|---|---|---|
| | N | Mean (SD) | Median (Range) | N | Mean (SD) | Median (Range) |
| Lead-in Baseline | | | | | | |
| Placebo | 61 | 33.4 (4.25) | 34.0 (26; 42) | 61 | 38.0 (6.28) | 38.0 (22; 55) |
| Aticaprant | 60 | 32.5 (4.18) | 32.0 (25; 45) | 60 | 38.3 (5.66) | 38.0 (21; 53) |
| Total | 121 | 32.9 (4.22) | 33.0 (25; 45) | 121 | 38.1 (5.96) | 38.0 (21; 55) |
| Treatment Baseline | | | | | | |
| Placebo | 61 | 29.2 (5.47) | 29.0 (19; 41) | 61 | 36.8 (5.75) | 37.0 (23; 50) |
| Aticaprant | 60 | 28.7 (3.58) | 28.5 (21; 36) | 60 | 36.4 (5.16) | 36.5 (20; 49) |
| Total | 121 | 29.0 (4.61) | 29.0 (19; 41) | 121 | 36.6 (5.45) | 37.0 (20; 50) |

TABLE 5

MADRS Total Score: Mean Changes to Placebo During the Treatment Period; eITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 1 | | | | | |
| Placebo | 61 | −2.2 (3.73) | | | |
| Aticaprant | 60 | −3.3 (5.21) | −1.1 (4.52) | [−2.4, 0.3] | −0.24 |
| Treatment Week 3 | | | | | |
| Placebo | 59 | −4.3 (5.99) | | | |
| Aticaprant | 59 | −5.7 (6.38) | −1.4 (6.18) | [−3.3, 0.5] | −0.22 |
| Treatment Week 4 | | | | | |
| Placebo | 60 | −6.4 (6.66) | | | |
| Aticaprant | 57 | −7.3 (7.35) | −0.9 (7.00) | [−3.1, 1.2] | −0.14 |
| Treatment Week 5 | | | | | |
| Placebo | 60 | −7.4 (7.15) | | | |
| Aticaprant | 55 | −8.4 (7.36) | −1.1 (7.25) | [−3.3, 1.2] | −0.14 |
| Treatment Week 6 | | | | | |
| Placebo | 59 | −8.2 (8.53) | | | |
| Aticaprant | 59 | −10.2 (8.44) | −2.0 (8.49) | [−4.6, 0.6] | −0.23 |

Negative change from baseline indicates improvement. Negative change to Placebo indicates favorable aticaprant effect. Negative effect size favors aticaprant; positive effect size favors Placebo.

TABLE 6

MADRS Total Score: MMRM Results - Estimated LS Means and Comparison versus Placebo; eITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| Treatment Week 1 | | | | | | | |
| Placebo | 61 | 26.9 (6.77) | −2.2 (3.73) | −2.0 (0.92) | | | |
| aticaprant | 60 | 25.4 (5.93) | −3.3 (5.21) | −3.2 (0.93) | −1.2 (1.24) | [−2.28, −0.19] | 0.1604 |
| Treatment Week 3 | | | | | | | |
| Placebo | 59 | 24.8 (8.25) | −4.3 (5.99) | −4.2 (0.92) | | | |
| aticaprant | 59 | 23.1 (6.58) | −5.7 (6.38) | −5.6 (0.93) | −1.5 (1.25) | [−2.55, −0.44] | 0.1159 |
| Treatment Week 4 | | | | | | | |
| Placebo | 60 | 22.7 (9.10) | −6.4 (6.66) | −6.2 (0.92) | | | |
| aticaprant | 57 | 21.5 (7.49) | −7.3 (7.35) | −7.3 (0.93) | −1.1 (1.25) | [−2.19, −0.09] | 0.1811 |
| Treatment Week 5 | | | | | | | |
| Placebo | 60 | 21.7 (9.54) | −7.4 (7.15) | −7.2 (0.92) | | | |
| aticaprant | 55 | 20.5 (7.44) | −8.4 (7.36) | −8.7 (0.94) | −1.5 (1.25) | [−2.60, −0.48] | 0.1103 |

TABLE 6-continued

MADRS Total Score: MMRM Results - Estimated LS Means
and Comparison versus Placebo; eITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| Treatment Week 6 | | | | | | | |
| Placebo | 59 | 20.9 (10.54) | −8.2 (8.53) | −8.0 (0.92) | | | |
| aticaprant | 59 | 18.6 (8.14) | −10.2 (8.44) | −10.1 (0.93) | −2.1 (1.25) | [−3.20, −1.09] | 0.0443 |

Figure 3:
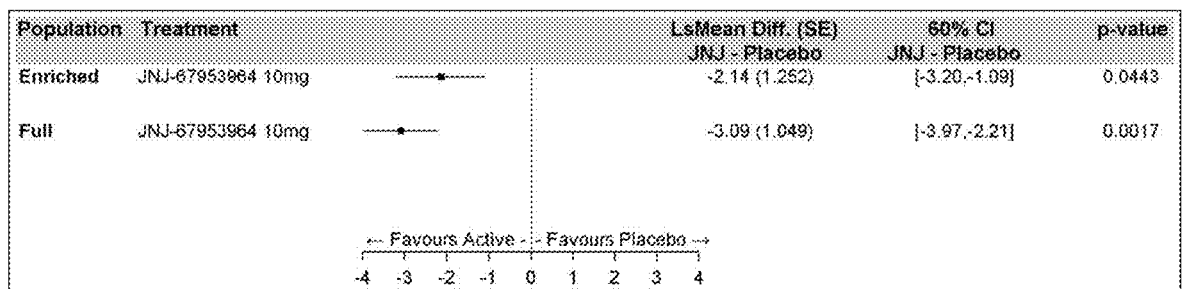
FIG. 3 is a plot showing MADRS total score changes at treatment week 6 for enriched and full population: MMRM results—estimated LS means and comparison versus placebo.

[a] One-sided test for no difference between treatments from a MMRM model with subject as random effect; country, treatment, time and time-by-treatment interaction as factors; and baseline MADRS total score as continuous covariate. An AR(1) variance-covariance matrix was employed Based on the results of a MMRM model with subject as random effect; country, treatment, time and time-by-treatment interaction as factors; and baseline MADRS total score as continuous covariate a significant positive efficacy signal was detected for aticaprant versus placebo at the one-sided 0.20 significance level. The estimated LS mean difference at treatment week 6 between aticaprant and placebo was −2.1 with 80% 1-sided CI upper limit of −1.09. The corresponding p-value was 0.044. The treatment effect was larger in the fITT than in the eITT population: −3.1 with 80% 1-sided CI upper limit of −2.2 (p=0.002). The effect size was 0.36 and 0.23, respectively. See, FIGS. 2 and 3.

Full ITT Analysis Set

Figure 7A:
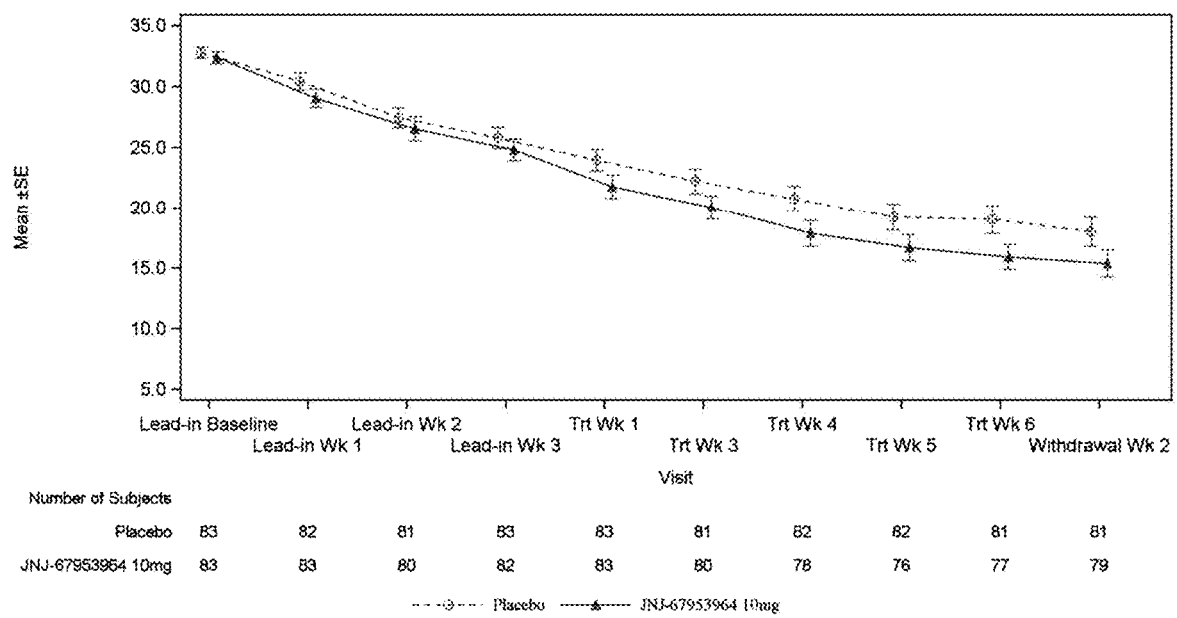
FIG. 7A is a line graph showing MADRS total score: mean values (±SE) over time for the full intent-to-treat (fITT) analysis set.

The mean (SD) baseline MADRS total score at treatment baseline was 25.3 (7.86), ranging from 0 to 41. See, FIGS. 7A and 7B. The mean changes from treatment baseline in MADRS total score at Treatment Week 6 for fITT were smaller than for eITT: −9.7 (8.02) for aticaprant and −6.6 (8.57) for placebo. The observed effect size was 0.36. These results illustrate a statistical superiority over placebo with a durability of effect with the greatest difference seen at week 6. See, Table 7.

TABLE 7

Summary of Baseline Psychiatry Rating Scales at the Start
of the Lead-in and Treatment Periods; fITT Analysis Set

| | MADRS Total Score | | | SHAPS Total Score | | |
|---|---|---|---|---|---|---|
| | N | Mean (SD) | Median (Range) | N | Mean (SD) | Median (Range) |
| Lead-in Baseline | | | | | | |
| Placebo | 83 | 32.8 (4.25) | 33.0 (26; 42) | 83 | 37.8 (6.01) | 38.0 (22; 55) |
| Aticaprant | 83 | 32.4 (4.27) | 32.0 (21; 45) | 83 | 37.3 (6.23) | 38.0 (14; 53) |
| Total | 166 | 32.6 (4.25) | 32.0 (21; 45) | 166 | 37.6 (6.11) | 38.0 (14; 55) |
| Treatment Baseline | | | | | | |
| Placebo | 83 | 25.7 (7.73) | 26.0 (10; 41) | 83 | 36.3 (5.44) | 36.0 (23; 50) |
| Aticaprant | 83 | 24.8 (8.02) | 27.0 (0; 36) | 83 | 35.0 (5.85) | 36.0 (14; 49) |
| Total | 166 | 25.3 (7.86) | 26.5 (0; 41) | 166 | 35.6 (5.67) | 36.0 (14; 50) |

Significant effect for aticaprant versus placebo in fITT population was also detected. The estimated LS mean difference at treatment week 6 between aticaprant and placebo was −3.1 with 80% 1-sided CI upper limit of −2.21. The corresponding p-value was 0.002. See, Tables 8-9 and FIG. 3.

TABLE 8

MADRS Total Score: MMRM Results - Estimated LS Means and Comparison versus Placebo; fITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| | | | Change from Baseline | | | | |
| | | | Treatment Week 1 | | | | |
| Placebo | 83 | 24.0 (8.12) | −1.8 (4.00) | −1.7 (0.78) | | | |
| aticaprant | 83 | 21.7 (8.78) | −3.1 (4.81) | −3.2 (0.77) | −1.6 (1.03) | [−2.44, −0.70] | 0.0653 |
| | | | Treatment Week 3 | | | | |
| Placebo | 81 | 22.2 (9.28) | −3.4 (6.50) | −3.4 (0.78) | | | |
| aticaprant | 80 | 20.0 (8.53) | −5.1 (6.74) | −5.2 (0.78) | −1.9 (1.04) | [−2.74, −0.99] | 0.0368 |
| | | | Treatment Week 4 | | | | |
| Placebo | 82 | 20.8 (9.24) | −4.9 (7.02) | −4.8 (0.78) | | | |
| aticaprant | 78 | 17.9 (9.32) | −7.2 (7.02) | −7.3 (0.78) | −2.5 (1.04) | [−3.34, −1.59] | 0.0093 |
| | | | Treatment Week 5 | | | | |
| Placebo | 82 | 19.2 (9.89) | −6.4 (7.16) | −6.3 (0.78) | | | |
| aticaprant | 76 | 16.7 (9.47) | −8.3 (7.48) | −8.7 (0.78) | −2.4 (1.05) | [−3.24, −1.47] | 0.0125 |
| | | | Treatment Week 6 | | | | |
| Placebo | 81 | 19.0 (10.35) | −6.6 (8.57) | −6.5 (0.78) | | | |
| aticaprant | 77 | 15.9 (9.09) | −9.7 (8.02) | −9.6 (0.79) | −3.1 (1.05) | [−3.97, −2.21] | 0.0017 |

[a]One-sided test for no difference between treatments from a MMRM model with subject as random effect; country, treatment, time and time-by-treatment interaction as factors; and baseline MADRS total score as continuous covariate. An AR(1) variance-covariance matrix was employed

TABLE 9

MADRS (Montgomery-Åsberg Depression Rating Scale) Total Score: Mean Changes to Placebo During the Treatment Period; fITT Analysis Set

| Analysis Visit Treatment | N | Mean Change to Placebo (SD pooled) | 90% CI for Mean Change to Placebo | Effect Size |
|---|---|---|---|---|
| | | Treatment Week 1 | | |
| Placebo | 83 | | | |
| Aticaprant | 83 | −1.3 (4.43) | [−2.4, −0.2] | −0.29 |
| | | Treatment Week 3 | | |
| Placebo | 81 | | | |
| Aticaprant | 80 | −1.7 (6.62) | [−3.4, 0.0] | −0.26 |
| | | Treatment Week 4 | | |
| Placebo | 82 | | | |
| Aticaprant | 78 | −2.3 (7.02) | [−4.1, −0.4] | −0.32 |
| | | Treatment Week 5 | | |
| Placebo | 82 | | | |
| Aticaprant | 76 | −1.9 (7.31) | [−3.9, −0.0] | −0.26 |
| | | Treatment Week 6 | | |
| Placebo | 81 | | | |
| Aticaprant | 77 | −3.0 (8.31) | [−5.2, −0.8] | −0.36 |

Negative change from baseline indicates improvement. Negative change to Placebo indicates favorable aticaprant effect. Negative effect size favors aticaprant; positive effect size favors Placebo.

COVID-19 Impact on Primary Efficacy Assessment

Supplementary analysis was conducted using the same MMRM model as described for the primary analysis on all the data collected prior to 15 Mar. 2020 (estimated date of the COVID-19 lockdowns in most of the countries participating in the trial). Seventeen percent of the subjects in fITT and 19% in eITT population had at least one of the MADRS assessment excluded from the model due to COVID-19 impact. Results of the analysis corroborated the findings of the primary efficacy analysis in both: eITT and fITT populations. LSMeans difference estimate was −3.0 (80% 1-sided CI upper limit of −1.88) for eITT and −3.4 (80% 1-sided CI upper limit of −2.51) for fITT.

(ii) Secondary Endpoints

MADRS Remission Rates Over Treatment Period

Figure 8:
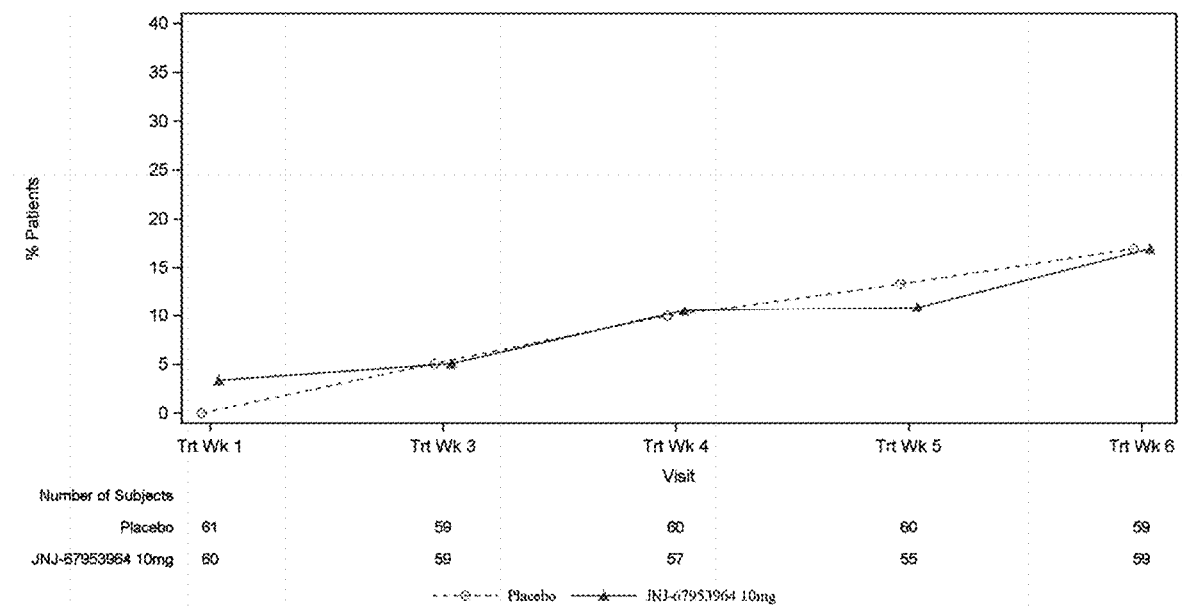
FIG. 8 is a line graph showing MADRS total score: percentage of subjects with remission of depressive symptoms (total score≤10) during the treatment period for the eITT analysis set.
Figure 9:
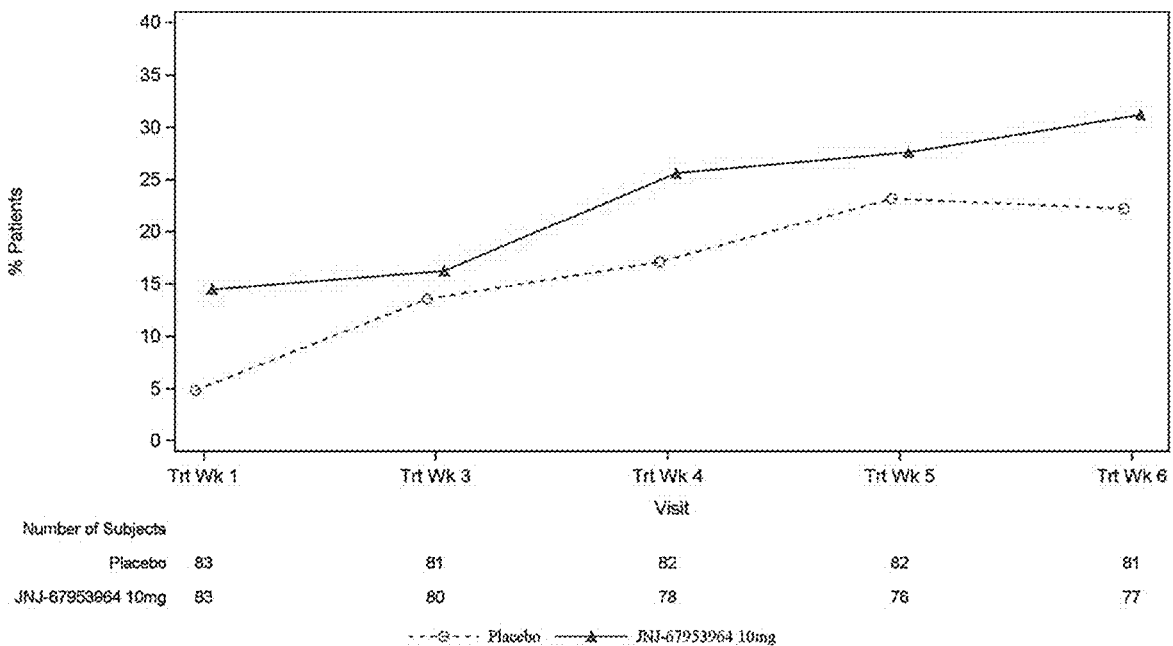
FIG. 9 is a line graph showing MADRS total score: percentage of subjects with remission of depressive symptoms (total score≤10) during the treatment period for the fITT analysis set.
Figure 10:
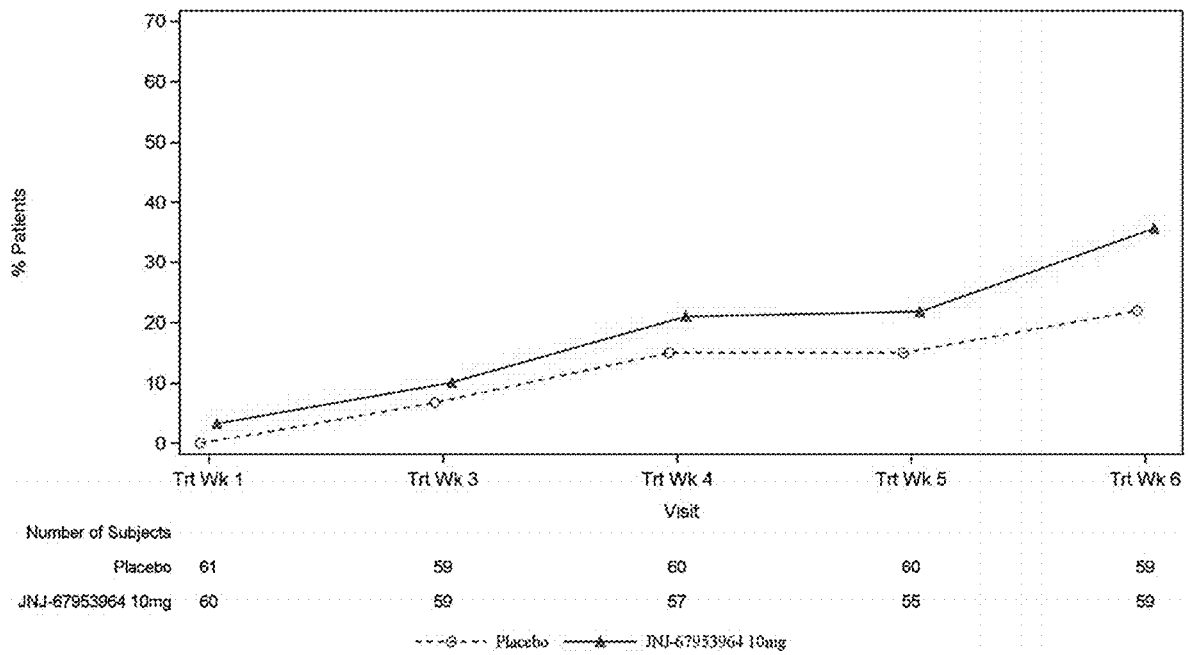
FIG. 10 is a line graph showing MADRS total score: percentage of responders (≥30% improvement from baseline) during the treatment period for the eITT analysis set.
Figure 11:
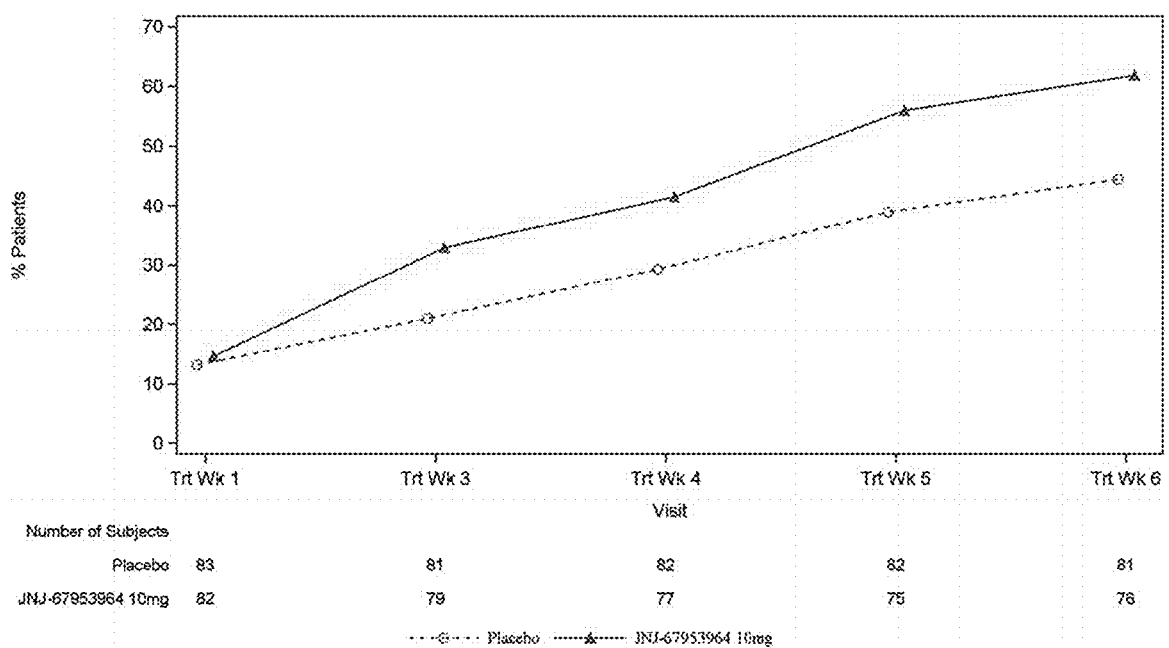
FIG. 11 is a line graph showing MADRS total score: percentage of responders (≥30% improvement from baseline) during the treatment period for the fITT analysis set.
Figure 12:
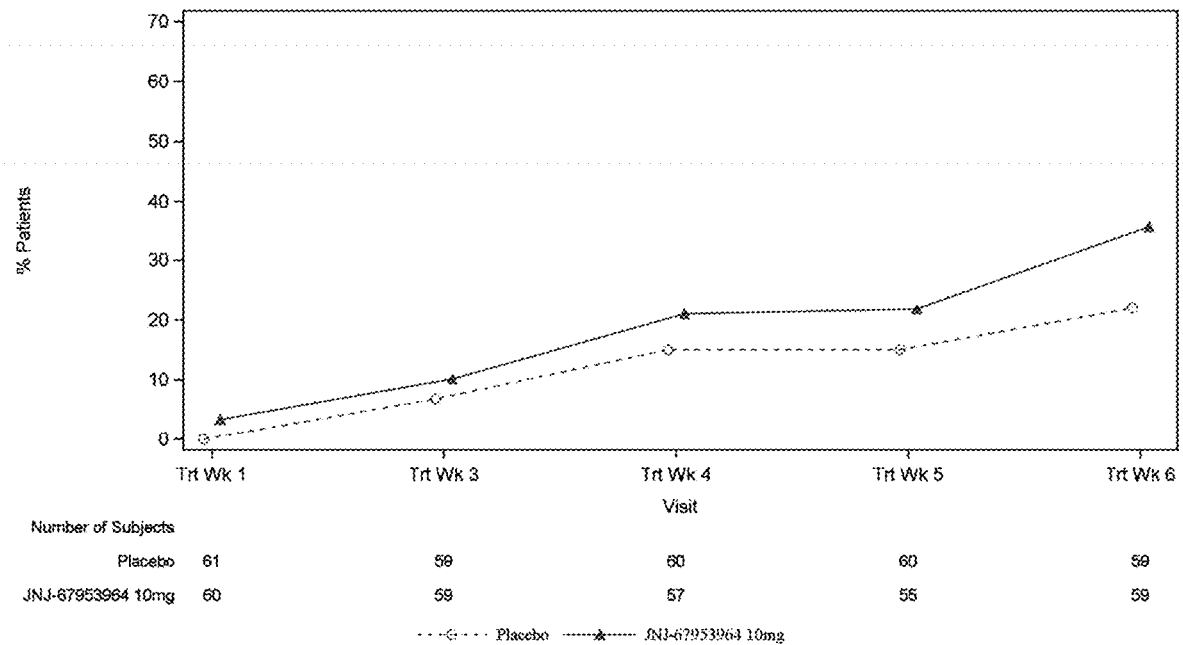
FIG. 12 is a line graph showing MADRS total score: percentage of responders (≥50% improvement from baseline) during the treatment period for the eITT analysis set.
Figure 13:
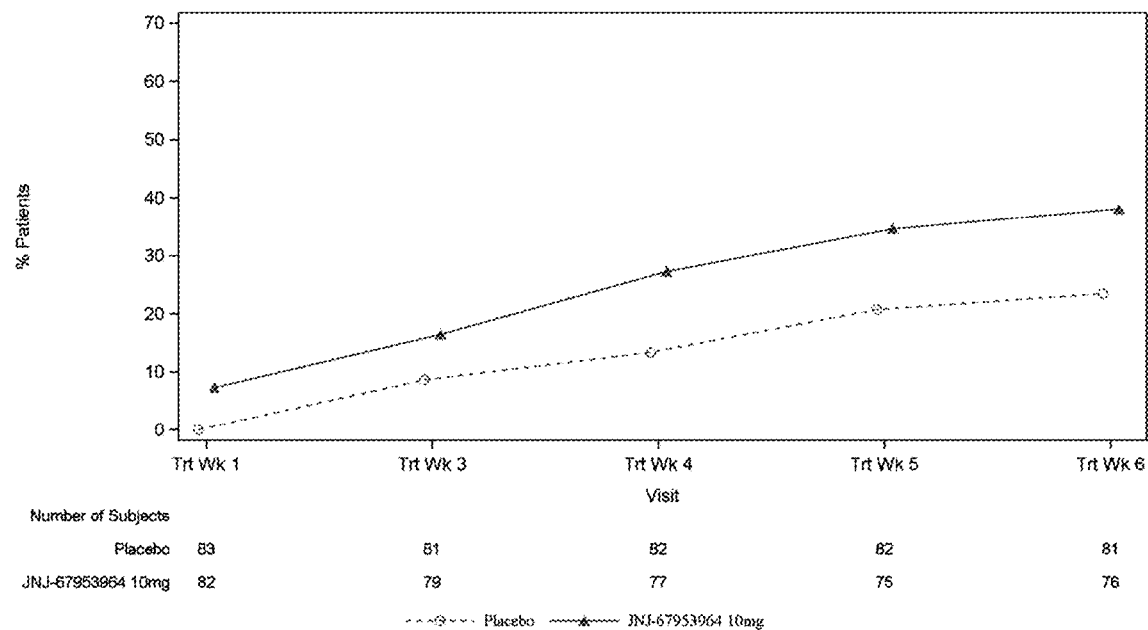
FIG. 13 is a line graph showing MADRS total score: percentage of responders (≥50% improvement from baseline) during the treatment period for the fITT analysis set.

At Treatment Week 6 the percentage of subjects with MADRS remission (MADRS total score≤10) in the eITT population was 16.9% for aticaprant and 16.9% for placebo. Treatment week 6 remission rates in fITT population were 31.2% for aticaprant and 22.2% for placebo. For both populations (eITT and fITT), no significant treatment differences were detected at treatment week 6 using Chi-square test (2-sided p=0.999 and p=0.203, respectively). See, FIGS. 8 and 9.

MADRS Response Rates (at Least 30% Improvement) Over Treatment Period

The percentage of subjects with ≥30% improvement in MADRS total score at treatment week 6 in the eITT population was 57.6% for aticaprant and 45.8% for placebo. Treatment week 6 response rates in fITT population were 61.8% for aticaprant and for 44.4% placebo. For both populations, treatment differences at Treatment Week 6 were significant at 20% 2-sided significance level (Chi-square test: p=0.197 for eITT and p=0.029 for fITT).

MADRS Response Rates (at Least 50% Improvement) Over Treatment Period

The percentage of subjects with ≥50% improvement in MADRS total score at treatment week 6 in the eITT population was 35.6% for aticaprant and 22.0% for placebo. Treatment week 6 response rates in fITT population were 38.2% for Aticaprant and 23.5% for placebo. For both populations, treatment differences at treatment week 6 were significant at 20% 2-sided significance level (Chi-square test: p=0.104 for eITT and p=0.046 for fITT). See, Table 10 and FIGS. 10-13.

TABLE 10

Change from Treatment Baseline in MADRS Total Score at Treatment Week 6 in Both Responders and Non-Responders during Placebo Lead-in Period

| End point values | Placebo | aticaprant 10 milligrams (mg) |
|---|---|---|
| Number of subjects analyzed | 81 | 77 |
| Units: score on a scale | | |
| Measure Type: Least Squares Mean (Standard Error) | −6.5 ± 0.78 | −9.6 ± 0.79 |
| P-value | | =0.0017 |
| Parameter type | | Least Squares Mean Difference |
| Point estimate | | −3.1 |
| Confidence interval | | |
| level | | 80% |
| sides | | 1-Sided |
| lower limit | | — |
| upper limit | | −2.21 |
| Variability estimate | | Standard Error of the mean |
| Dispersion value | | 1.05 |

Changes in SHAPS Total Score from Treatment Baseline to Treatment Week 6
Enriched ITT Analysis Set In eITT population, in a subgroup of subjects with high anhedonia level (baseline SHAPS total score≥38), larger differences between aticaprant placebo at Treatment Week 6 were observed than in subjects with low anhedonia level (20≤baseline SHAPS total score<38). The effect size was 0.38 and 0.11, respectively.

Figure 14:
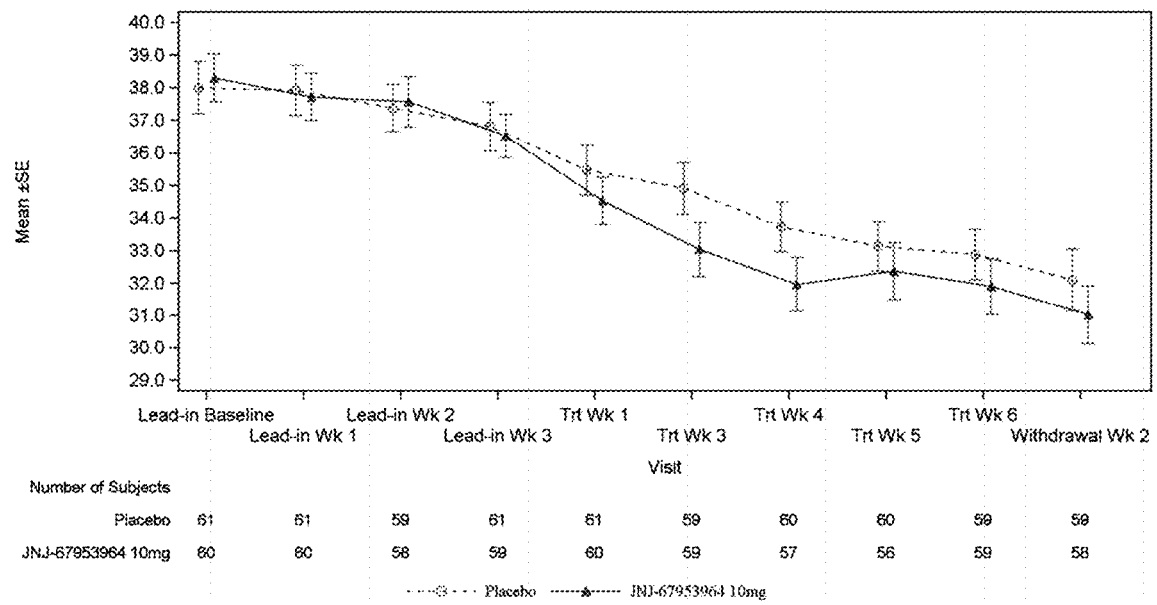
FIG. 14 is a line graph showing SHAPS total score: mean values (±SE) over time for the eITT analysis set.
Figure 23:
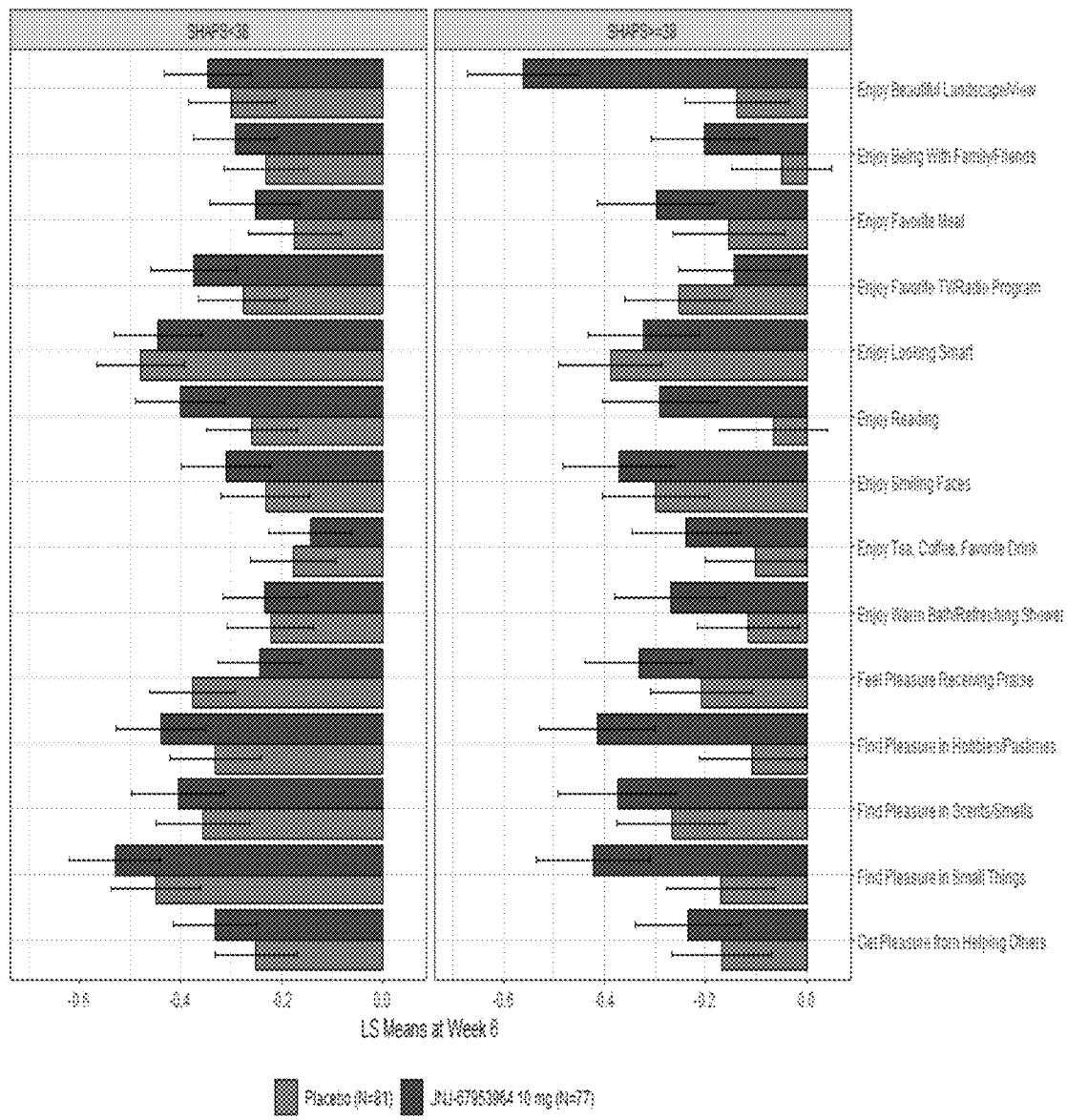
FIG. 23 is a bar graph showing the SHAPS items: LS means for change from baseline at week 6 by baseline SHAPS total score for the fITT analysis set. In this figure and going from top to bottom, the bars alternatively refer to placebo or aticaprant. For example, the first bar refers to aticaprant, the second bar refers to placebo, the third bar refers to aticaprant, etc.
Figure 24:
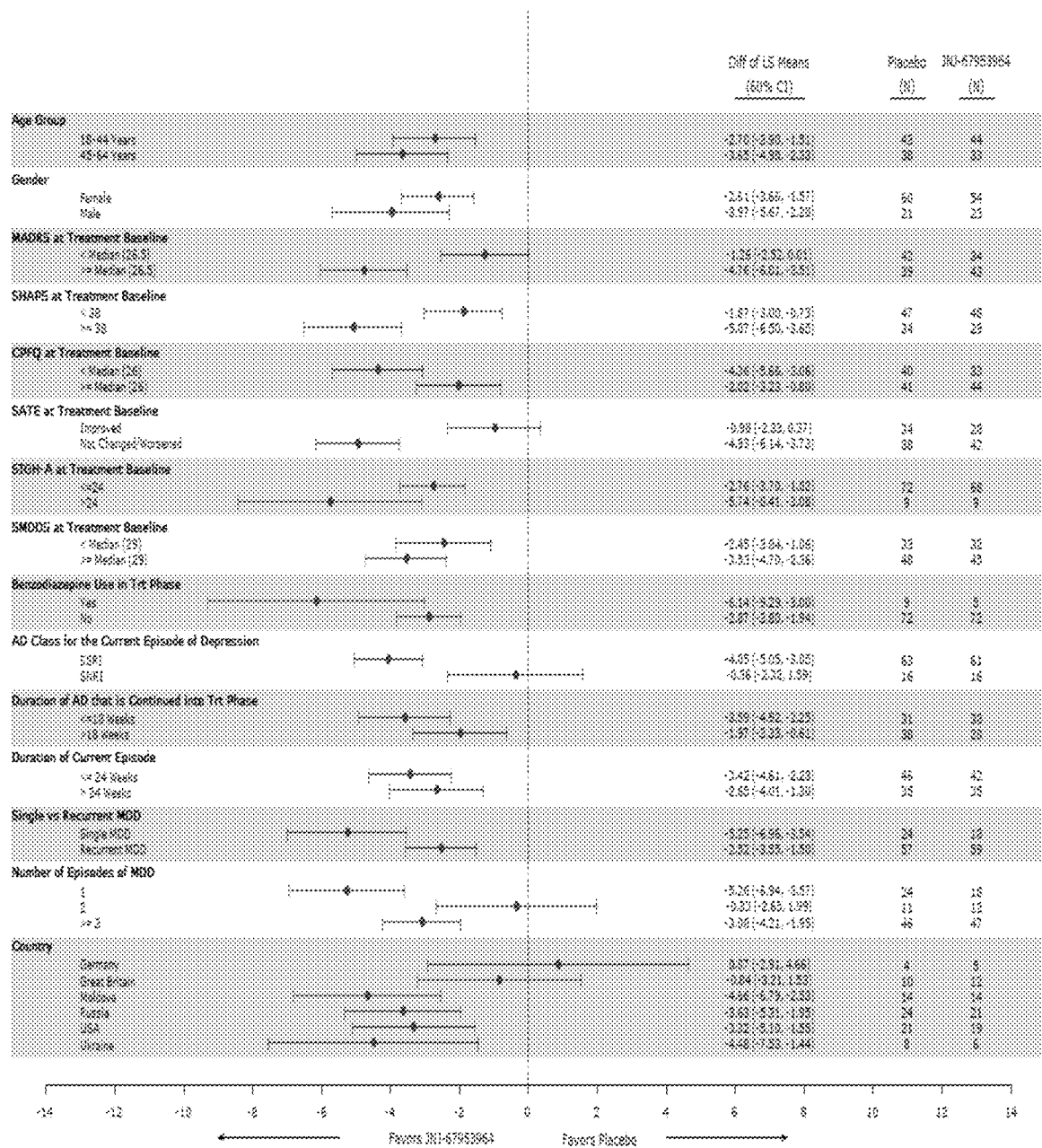
FIG. 24 is a plot showing MADRS total score: difference of LSMeans (60% at Weeks 6 by different subgroups for the fITT analysis set. In this plot, <17 indicates mild severity; 18-24 indicates mild to moderate severity, and 25-30 indicates moderate to severe.

The mean (SD) SHAPS total score at treatment baseline was 36.6 (5.45), ranging from 20 to 50. The mean change from treatment baseline (SD) in SHAPS total score at treatment week 6 was −4.6 (6.23) for aticaprant and −4.2 (5.04) for placebo. The observed effect size was 0.07. See, Table 11 and FIGS. 14 and 23.

TABLE 11

SHAPS Total Score: Mean Changes to Placebo During the Treatment Period; eITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 1 | | | | | |
| Placebo | 61 | −1.3 (3.17) | | | |
| aticaprant | 60 | −1.9 (4.30) | −0.6 (3.77) | [−1.7, 0.6] | −0.15 |
| Treatment Week 3 | | | | | |
| Placebo | 59 | −2.2 (4.65) | | | |
| aticaprant | 59 | −3.4 (5.25) | −1.2 (4.96) | [−2.8, 0.3] | −0.25 |
| Treatment Week 4 | | | | | |
| Placebo | 60 | −3.3 (4.47) | | | |
| aticaprant | 57 | −4.5 (5.89) | −1.2 (5.21) | [−2.8, 0.4] | −0.23 |
| Treatment Week 5 | | | | | |
| Placebo | 60 | −3.9 (4.88) | | | |
| aticaprant | 56 | −4.3 (6.07) | −0.4 (5.49) | [−2.1, 1.3] | −0.08 |
| Treatment Week 6 | | | | | |
| Placebo | 59 | −4.2 (5.04) | | | |
| aticaprant | 59 | −4.6 (6.23) | −0.4 (5.66) | [−2.1, 1.3] | −0.07 |

Negative change from baseline indicates improvement. Negative change to Placebo indicates favorable aticaprant effect. Negative effect size favors aticaprant; positive effect size favors Placebo.

Figure 4:
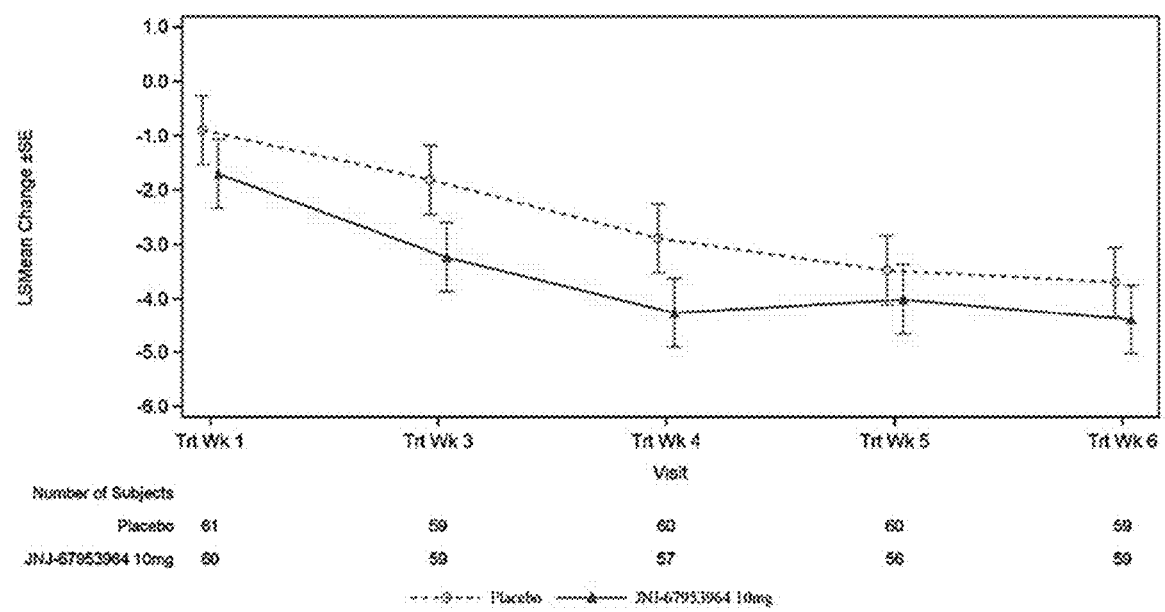
FIG. 4 is a line graph showing SHAPS (Snaith-Hamilton Pleasure Scale) total score: least squares mean changes from baseline (±SE) during the treatment period for the eITT analysis set.
Figure 15:
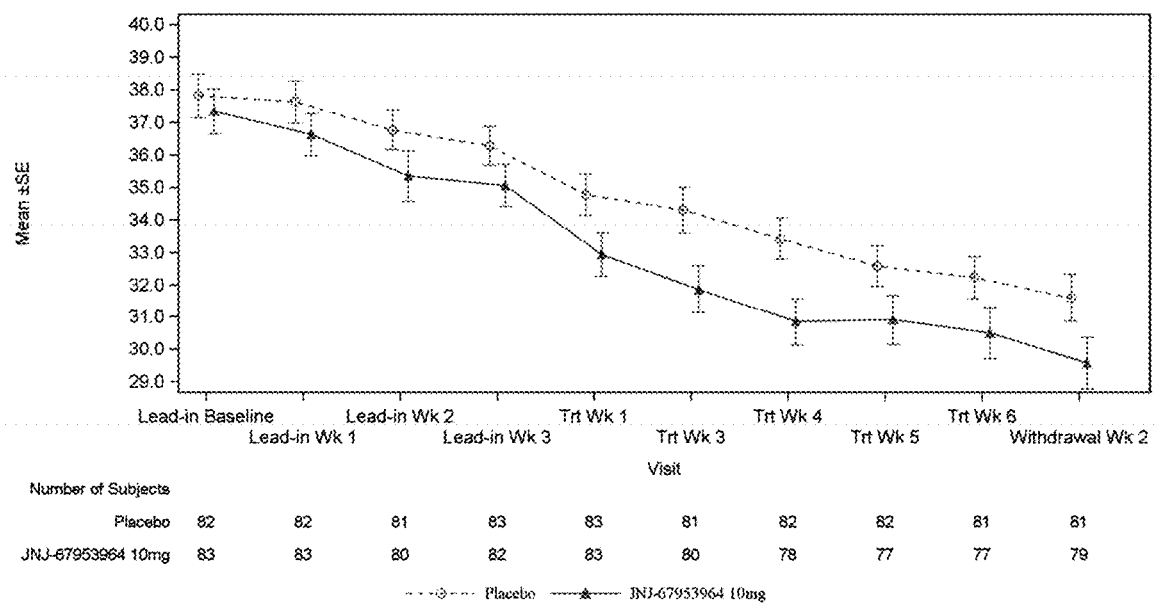
FIG. 15 is a line graph showing SHAPS total score: mean values (±SE) over time for the fITT analysis set.

Changes in SHAPS total score were analyzed with the same MMRM model used for MADRS total score. The estimated LS Mean difference with 80% 2-sided CI at treatment week 6 between aticaprant and placebo was −0.7 [−1.81, 0.41]. See, FIG. 4 and Tables 12 and 13 and FIG. 15. The corresponding p-value was 0.419.

TABLE 12

SHAPS Total Score: MMRM Results - Estimated LS Means and Comparison versus Placebo; eITT Analysis Set

| Analysis Visit Treatment | N | Mean (SD) | Mean (SD) | LSMean (SE) | Change from Baseline LSMean Difference (SE)\ Treatment Placebo | 60% Confidence Interval on Difference | p-value[a] |
|---|---|---|---|---|---|---|---|
| Treatment Week 1 | | | | | | | |
| Placebo | 61 | 35.5 (6.00) | −1.3 (3.17) | −0.9 (0.63) | | | |
| aticaprant | 60 | 34.5 (5.63) | −1.9 (4.30) | −1.7 (0.64) | −0.8 (0.86) | [−1.90, 0.31] | 0.3542 |
| Treatment Week 3 | | | | | | | |
| Placebo | 59 | 34.9 (6.09) | −2.2 (4.65) | −1.8 (0.64) | | | |
| aticaprant | 59 | 33.0 (6.39) | −3.4 (5.25) | −3.2 (0.64) | −1.4 (0.86) | [−2.53, −0.31] | 0.1005 |
| Treatment Week 4 | | | | | | | |
| Placebo | 60 | 33.7 (5.89) | −3.3 (4.47) | −2.9 (0.63) | | | |
| aticaprant | 57 | 32.0 (6.24) | −4.5 (5.89) | −4.3 (0.64) | −1.4 (0.86) | [−2.48, −0.26] | 0.1131 |
| Treatment Week 5 | | | | | | | |
| Placebo | 60 | 33.1 (5.88) | −3.9 (4.88) | −3.5 (0.64) | | | |
| aticaprant | 56 | 32.4 (6.61) | −4.3 (6.07) | −4.0 (0.64) | −0.5 (0.87) | [−1.65, 0.57] | 0.5332 |

TABLE 12-continued

SHAPS Total Score: MMRM Results - Estimated LS Means and Comparison versus Placebo; eITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| | | | | Change from Baseline | | | |
| | | | | Treatment Week 6 | | | |
| Placebo | 59 | 32.9 (6.04) | −4.2 (5.04) | −3.7 (0.64) | | | |
| aticaprant | 59 | 31.9 (6.60) | −4.6 (6.23) | −4.4 (0.64) | −0.7 (0.87) | [−1.81, 0.41] | 0.4188 |

[a] two-sided test for no difference between treatments from a MMRM model with subject as random effect; country, treatment, time and time-by-treatment interaction as factors; and baseline SHAPS total score as continuous covariate. An AR(1) variance-covariance matrix was employed.

TABLE 13

SHAPS Total Score: MMRM Results - Estimated LS Means and Comparison versus Placebo; fITT Analysis Set

| Analysis Visit Treatment | N | Mean (SD) | Mean (SD) | LSMean (SE) | LSMean Difference (SE)\ Treatment Placebo | 60% Confidence Interval on Difference | p-value[a] |
|---|---|---|---|---|---|---|---|
| | | | | Change from Baseline | | | |
| | | | | Treatment Week 1 | | | |
| Placebo | 83 | 34.8 (5.86) | −1.5 (3.57) | −1.0 (0.54) | | | |
| aticaprant | 83 | 32.9 (6.09) | −2.0 (4.05) | −1.9 (0.54) | −1.0 (0.72) | [−1.88, −0.02] | 0.1888 |
| | | | | Treatment Week 3 | | | |
| Placebo | 81 | 34.3 (6.36) | −2.2 (5.11) | −1.7 (0.54) | | | |
| aticaprant | 80 | 31.9 (6.54) | −3.2 (5.07) | −3.1 (0.54) | −1.4 (0.73) | [−2.32, −0.45] | 0.0580 |
| | | | | Treatment Week 4 | | | |
| Placebo | 82 | 33.4 (5.70) | −3.0 (4.41) | −2.5 (0.54) | | | |
| aticaprant | 78 | 30.8 (6.37) | −4.2 (5.70) | −4.1 (0.55) | −1.6 (0.73) | [−2.51, −0.63] | 0.0321 |
| | | | | Treatment Week 5 | | | |
| Placebo | 82 | 32.6 (5.63) | −3.8 (4.76) | −3.3 (0.55) | | | |
| aticaprant | 77 | 30.9 (6.76) | −4.3 (5.70) | −4.1 (0.55) | −0.8 (0.73) | [−1.71, 0.17] | 0.2912 |
| | | | | Treatment Week 6 | | | |
| Placebo | 81 | 32.2 (5.81) | −4.2 (4.98) | −3.7 (0.55) | | | |
| aticaprant | 77 | 30.5 (6.98) | −4.7 (5.91) | −4.5 (0.55) | −0.8 (0.73) | [−1.79, 0.10] | 0.2503 |

Figure 5:
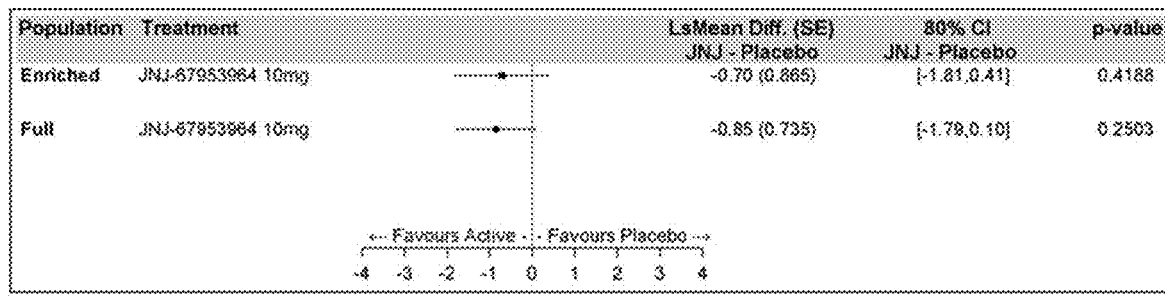
FIG. 5 is a plot showing SHAPS total score changes at treatment week 6 for enriched and full population: MMRM (Mixed-effects Model for Repeated Measures) Results—estimated LSMeans and comparison versus placebo

[a] two-sided test for no difference between treatments from a MMRM model with subject as random effect; country, treatment, time and time-by-treatment interaction as factors; and baseline SHAPS total score as continuous covariate. An AR(1) variance-covariance matrix was employed The estimated LS mean differences with 80% 2-sided CI at treatment week 6 between aticaprant and placebo was −0.8 [−1.79, 0.10]. The corresponding p-value was 0.250. See, FIGS. 4 and 5.

Full ITT Analysis Set

Similar trend was observed in fITT population and differences were larger in magnitude than those observed in eITT population. The effect size was 0.51 and 0.29, respectively. The mean (SD) baseline SHAPS total score at treatment baseline was 35.6 (5.67), ranging from 14 to 50. The mean changes from treatment baseline in SHAPS total score at treatment week 6 for fITT population were similar to changes in eITT: −4.7 (5.91) for aticaprant and −4.2 (4.98) for placebo. The observed effect size was 0.08. See, Table 14.

TABLE 14

SHAPS Total Score: Mean Changes to Placebo During the Treatment Period; fITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| | | Treatment Week 1 | | | |
| Placebo | 83 | −1.5 (3.57) | | | |
| aticaprant | 83 | −2.0 (4.05) | −0.6 (3.82) | [−1.5, 0.4] | −0.15 |
| | | Treatment Week 3 | | | |
| Placebo | 81 | −2.2 (5.11) | | | |
| aticaprant | 80 | −3.2 (5.07) | −1.0 (5.09) | [−2.4, 0.3] | −0.20 |

TABLE 14-continued

SHAPS Total Score: Mean Changes to Placebo During the Treatment Period; fITT Analysis Set

| Analysis Visit Treatment | N | Mean Change from Baseline (SD) | Mean Change to Placebo (SD pooled) | 90% CI for Mean Change to Placebo | Effect Size |
|---|---|---|---|---|---|
| Treatment Week 4 | | | | | |
| Placebo | 82 | −3.0 (4.41) | | | |
| aticaprant | 78 | −4.2 (5.70) | −1.2 (5.08) | [−2.5, 0.1] | −0.23 |
| Treatment Week 5 | | | | | |
| Placebo | 82 | −3.8 (4.76) | | | |
| aticaprant | 77 | −4.3 (5.70) | −0.5 (5.24) | [−1.8, 0.9] | −0.09 |
| Treatment Week 6 | | | | | |
| Placebo | 81 | −4.2 (4.98) | | | |
| aticaprant | 77 | −4.7 (5.91) | −0.5 (5.45) | [−1.9, 1.0] | −0.08 |

Negative change from baseline indicates improvement. Negative change to Placebo indicates favorable aticaprant effect. Negative effect size favors aticaprant; positive effect size favors Placebo.

Changes in MADRS Total Score from Treatment Baseline to Treatment Week 6 by Anhedonia Level at Baseline Enriched ITT Analysis Set In subgroup of subjects with high anhedonia level (SHAPS total score≥38) at treatment baseline, n=53, larger differences between aticaprant and placebo at treatment Week 6 were observed than in subjects with low anhedonia level (20≤baseline SHAPS total score<38), n=65: −3.4 with 90% 2-sided CI of [−7.5, 0.7] and −0.9 with 90% 2-sided CI of [−4.2, 2.5], respectively (Table 15). The observed effect size was 0.38 and 0.11, respectively.

TABLE 15

MADRS (Montgomery-Åsberg Depression Rating Scale) Total Score: Mean Changes to Placebo During the Treatment Period by Anhedonia Level at Treatment Baseline; eITT Analysis Set

| Analysis Visit Treatment | N | Mean Change from Baseline (SD) | Mean Change to Placebo (SD pooled) | 90% CI for Mean Change to Placebo | Effect size |
|---|---|---|---|---|---|
| Low anhedonia Treatment Week 1 | | | | | |
| Placebo | 34 | −1.8 (3.43) | | | |
| aticaprant | 34 | −2.3 (5.03) | −0.5 (4.30) | [−2.2, 1.2] | −0.12 |
| Treatment Week 3 | | | | | |
| Placebo | 32 | −4.8 (5.70) | | | |
| aticaprant | 33 | −4.9 (5.99) | −0.1 (5.85) | [−2.5, 2.4] | −0.01 |
| Treatment Week 4 | | | | | |
| Placebo | 33 | −6.5 (6.16) | | | |
| aticaprant | 32 | −6.4 (7.40) | 0.0 (6.80) | [−2.8, 2.9] | 0.01 |
| Treatment Week 5 | | | | | |
| Placebo | 33 | −7.6 (6.80) | | | |
| aticaprant | 29 | −7.2 (6.46) | 0.3 (6.65) | [−2.5, 3.2] | 0.05 |
| Treatment Week 6 | | | | | |
| Placebo | 32 | −8.3 (8.25) | | | |
| aticaprant | 33 | −9.2 (8.01) | −0.9 (8.13) | [−4.2, 2.5] | −0.11 |
| High anhedonia Treatment Week 1 | | | | | |
| Placebo | 27 | −2.7 (4.08) | | | |
| aticaprant | 26 | −4.6 (5.25) | −1.8 (4.69) | [−4.0, 0.3] | −0.39 |
| Treatment Week 3 | | | | | |
| Placebo | 27 | −3.6 (6.35) | | | |
| aticaprant | 26 | −6.7 (6.83) | −3.0 (6.59) | [−6.1, 0.0] | −0.46 |
| Treatment Week 4 | | | | | |
| Placebo | 27 | −6.3 (7.34) | | | |
| aticaprant | 25 | −8.5 (7.26) | −2.2 (7.30) | [−5.6, 1.2] | −0.30 |
| Treatment Week 5 | | | | | |
| Placebo | 27 | −7.1 (7.67) | | | |
| aticaprant | 26 | −9.7 (8.18) | −2.6 (7.93) | [−6.3, 1.0] | −0.33 |
| Treatment Week 6 | | | | | |
| Placebo | 27 | −8.1 (9.01) | | | |
| aticaprant | 26 | −11.5 (8.95) | −3.4 (8.98) | [−7.5, 0.7] | −0.38 |

Low Anhedonia level (SHAPS Total Score at Treatment Baseline >=20 and <38), High Anhedonia level (SHAPS Total Score at Treatment Baseline >=38). The MADRS Total Score ranges from 0 to 60, with higher scores indicating greater severity of depression.

Full ITT Analysis Set

A similar trend was observed in fITT population. The differences were larger in magnitude compared to eITT population: −4.6 with 90% 2-sided CI of [−8.4, −0.8] for subjects with high anhedonia level (n=63) and −2.3 with 90% 2-sided CI of [−5.0, 0.4] for subjects with low anhedonia level (n=94). See, Table 16. The observed effect size was 0.51 and 0.29, respectively.

TABLE 16

MADRS (Montgomery-Åsberg Depression Rating Scale) Total Score: Mean Changes to Placebo During the Treatment Period by Anhedonia Level at Treatment Baseline; fITT Analysis Set

| Analysis Visit Treatment | N | Mean Change from Baseline (SD) | Mean Change to Placebo (SD pooled) | 90% CI for Mean Change to Placebo | Effect size |
|---|---|---|---|---|---|
| Low anhedonia Treatment Week 1 | | | | | |
| Placebo | 49 | −1.3 (4.17) | | | |
| aticaprant | 52 | −2.4 (4.59) | −1.0 (4.39) | [−2.5, 0.4] | −0.24 |
| Treatment Week 3 | | | | | |
| Placebo | 47 | −3.6 (6.04) | | | |
| aticaprant | 49 | −4.1 (6.67) | −0.5 (6.37) | [−2.7, 1.7] | −0.08 |
| Treatment Week 4 | | | | | |
| Placebo | 48 | −4.9 (6.53) | | | |
| aticaprant | 48 | −6.4 (6.77) | −1.5 (6.65) | [−3.8, 0.8] | −0.23 |
| Treatment Week 5 | | | | | |
| Placebo | 48 | −6.6 (6.82) | | | |
| aticaprant | 45 | −7.3 (6.90) | −0.7 (6.86) | [−3.1, 1.7] | −0.10 |
| Treatment Week 6 | | | | | |
| Placebo | 47 | −6.5 (8.11) | | | |
| aticaprant | 47 | −8.8 (7.48) | −2.3 (7.80) | [−5.0, 0.4] | −0.29 |
| High anhedonia Treatment Week 1 | | | | | |
| Placebo | 34 | −2.4 (3.71) | | | |
| aticaprant | 30 | −4.4 (5.04) | −2.0 (4.38) | [−3.8, −0.1] | −0.45 |
| Treatment Week 3 | | | | | |
| Placebo | 34 | −3.1 (7.17) | | | |
| aticaprant | 30 | −6.9 (6.66) | −3.8 (6.94) | [−6.7, −0.9] | −0.54 |

TABLE 16-continued

MADRS (Montgomery-Åsberg Depression Rating Scale) Total Score: Mean Changes to Placebo During the Treatment Period by Anhedonia Level at Treatment Baseline; fITT Analysis Set

| Analysis Visit Treatment | N | Mean Change from Baseline (SD) | Mean Change to Placebo (SD pooled) | 90% CI for Mean Change to Placebo | Effect size |
|---|---|---|---|---|---|
| Treatment Week 4 | | | | | |
| Placebo | 34 | −4.8 (7.75) | | | |
| aticaprant | 29 | −8.6 (7.32) | −3.8 (7.56) | [−7.0, −0.6] | −0.50 |
| Treatment Week 5 | | | | | |
| Placebo | 34 | −6.2 (7.72) | | | |
| aticaprant | 30 | −10.2 (8.04) | −4.0 (7.87) | [−7.3, −0.7] | −0.51 |
| Treatment Week 6 | | | | | |
| Placebo | 34 | −6.8 (9.30) | | | |
| aticaprant | 29 | −11.3 (8.69) | −4.6 (9.03) | [−8.4, −0.8] | −0.51 |

Low Anhedonia level (SHAPS Total Score at Treatment Baseline >=20 and <38), High Anhedonia level (SHAPS Total Score at Treatment Baseline >=38). The MADRS Total Score ranges from 0 to 60, with higher scores indicating greater severity of depression.

This data illustrates that segmentation into high vs low anhedonia had a benefit for treating MDD: higher treatment effect for Aticaprant. Further, the placebo response was lower in patients with high anhedonia, as compared to low anhedonia. I'm attaching a plot that I created based on this same data which illustrates.

Change from Treatment Baseline in CGI-S Total Score at Treatment

TABLE 17

Change from Treatment Baseline in CGI-S Total Score at Treatment

| End point values | Placebo | aticaprant 10 milligrams (mg) |
|---|---|---|
| Number of subjects analyzed | 59 | 59 |
| Units: Scores on a scale | | |
| Measure Type: Arithmetic Mean (SD) | −0.76 ± 0.858 | −0.92 ± 1.039 |

Change from Treatment Baseline in SMDDS Total Score at Treatment Week 6

TABLE 18

Change from Treatment Baseline in SMDDS Total Score at Treatment Week

| End point values | Placebo | aticaprant 10 milligrams (mg) |
|---|---|---|
| Number of subjects analyzed | 59 | 59 |
| Units: Scores on a scale | | |
| Measure Type: Arithmetic Mean (SD) | −8.49 ± 9.567 | −8.03 ± 9.957 |

Number of Subjects with SATE Score at Treatment Week 6

TABLE 19

Number of Subjects with SATE Score at Treatment Week 6

| End point values | Placebo | aticaprant 10 milligrams (mg) |
|---|---|---|
| Number of subjects analyzed | 61 | 60 |
| Units: subjects | | |
| Overall Depression (Got worse) (n = 40, 30) | 1 | 0 |
| Overall Depression (Not changed) (n = 40, 30) | 12 | 9 |
| Overall Depression (Improved) (n = 40, 30) | 27 | 21 |
| Depression Worsened (Slightly worse) (n = 1, 0) | 1 | 0 |
| Depression Worsened (Much worse) (n = 1, 0) | 0 | 0 |
| Depression Worsened (Very much worse) (n = 1, 0) | 0 | 0 |
| Depression Slightly improved (n = 27, 21) | 13 | 15 |
| Depression Much improved (n = 27, 21) | 11 | 6 |
| Depression Very Much Improved (n = 27, 21) | 3 | 0 |

Change from Treatment Baseline in HAM-A6 Total Score at Treatment Week 6

TABLE 20

Change from Treatment Baseline in HAM-A6 Total Score at Treatment Week

| End point values | Placebo | aticaprant 10 milligrams (mg) |
|---|---|---|
| Number of subjects analyzed | 59 | 59 |
| Units: scores on a scale | | |
| Measure Type: Arithmetic Mean (SD) | −2.19 ± 2.837 | −2.73 ± 2.651 |

These data show a greater improvement in HAMA6 score in aticaprant treated patients vs. placebo.

Change from Treatment Baseline in Structured Interview Guide for the SIGH-A Score at Treatment Week 6

TABLE 21

Change from Treatment Baseline in Structured Interview Guide for the SIGH-A Score at Treatment Week 6

| End point values | Placebo | aticaprant 10 milligrams (mg) |
|---|---|---|
| Number of subjects analyzed | 59 | 59 |
| Units: scores on a scale | | |
| Measure Type: Arithmetic Mean (SD) | −5.37 ± 6.549 | −5.85 ± 5.369 |

Maximum Plasma Concentration ($C_{max}$) of Aticaprant $C_{max}$ is defined as maximum plasma concentration of aticaprant. The eITT population included all enrolled lead-in placebo non-responders who were randomized into a treatment period, received at least 1 dose of study medication, and had at least 1 post-baseline MADRS assessment during the treatment period. Here 'N' (number of subjects analyzed) includes the number of subjects evaluable for this endpoint. Here 'n' (number analyzed) included all subjects evaluable for specified time point categories.

TABLE 22

$C_{max}$ of Aticaprant (10 mg)

Number of subjects analyzed 58
Units: nanograms per milliliter (ng/mL)
Measure Type: Arithmetic Mean (SD)

| | |
|---|---|
| Week 1 (n = 56) | 32.7 ± 10.9 |
| Week 3 (n = 56) | 33.5 ± 11.1 |
| Week 6 (n = 56) | 34.3 ± 11.1 |

No statistical analyses of this end point.

(iii) Safety Endpoints

Overall, in full safety analysis set 40/85 (47.1%) of subjects in the aticaprant group and 30/84 (35.7%) of subjects in the placebo group experienced at least one TEAE during the treatment period. See, Table 23.

TABLE 23

Overall Summary of Treatment-Emergent Adverse Events During the Treatment Period; Full Safety Analysis Set

| | Placebo (N = 84) n (%) | aticaprant 10 mg (N = 85) n (%) | Overall (N = 169) n (%) |
|---|---|---|---|
| Subjects with 1 or more TEAE | 30 (35.7) | 40 (47.1) | 70 (41.4) |
| Total subjects affected by non-serious adverse events | 9 (10.7%) | 23 (27.1%) | |
| Subjects with drug-related TEAE [a] | 13 (15.5) | 20 (23.5) | 33 (19.5) |
| Subjects with TEAE leading to death | 0 | 0 | 0 |
| Subjects with 1 or more serious TEAE | 1 (1.2) | 0 | 1 (0.6) |
| Subjects with TEAE leading to discontinuation of agent | 1 (1.2) | 1 (1.2) | 2 (1.2) |

[a] Drug relationships of possible, probable, and very likely are included in this category. Subjects are presented by the treatment received during the Treatment period.

The most common TEAEs during the treatment period were headache (experienced by 10/85 subjects—11.8% in the aticaprant group and by 6/84 subjects—7.1% in the placebo group) and diarrhea (experienced by 7/85 subjects—8.2% in the aticaprant group and by 2/84 subjects—2.4% in the placebo group). See, Table 24.

TABLE 24

Treatment-Emergent Adverse Events by Body System or Organ Class and Dictionary-Derived Term in >=5% of Subjects in Either Treatment Group During the Treatment Period; Full Safety Analysis Set

| Body System Preferred Term | Placebo (N = 84) n (%) | aticaprant 10 mg (N = 85) n (%) | Overall (N = 169) n (%) |
|---|---|---|---|
| Total no. Subjects with Adverse Events | 30 (36) | 40 (47) | 70 (41) |
| Infections And Infestations | 9 (11) | 13 (15) | 22 (13) |
| Nasopharyngitis | 2 (2) | 5 (6) | 7 (4) |
| Nervous System Disorders | 9 (11) | 13 (15) | 22 (13) |
| Headache | 6 (7) | 10 (12) | 16 (10) |
| Gastrointestinal Disorders | 9 (11) | 12 (14) | 21 (12) |
| Diarrhea | 2 (2) | 7 (8) | 9 (5) |
| Skin And Subcutaneous Tissue Disorders | 3 (4) | 6 (7) | 9 (5) |
| Pruritus | 0 | 5 (6) | 5 (3) |

Percentages calculated with the number of subjects in each group as denominator. Reported dictionary version: MedDRA 22.1. Subjects are presented by the treatment received during the Treatment period.

There were 2 subjects in total who discontinued during the treatment period due to treatment-emergent adverse events: 1 subject in the aticaprant 10 group due to diarrhea, nausea, vomiting and headache, and another subject in placebo group due to acute calculous cholecystitis.

Overall, 17/169 subjects experienced TEAEs of special interest during the treatment period: 13/85 (15.3%) in the aticaprant group and 4/84 (4.8%) in the placebo group. The most common treatment-emergent adverse events during the treatment phase were headache and diarrhea. The most common TEAE of special interest during the treatment period were diarrhea and pruritus (experienced by 5/85 subjects—5.9% in the aticaprant group and by 0/84 subjects in the placebo group). Further 1 patient in the placebo group (1.19%) experienced acute cholecystitis, as compared to 0 patients receiving aticaprant. See, Table 25.

TABLE 25

Treatment-Emergent Adverse Events of Special Interest During the Treatment Period; Full Safety Analysis Set

| Body System Preferred Term | Placebo (N = 84) n (%) | aticaprant 10 mg (N = 85) n (%) | Overall (N = 169) n (%) |
|---|---|---|---|
| Total no. Subjects with Adverse Events of Special Interest | 4 (4.8) | 13 (15.3) | 17 (10.1) |
| Gastrointestinal Disorders deaths causally related to treatment/all | 4 (4.8) | 9 (10.6) | 13 (7.7) |
| Diarrhea | 2 (2.4) | 7 (8.2) | 9 (5.3) |
| Abdominal Pain Upper | 2 (2.4) | 0 | 2 (1.2) |
| Dyspepsia | 1 (1.2) | 1 (1.2) | 2 (1.2) |
| Abdominal Pain | 0 | 1 (1.2) | 1 (0.6) |
| Skin And Subcutaneous Tissue Disorders | 0 | 5 (5.9) | 5 (3.0) |
| Pruritus | 0 | 5 (5.9) | 5 (3.0) |

Percentages calculated with the number of subjects in each group as denominator. Reported dictionary version: MedDRA 22.1. Subjects are presented by the treatment received during the Treatment period.

Two serious adverse events occurred. One subject in the placebo group experienced acute calculous cholecystitis during the treatment period and other subject suicidal ideation during the lead-in period. Both subjects discontinued due to these AEs.

No deaths were reported.

(iv) Anhedonia Analysis

Patients in the larger fITT group maintained baseline level of depression and anhedonia severity consistent with the eITT group. See, Tables 26-28.

TABLE 26

Frequency of Subjects with Anhedonia at Treatment Baseline; fITT Analysis Set

| | N | No Anhedonia (SHAPS Total Score < 20) Baseline/Day 22 | Anhedonia (SHAPS Total Score >= 20) |
|---|---|---|---|
| Placebo | 83 | 0 | 83 (100%) |
| aticaprant | 83 | 1 (1.2%) | 82 (98.8%) |
| Total | 166 | 1 (0.6%) | 165 (99.4%) |

Anhedonia classification is based on calculated SHAPS total score at Visit Day 22

Figure 16:
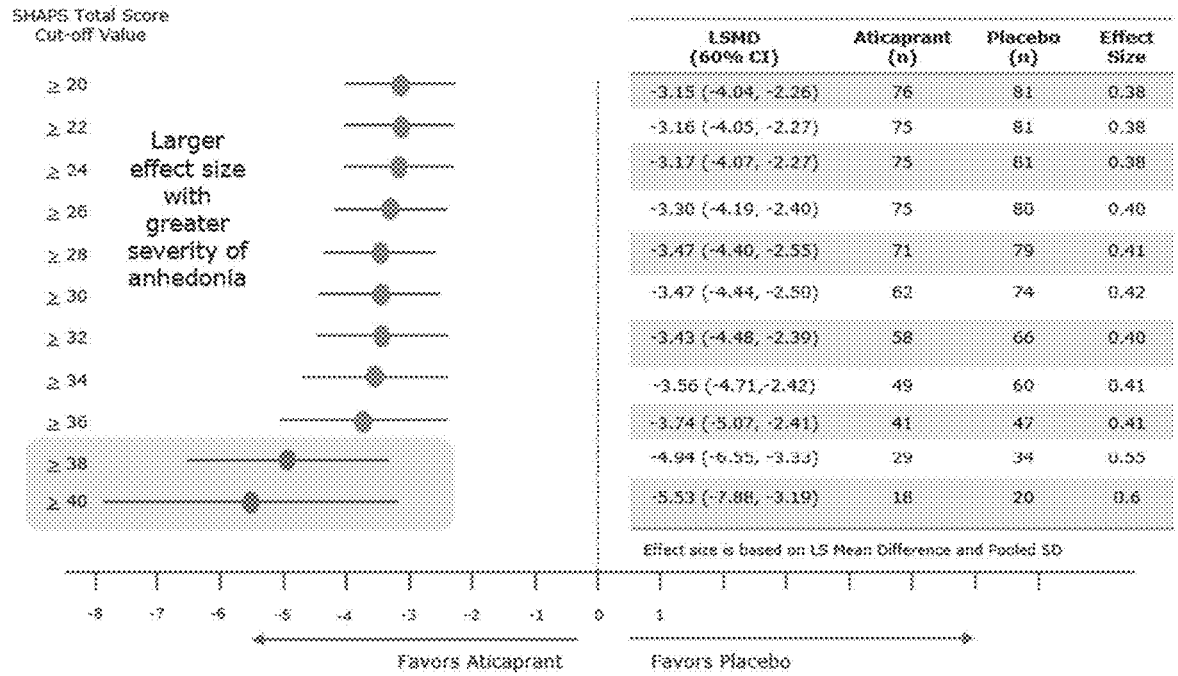
FIG. 16 illustrates the MADRS change from baseline by anhedonia severity.

The results illustrate that treatment effect is larger in patients with more anhedonia at baseline. See, FIG. 16.

TABLE 27

Frequency of Subjects with Different Level of Anhedonia at Treatment Baseline and Treatment Week 6; eITT Analysis Set

|  | N | No Anhedonia (SHAPS Total Score < 20) | Low Level of Anhedonia (20 <= SHAPS Total Score < 38) | High Level of Anhedonia (SHAPS Total Score >= 38) |
|---|---|---|---|---|
| Treatment Baseline | | | | |
| Placebo | 61 | 0 | 34 (55.74%) | 27 (44.26%) |
| aticaprant | 60 | 0 | 34 (56.67%) | 26 (43.33%) |
| Total | 121 | 0 | 68 (56.2%) | 53 (43.8%) |
| Treatment Week 6 | | | | |
| Placebo | 59 | 0 | 46 (77.97%) | 13 (22.03%) |
| aticaprant | 59 | 3 (5.08%) | 48 (81.36%) | 8 (13.56%) |
| Total | 118 | 3 (2.54%) | 94 (79.66%) | 21 (17.8%) |

Anhedonia classification is based on re-calculated SHAPS total score at analysis visits Treatment Baseline and Treatment Week 6.

TABLE 28

Frequency of Subjects with Different Level of Anhedonia at Treatment Baseline and Treatment Week 6; fITT Analysis Set

|  | N | No Anhedonia (SHAPS Total Score < 20) | Low Level of Anhedonia (20 >= SHAPS Total Score < 38) | High Level of Anhedonia (SHAPS Total Score >= 38) |
|---|---|---|---|---|
| Treatment Baseline | | | | |
| Placebo | 83 | 0 | 49 (59.04%) | 34 (40.96%) |
| aticaprant | 83 | 1 (1.2%) | 52 (62.65%) | 30 (36.14%) |
| Total | 166 | 1 (0.6%) | 101 (60.84%) | 64 (38.55%) |
| Treatment Week 6 | | | | |
| Placebo | 81 | 0 | 66 (81.48%) | 15 (18.52%) |
| aticaprant | 77 | 7 (9.09%) | 62 (80.52%) | 8 (10.39%) |
| Total | 158 | 7 (4.43%) | 128 (81.01%) | 23 (14.56%) |

Anhedonia classification is based on re-calculated SHAPS total score at analysis visits Treatment Baseline and Treatment Week 6.

Figure 17A:
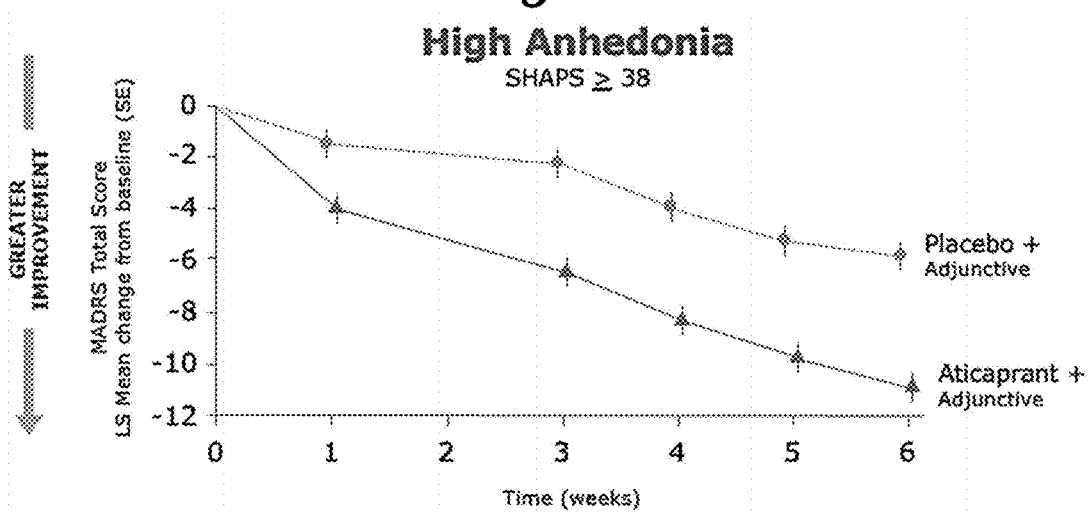
FIG. 17A is a line graph showing MADRS change from baseline for patients with high anhedonia, i.e., SHAPS≥38.
Figure 17B:
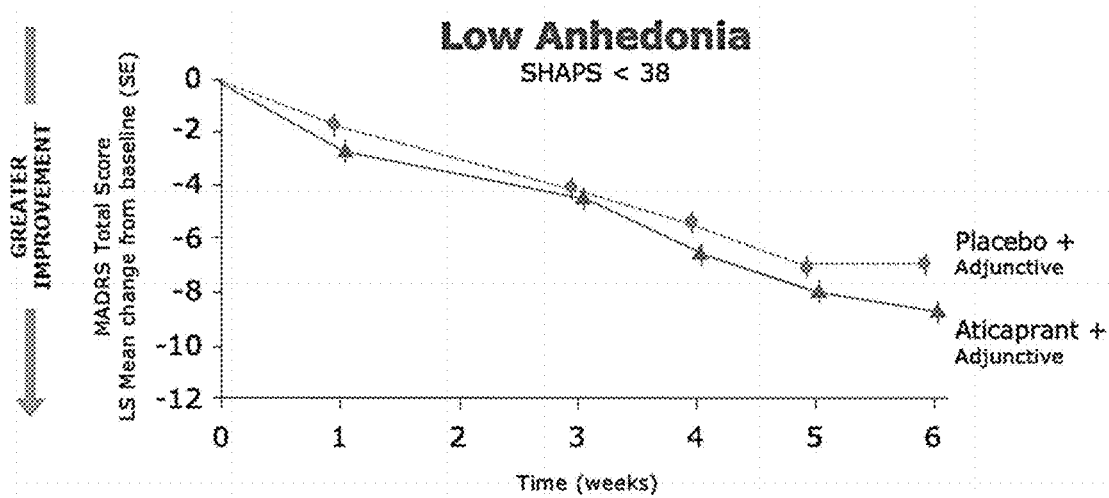
FIG. 17B is a line graph showing MADRS change from baseline for patients with low anhedonia, i.e., SHAPS<38.
Figure 18:
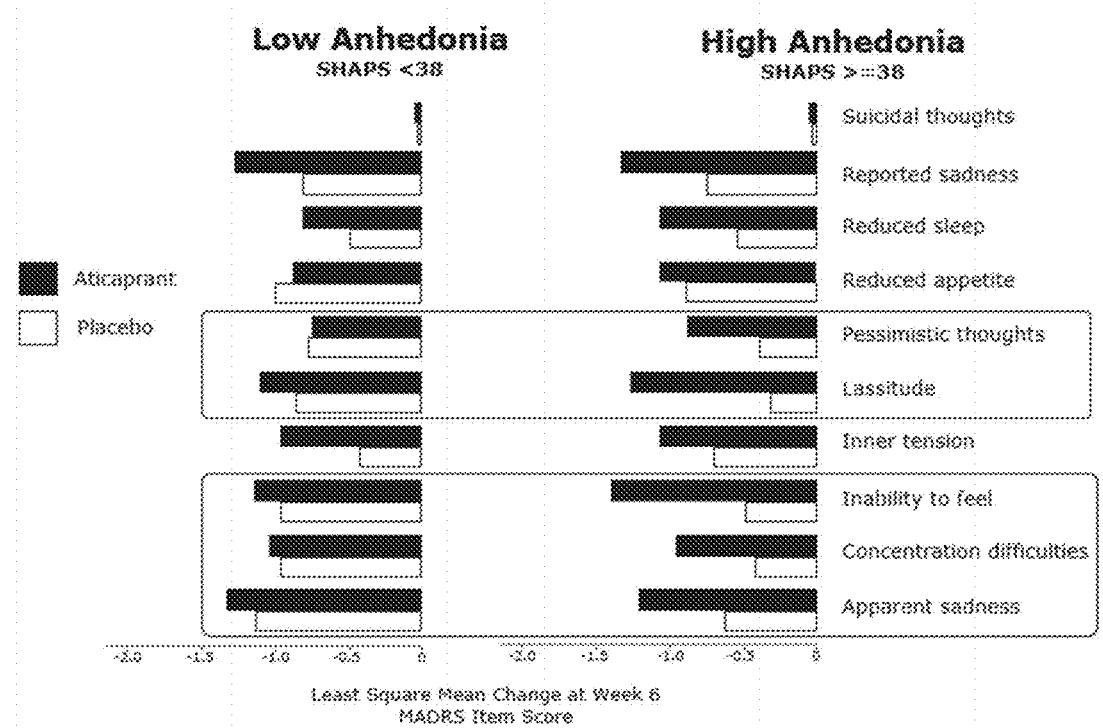
FIG. 18 is bar graph showing the comparison of MADRS in patients having low and high anhedonia.

The results illustrate that the treatment effect is larger in patients with more anhedonia at baseline. See, FIGS. 17A and 17B. In FIG. 17A, i.e., the high anhedonia group, the placebo+oral antidepressant group shows less placebo response as compared to the low anhedonia group in FIG. 17B. Similarly the treatment effect of the aticaprant+oral antidepressant group is higher in the high anhedonia group as compared to the low anhedonia group. Overall the effect size is larger at every single time point (from week 1 onwards) in the high anhedonia group. The LSMD in the high anhedonia group is more than double that of the low anhedonia group at week 6. Further, when looking at the symptom level, greater improvement in items related to anhedonia and dysphoria in subgroup with high anhedonia vs low anhedonia. See, FIG. 18.

(v) Weight Change

At the lead-in baseline timepoint, the mean weight for subjects in the placebo group was 76.17 kg compared to 78.66 in the aticaprant group. After 6 weeks in the double-blind treatment phase, the mean weight in the placebo group was 75.75 kg compared to 78.57 kg in the aticaprant group. This indicates that the weight in both groups remained relatively stable over the 6-week double blind treatment period. This is unexpected because other adjunctive treatments for MDD result in a mean weight increase. See, Thase M, et al. J Clin Psych. 2015: 76(9), 1224-1231; Thase, J Clin Psych. 2015, 76(9):1232-1240; El Khalili, Int J Neuropsychopharmacol. 2010, 13, 917-932; Marcus, J. Clin. Psychopharmacol. 2008, 28:156-165; Berman, J. Clin. Psychiatry 2007; 68:843-853; Berman, American College of Neuropsychopharmacology, 2008, Annual Meeting Abstracts (Scottsdale, Ariz, Dec. 7-11, 2008). Nashville, Tenn, ACNP, 2008; Earley, American College of Neuropsychopharmacology, 2007, Annual Meeting Abstracts (Boca Raton, Fla, Dec. 9-13, 2007). Nashville, TN, ACNP, 2007). See, Table 29.

TABLE 29

Mean weight by treatment group (kg)

|  | Placebo n = 84 | Aticaprant n = 85 |
|---|---|---|
| Screening, mean (SE) | 76.39 (1.61) | 78.42 (1.65) |
| Lead-in Baseline, mean (SE) | 76.17 (1.61) | 78.66 (1.65) |
| Withdrawal Baseline, mean (SE) | 75.75 (1.62) | 78.57 (1.71) |
| Absolute Change (Withdrawal – Lead-in) | –0.42 | –0.09 |
| Relative % Change | –0.55% | –0.11% |

(vi) Completion Rate

Patients who passed the screening phase entered a lead in phase followed by a double-blind phase. Patients who responded to placebo during the lead in phase were labelled as non-responders. Patients who did not respond to placebo were labelled as non-responders. The double-blind treatment phase then continued for an additional 6 weeks, after which patients entered a withdrawal period.

Of the 121 subjects in the enriched population (60 in aticaprant and 61 in placebo group), 117 (96.7%) completed the study. The overall completion rate for the full ITT analysis set is 95%. This contrasts with completion rates of approximately 85% for studies of adjunctive aripiprazole (Pae, CNS Drugs, 2011; 25, 109-127) and 45-62% for adjunctive quetiapine (El Khalili cited above). In total 4 subjects (3.3%) discontinued the study: 2 subjects in placebo and 2 subjects in aticaprant treatment group. See, Tables 30 and 31.

TABLE 30

Completion/Early Withdrawal Information; eITT Analysis Set

|  | Placebo (N = 61) | aticaprant 10 mg (N = 60) | Total (N = 121) |
|---|---|---|---|
| Subject Completed Treatment/Trial | | | |
| Completed | 59 (96.7%) | 58 (96.7%) | 117 (96.7%) |
| Withdrawn | 2 (3.3%) | 2 (3.3%) | 4 (3.3%) |
| Reason For Withdrawal/Termination | | | |
| Lack of Efficacy | 0 | 1 (1.7%) | 1 (0.8%) |
| Non-compliance with drug | 0 | 1 (1.7%) | 1 (0.8%) |
| Withdrawal by subject | 1 (1.6%) | 0 | 1 (0.8%) |
| Other | 1 (1.6%) | 0 | 1 (0.8%) |

Percentages calculated with the number of subjects in each group as denominator.

TABLE 31

Completion/Early Withdrawal Information; Full Safety Analysis Set

| | Placebo (N = 84) | aticaprant 10 mg (N = 85) | Total (N = 169) |
|---|---|---|---|
| Subject Completed Treatment/Trial | | | |
| Completed | 81 (96.4%) | 79 (92.9%) | 160 (94.7%) |
| Withdrawn | 3 (3.6%) | 6 (7.1%) | 9 (5.3%) |
| Reason For Withdrawal/Termination | | | |
| Adverse event | 1 (1.2%) | 1 (1.2%) | 2 (1.2%) |
| Lack of Efficacy | 0 | 2 (2.4%) | 2 (1.2%) |
| Non-compliance with drug | 0 | 1 (1.2%) | 1 (0.6%) |
| Protocol deviation | 0 | 1 (1.2%) | 1 (0.6%) |
| Withdrawal by subject | 1 (1.2%) | 0 | 1 (0.6%) |
| Other | 1 (1.2%) | 1 (1.2%) | 2 (1.2%) |

Percentages calculated with the number of subjects in each group as denominator.

(vii) Sexual Functioning

Impairments in sexual functioning is a common side effect of antidepressant treatment and can be very upsetting to patients and their sexual partners. Major depression itself is associated with increased sexual dysfunction, and many of the pharmacological treatments are known to worsen sexual functioning even further. In a large survey of nearly 5000 patients in France, it was estimated that in untreated patients with MDD, the prevalence of sexual dysfunction was 65%. The prevalence of sexual dysfunction increased to 71% for patients treated with antidepressant therapy.

Sexual pleasure is an important component of hedonic tone. The brain reward circuitry is controlled by several areas: nucleus accumbens, ventral tegmental area and the amygdala. It is hypothesized that treatment with kappa opioid receptors may restore the normal homeostatic balance in patients with overactivation. Treatment with aticaprant could potentially improve symptoms of anhedonia. Other symptoms associated with the reward circuitry includes: sexual pleasure, lack of interest and lack of enjoyment.

Patients had their sexual functioning measured using a standard, well accepted rating scale: ASEX. See, Table 32.

TABLE 32

ASEX scores by treatment group

| | Placebo n = 84 | Aticaprant n = 85 |
|---|---|---|
| Baseline | 22.04 | 21.26 |
| Endpoint | 21.36 | 19.79 |
| Absolute Change | −0.68 | −1.47 |
| Relative % Change | −3.09% | −6.91% |

Figure 19:
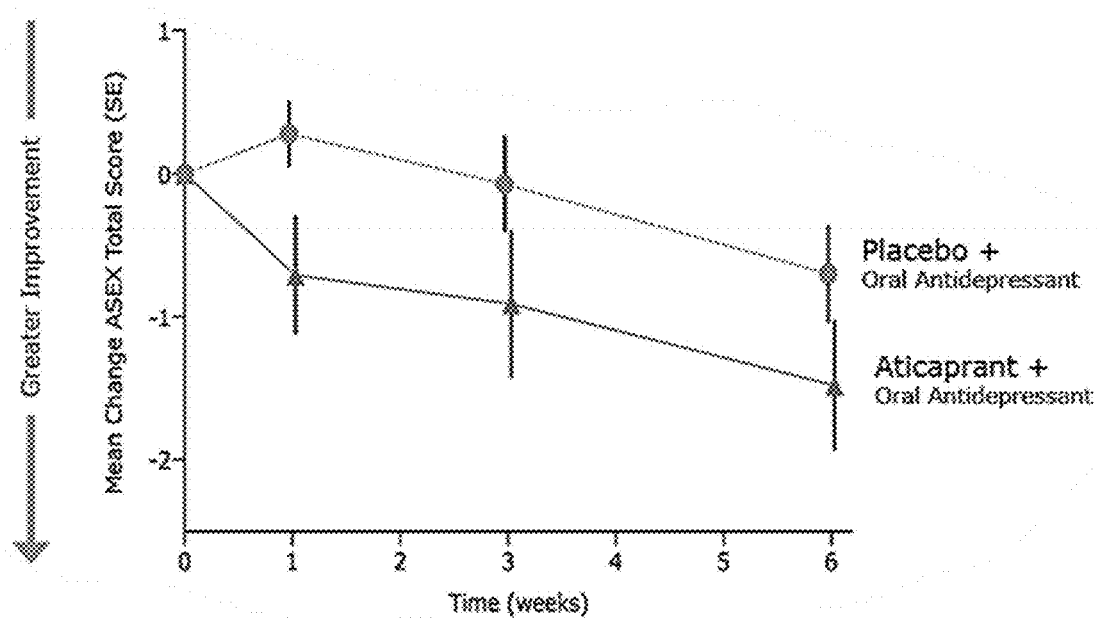
FIG. 19 is a line graph showing the ASEX total score mean change from baseline.

The mean change from treatment baseline (SD) in ASEX total score to week 6 was −1.5 (4.02) points for aticaprant compared to −0.7 (2.98) points for placebo. A lower score on the ASEX indicates improvement. The score reduction at week 6 was greater in the aticaprant group compared to placebo. This is unexpected because adjunctive treatments with other agents are expected to worsen sexual functioning, i.e., increase in ASEX score over time. See, FIG. 19.

Figure 20:
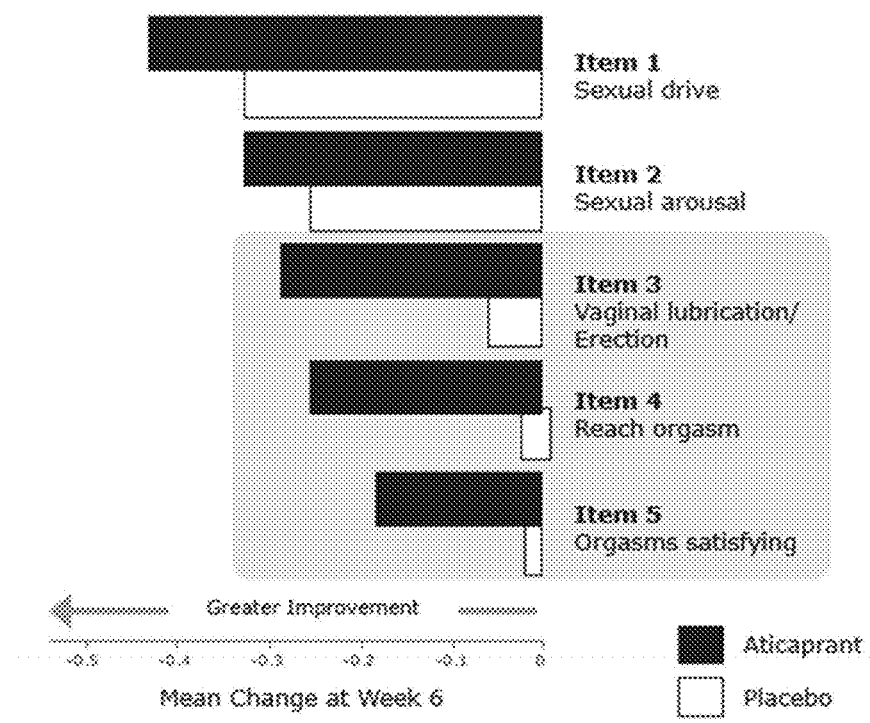
FIG. 20 is a bar graph showing ASEX item level change total score mean change from baseline.

Patients receiving aticaprant had notable improvements in sexual functioning. An examination of individual item level changes was also conducted and revealed that the greatest changes were seen in items related to consummatory pleasure: orgasm satisfying, reach orgasm and vaginal lubrication/erection. Most of the improvements seen in items 3, 4 and 5 of FIG. 20.

(viii) Onset of Effect

Figure 7B:
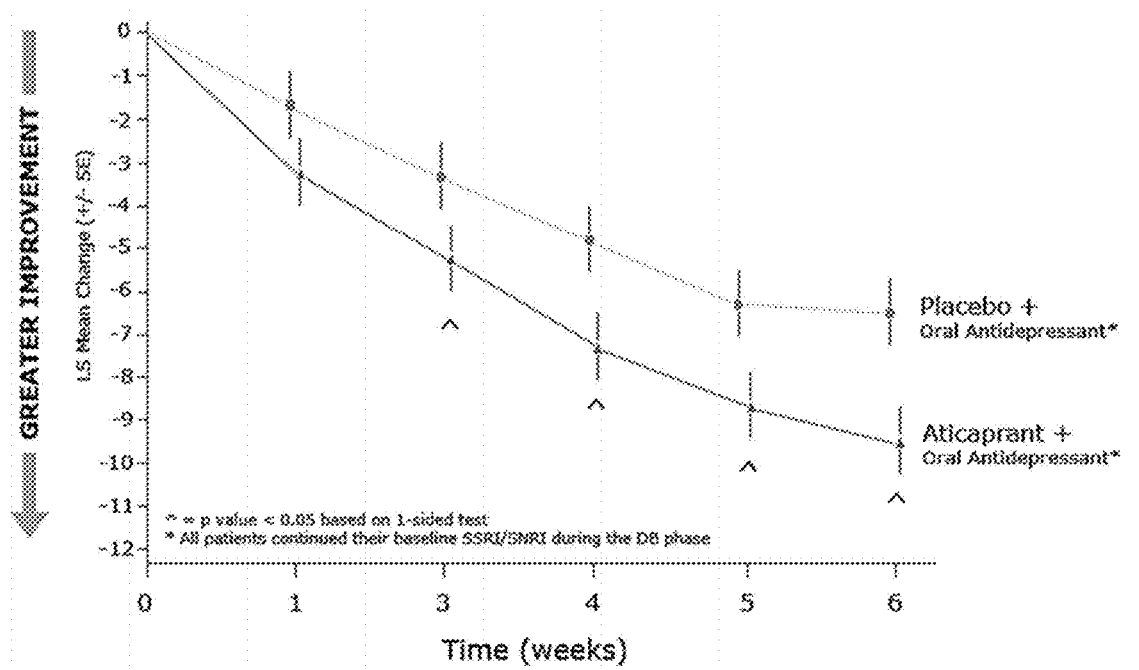
FIG. 7B is an excerpt from FIG. 7A for treatment weeks 0-6.

The onset of effect for aticaprant can be estimated from the study. FIG. 7B depicts the least squares mean change from baseline. A significant treatment effect favoring aticaprant was seen as early as week 3. At this point, aticaprant showed a statistically superior effect compared to placebo.

Example 2: Single Dose Aticaprant as Adjunctive Antidepressant Therapy

Figure 21:
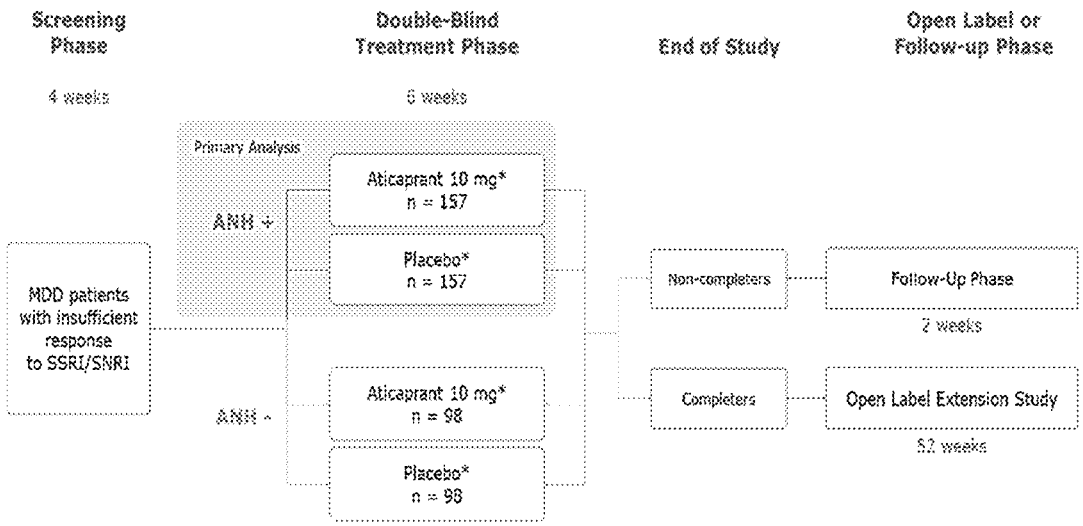
FIG. 21 is the study scheme for Example 2. All patients will continue their oral antidepressant SSRI/SNRI during the entire study. Approximately an additional 34 elderly participants will be randomized.

Study Design: A 6-week, multicenter, double-blind, randomized, placebo-controlled study to assess the efficacy, safety, and tolerability of aticaprant in adult and elderly subjects (18 to 74 years) who have MDD with prominent anhedonia (MDD ANH+), and who have had an inadequate response to a SSRI or a serotonin and SNRI in the current depressive episode. See, FIG. 21.

For all subjects, this study will consist of 3 phases: an eligibility screening phase (up to 4 weeks prior to first dose administration), a double-blind treatment phase of 6 weeks, and a follow-up of 1-2 weeks. Subjects who have completed the double-blind phase may participate in an open-label long-term safety study.

Sample Size and Randomization: Approximately 544 subjects with MDD with prominent anhedonia (MDD ANH+) and without prominent anhedonia (MDD ANH−) will be randomized in a 1:1 ratio to adjunctive placebo or aticaprant to achieve a minimum of 314 adult subjects meeting predefined criteria for MDD ANH+ eligible to be included in the primary analysis. Randomization will be stratified by study site, age group (adults [<65 years], elderly [≥65 years]), baseline anhedonia, and baseline MADRS total score. All subjects will continue their baseline antidepressant (SSRI/SNRI) during the entire study.

Doses and Administration All eligible subjects will receive aticaprant or placebo in addition to their baseline SSRI/SNRI which will be continued during the entire study. Study medication will be taken daily.

Inclusion Criteria:
1. Age of 18 to 74 years (inclusive).
2. Be medically stable on the basis of physical examination (including a brief neurological examination), medical history, vital signs (including blood pressure), and 12-lead ECG performed at screening and baseline. If there are any abnormalities that are not specified in the inclusion and exclusion criteria, their significance must be determined.
3. Be medically stable on the basis of clinical laboratory tests performed at screening. If the results of the serum chemistry panel, hematology, or urinalysis are outside the normal reference ranges, retesting of an abnormal lab values that may lead to exclusion will be allowed once during the screening phase.
4. Meet DSM-5 diagnostic criteria for recurrent or single episode MDD, without psychotic features (DSM-5 296.22, 296.23, 296.32, or 296.33), based upon clinical assessment and SCID-CT. Subjects 65 years of age or older must have had the first onset of depression prior to 55 years of age. The length of the current depressive episode must be ≤18 months.
5. Have had an inadequate response to at least 1 but no more than 2 antidepressants (SSRI/SNRI), administered at an adequate dose and duration in the current episode of depression. An inadequate response is defined as 26% to <50% reduction in depressive symptom severity and overall good tolerability, as assessed by the MGH-ATRQ. An adequate trial is defined as an antidepressant treatment for at least 6 weeks (and no greater than 12 months in the current episode) at or above the stable therapeutic dose specified in the MGH-ATRQ, must include the subject's current anti depressant treatment. If the subject has received 2 SSRI/SNRI treatments of sufficient dose and duration in the current episode, and has shown ≤25% improvement to both, then the subject would not qualify based on exclusion criterion (first exclusion criterion).

6. Current major depressive episode, depression symptom severity, presence of anhedonia and antidepressant treatment response in the current depressive episode must be confirmed. Is receiving and tolerating well any one of the following SSRI or SNRI for depressive symptoms, in any formulation and available in the participating country: citalopram, duloxetine, escitalopram, fluvoxamine, fluoxetine, milnacipran, levomilnacipran, paroxetine, sertraline, venlafaxine, desvenlafaxine at a stable dose (at therapeutic dose level) for at least 6 weeks, and for no greater than 12 months in the current episode, at screening. The above SSRI/SNRI needs to be approved for the treatment of MDD. Subjects using fluvoxamine as baseline SSRI and have normal renal and hepatic function are admitted.

7. HDRS-17 total score ≥22 at start of the screening and must not demonstrate a clinically significant improvement (which is defined as an improvement of <20% on their HDRS-17 total score) from the start to end of screening (from the first to the last independent HDRS-17 rating).

8. Symptoms of anhedonia based on clinical assessment and confirmed by a positive response for anhedonia (MDE symptoms Item 2) on the SCID-CT at screening and baseline (Day 1 prior to randomization).

9. BMI between 18 and 40 kg/m² (inclusive).

10. Outpatient at screening.

11. A woman of childbearing potential must have a negative highly sensitive serum (β-hCG) pregnancy test at screening and a negative urine pregnancy test predose on Day 1 of the double-blind phase prior to randomization.

12. Contraceptive use by men or women should be consistent with local regulations regarding the use of contraceptive methods for subjects in clinical studies.

13. A woman must be either:
    Postmenopausal
    Permanently sterile
    Of childbearing potential and practicing a highly effective method of contraception (failure rate of <1% per year when used consistently and correctly).

14. A woman must not to donate eggs (ova, oocytes) or freeze for future use for the purposes of assisted reproduction during the study and for a period of at least 1 month after receiving the last dose of study medication.

15. During the study and for a minimum of 1 spermatogenesis cycle (defined as approximately 3 months) after receiving the last dose of study medication, a man:
    who is sexually active with a woman of childbearing potential must use a barrier method of contraception (e.g., condom with spermicidal foam/gel/film/cream/suppository) and his female partner must use a highly effective method of contraception.
    who is sexually active with a woman who is pregnant must use a condom.
    must not to donate sperm.

Exclusion Criteria:
1. History of treatment-resistant MDD, defined as a lack of response to 2 or more adequate antidepressant treatments in the current episode, as indicated by no or minimal improvement (≤25% improvement) when treated with an antidepressant of adequate dose (per MGH-ATRQ) and duration (at least 6 weeks).

2. Current or prior DSM-5 diagnosis of a psychotic disorder or MDD with psychotic features, bipolar or related disorders (confirmed by the SCID-CT), intellectual disability (DSM-5 diagnostic codes 317, 318.0, 318.1, 318.2, 315.8, and 319), autism spectrum disorder, borderline personality disorder, antisocial personality disorder, histrionic personality disorder, narcissistic personality disorders or somatoform disorders.

3. Current active DSM-5 diagnosis of obsessive-compulsive disorder, post-traumatic stress disorder, anorexia nervosa, or bulimia nervosa.

4. Primary DSM-5 diagnosis of panic disorder, generalized anxiety disorder, social anxiety disorder, or specific phobia which has been the primary focus of psychiatric treatment within the past 2 years. These are allowed as secondary diagnoses if MDD is the primary focus of treatment.

5. History or evidence of clinically meaningful noncompliance with current antidepressant therapy.

6. History of moderate to severe substance use disorder including alcohol use disorder according to DSM-5 criteria within 6 months before screening or positive test results for alcohol and/or drugs of abuse (e.g., opiates [including methadone], cocaine, amphetamines, methamphetamines, cannabinoids, CBD, barbiturates, MDMA) at screening or at baseline. One retest during screening is allowed. Tobacco and caffeine use are not exclusionary.

7. Has within the last 5 years received any prior anti depressant treatment with ketamine/esketamine, electroconvulsive therapy, vagal nerve stimulation, or a deep brain stimulation device. Subjects who previously had taken up to 2 doses of ketamine/esketamine and did not continue (e.g., did not benefit from the treatment or experienced tolerability issues) can be considered for enrollment.

8. Homicidal ideation/intent or has suicidal ideation with some intent to act within 3 months prior to the start of the screening phase, per clinical judgment or based on the C-SSRS, corresponding to a response of "Yes" on Item 4 (active suicidal ideation with some intent to act, without specific plan) or Item 5 (active suicidal ideation with specific plan and intent) for suicidal ideation on the C-SSRS, or a history of suicidal behavior within the past year prior to the start of the screening phase. Subjects reporting suicidal ideation with intent to act or suicidal behavior prior to the start of the double-blind treatment phase should be excluded.

9. Cognitive impairment that would render the informed consent invalid or limit the ability of the subject to comply with the study requirements. Subject has neurodegenerative disorder (e.g., Alzheimer's disease, vascular dementia, Parkinson's disease with clinical evidence of cognitive impairment) or evidence of MCI. Subjects of age ≥65 years: has a MMSE <25 or <23 for those subjects with less than high school equivalent education.

10. Current or history of seizures (uncomplicated childhood febrile seizures with no sequelae are not exclusionary).

11. Clinically significant ECG abnormalities at screening or Day 1 prior to randomization that may jeopardize the subjects' safety or the integrity of the study defined as:

During screening and/or Day 1, a QT interval corrected according to Fridericia's formula (QTcF): ≥450 msec (males); ≥470 msec (females).

Evidence of second- and third-degree atrioventricular block.

Features of new ischemia.

Other clinically important arrhythmia or cardiac abnormalities.

12. History of, or symptoms and signs suggestive of, liver cirrhosis (e.g., esophageal varices, ascites, and increased prothrombin time) OR ALT or AST values≥3×the ULN or total bilirubin<1.5×the ULN in the screening phase. Repeat of screening test for abnormal ALT and AST is permitted during the screening period there is an alternative explanation for the out of range value.
13. For elevations in bilirubin if the elevation in bilirubin is consistent with Gilbert's disease, the subject may participate.
14. Positive test result for drugs of abuse (e.g., barbiturates, methadone, opiates, cocaine, PCP, MDMA, and amphetamine/methamphetamine) at the start of the screening phase or Day 1 of the double-blind treatment phase prior to randomization.
15. Subjects who have a positive test result at screening due to prescribed psychostimulants taken for any indication must discontinue the medication at least 2 weeks before Day 1 of the double-blind treatment phase (prior to randomization). The result of the Day 1 (prior to randomization) test for drugs of abuse must be negative for the subject to be randomized. Subjects who have a positive test result at screening due to prescribed/over-the-counter opiates or barbiturates may be permitted to continue in the screening phase if the medication is discontinued at least 1 week or 5 half-lives, whichever is longer, before Day 1 of the double-blind treatment phase (prior to randomization). The result of the Day 1 (prior to randomization) test for drugs of abuse must be negative for the subject to be randomized.

Intermittent use of cannabinoids prior to the start of the screening phase is not exclusionary as long as the subject does not meet the criteria for substance use disorder.

A positive test for cannabinoids at the start of the screening phase is not exclusionary; however, a positive test result for cannabinoids predose on Day 1 of the double-blind treatment phase is exclusionary.

16. Taking a total daily dose of benzodiazepines greater than the equivalent of 6 mg/day of lorazepam at the start of the screening phase.
17. Recent (last 3 months) history of, or current signs and symptoms of:

Severe renal insufficiency (creatinine clearance <30 mL/min)

Clinically significant or unstable cardiovascular, respiratory, gastrointestinal, neurologic, hematologic, rheumatologic, immunologic or endocrine disorders.

Uncontrolled Type 1 or Type 2 diabetes mellitus. Subjects with Type 1 or Type 2 diabetes mellitus who are controlled (hemoglobin A1c ≤8.0% and glucose ≤150 mg/dL at screening) may be eligible to participate if otherwise medically healthy, and if on a stable regimen of glucose-lowering medications for at least 2 months prior to screening).

18. Current signs/symptoms of hypothyroidism or hyperthyroidism. For subjects with a history of thyroid disease and for subjects who, regardless of thyroid history have the TSH value out of range, a $FT_4$ test will be conducted. If the FT4 value is abnormal and considered to be clinically significant the subject is not eligible.
19. Subjects with a pre-existing history of thyroid disease/disorder who are treated with thyroid hormones need to be on a stable dosage for 3 months prior to the start of the screening phase. Subjects taking thyroid supplementation for antidepressant purposes are not allowed. Has Cushing's Disease, Addison's Disease, primary amenorrhea, or other evidence of significant medical disorders of the hypothalamic-pituitary-adrenal axis.
20. Significant medical illness, particularly unstable medical problem.
21. Ongoing psychological treatments (e.g., Cognitive Behavior Therapy, Interpersonal Psychotherapy, Psychodynamic Psychotherapy etc.), initiated within 6 weeks prior to start of screening. A subject who has been receiving ongoing psychological treatment for a period of greater than 6 weeks is eligible, if psychological treatment to be of stable duration and frequency.
22. Significant medical illness, particularly unstable medical problem.
23. Clinically-relevant GI complaints per clinical judgment (unless symptoms of Axis I disorder) at screening or baseline or history of documented gastric disease (including but not limited to documented peptic ulcer disease, gastritis [including atrophic gastritis], upper GI bleeding, Barret's esophagus, Crohn disease, ulcerative colitis, GI precancerous conditions or any other clinically-relevant GI disease irritable bowel syndrome).
24. Requires chronic use of a PPIs. A history of chronic NSAID or aspirin use. (Low dose aspirin e.g., in cardiovascular disease prevention is allowed).
25. History of malignancy within 5 years before the start of the screening phase (exceptions are squamous and basal cell carcinomas of the skin and carcinoma in situ of the cervix, or malignancy that is considered cured with minimal risk of recurrence).
26. Known allergies, hypersensitivity, intolerance, or contraindications to aticaprant and/or its excipients.
27. Taken any prohibited therapies that would not permit dosing on Day 1.
28. Received an investigational drug (including investigational vaccines) or used an invasive investigational medical device within 60 days before the start of the screening phase, or has participated in 2 or more MDD or other psychiatric condition clinical interventional studies (with different investigational medication) in the previous 1 year before the start of the screening phase, or is currently enrolled in an investigational interventional study.
29. A woman who is pregnant, breastfeeding, or planning to become pregnant while enrolled or within 6 weeks after the last dose of the study medication.
30. Plans to father a child while enrolled or within 90 days after the last dose of study intervention.
31. Diagnosis of acquired immunodeficiency syndrome. Human immunodeficiency virus testing is not required.
32. Any condition or situation/circumstance for which participation would not be in the best interest of the subject (e.g., compromise the well-being) or that could prevent, limit, or confound the protocol specified assessments.

A. Efficacy Objectives and Endpoints

The assessment of primary and secondary (key and other) endpoints will be conducted on the FAS which includes adult (not elderly) subjects with MDD ANH+ who took at least 1 dose of study medication.

Primary: To evaluate the efficacy of aticaprant compared with placebo as adjunctive therapy to an antidepressant (SSRI or SNRI) in improving depressive symptoms in adult subjects with MDD ANH+ and inadequate response to the current antidepressant, as assessed by the change from baseline in the MADRS total score from Day 1 (pre-randomization) to end of the 6-week double-blind treatment phase (Day 43):

Change from baseline to Day 43 in the MADRS total score.

Key Secondary: To assess efficacy of aticaprant compared with placebo in adult subjects with MDD ANH+ as adjunctive therapy to an antidepressant on patient-reported assessment of anhedonia outcomes:

Change from baseline to Day 43 in the Dimensional Anhedonia Rating Scale (DARS) total score.

Other Secondary: To assess the efficacy of aticaprant compared with placebo in adult subjects with MDD ANH+ as adjunctive therapy on the following:

Proportion of responders at Day 43 (≥50% reduction in MADRS total score).

Proportion of subjects with remission of depressive symptoms, defined as a MADRS total score≤12 at Day 43.

Change from baseline to Day 43 in MADRS 6

Change from baseline to Day 43 in PHQ-9 total score.

Change from baseline to Day 43 in SHAPS total score.

Change from baseline to Day 43 in symptoms of anxiety using the GAD-7.

Exploratory: To assess the efficacy of aticaprant compared with placebo in adult subjects with MDD ANH+, and all MDD subjects (adult and elderly subjects with MDD ANH+ and MDD ANH−) as adjunctive therapy on the following:

Change from baseline over time in the MADRS total score.

Change from baseline over time in MADRS anhedonia items factor score.

Change from baseline over time in patient-reported outcomes of anhedonia (SHAPS, DARS).

Change from baseline over time in PHQ-9 total score.

Change from baseline to Day 43 in health-related quality of life and health status, as assessed by the EQ-5D-5L questionnaire.

Change from baseline to Day 43 in the SDS total score.

Change from baseline over time in the CGI-S score.

Change from baseline over time in symptoms of anxiety using the GAD-7.

Change from baseline over time in depressive symptoms using the PGI-S.

Change from baseline to Day 43 in patient-reported sexual functioning using the ASEX.

To assess the efficacy of aticaprant compared with placebo in adult subjects with MDD ANH− as adjunctive therapy on the following:

Change from baseline over time in MADRS total score.

Change from baseline over time in DARS total score.

Safety Objectives (All): The following safety endpoints will be assessed separately for the adult and elderly subjects; the safety analysis set for each age group will include all randomized subjects who have received at least one dose of study medication:

AEs including AESI. An AE can be any unfavorable and unintended sign (including an abnormal finding), symptom, or disease temporally associated with the use of a medicinal (investigational or non-investigational) product, whether or not related to that medicinal (investigational or non-investigational) product. TEAEs were AEs with onset during the treatment phase that has worsened since baseline. The full safety analysis set included all enrolled subjects who received at least 1 dose of study medication in the treatment period.

Vital signs

ECG, Laboratory Values

Weight/BMI

Suicidality assessment using the C-SSRS

Withdrawal symptoms assessment using the PWC-20

B. Concomitant Therapies and Prohibited Therapies

Background therapy: All subjects will continue their baseline antidepressant (SSRI/SNRI) during the entire study. The following antidepressants are permitted: citalopram, duloxetine, escitalopram, fluvoxamine, fluoxetine, milnacipran, levomilnacipran, paroxetine, sertraline, venlafaxine, and desvenlafaxine. Subjects will only continue one of these allowed antidepressants at an adequate and tolerated dose (i.e., monotherapy) during the study. No changes in antidepressant or dose are permitted from screening until the end of the study.

Prohibited therapies: Subjects must not use the following medications or food supplements prior to or during the study, as indicated, except to treat an AE or breakthrough symptoms, preferably after the EOT visit:

MAOIs within 4 weeks before screening until the first follow-up visit.

Antipsychotic drugs from at least 14 days before Day 1 until the first follow-up visit.

Hypnotic drugs or food supplements (from at least 7 days prior to Day 1 until the first follow-up visit), including but not limited to benzodiazepines, non-benzodiazepine hypnotics (e.g., zolpidem, zopiclone, zaleplon, eszopiclone, suvorexant and ramelteon), sedating antihistamines including over-the-counter hypnotics (e.g., diphenhydramine, doxylamine, and hydroxyzine), and melatonin/agomelatine.

Subjects who were taking benzodiazepines and/or permitted non-benzodiazepine sleep medications during the screening phase can continue these medications (at dosages equal to or less than the equivalent of 6 mg/day of lorazepam) during the double-blind treatment phase. No dose increases beyond the equivalent of 6 mg/day of lorazepam, or new benzodiazepine medications are permitted during the double-blind treatment phase.

Non-SSRI/SNRT antidepressants (e.g., doxepin, trazodone, mirtazapine, bupropion, tricyclic antidepressants, agomelatine, and SAMe) from at least 7 days before Day 1 until the first follow-up visit.

Any form of new psychotherapy or change in current psychotherapy is prohibited during the screening and double-blind phase.

Opiates and mood stabilizers (e.g., lithium and anticonvulsants) from at least 7 days prior to Day 1 until the first follow-up visit.

Stimulants (e.g., dexamphetamine, methylphenidate, dexmethylphenidate), oral systemic steroids, and appetite suppressants (ephedrine), and isoxsuprine from at least 7 days before Day 1 until EOT.

Magnetic and electrical stimulation therapies: electroconvulsive therapy, vagal nerve stimulation, deep brain stimulations, TMS of any type, or DCS or electrical stimulation, from screening to End-of-Study visit. TMS or DCS or electrical stimulation use prior to screening is not exclusionary.

T3, thyroid hormone or other thyroid function supplementation prescribed for depression.

These medications are allowed when given to control pre-existing thyroid disease/disorder.

Ketamine or esketamine within 5 years prior to and during the study (up to 2 doses are allowed in lifetime prior to screening).

Psychedelics (e.g., psilocybin).

Memantine.

Other investigational drugs within 30 days prior to and during the study.

Figure 22:
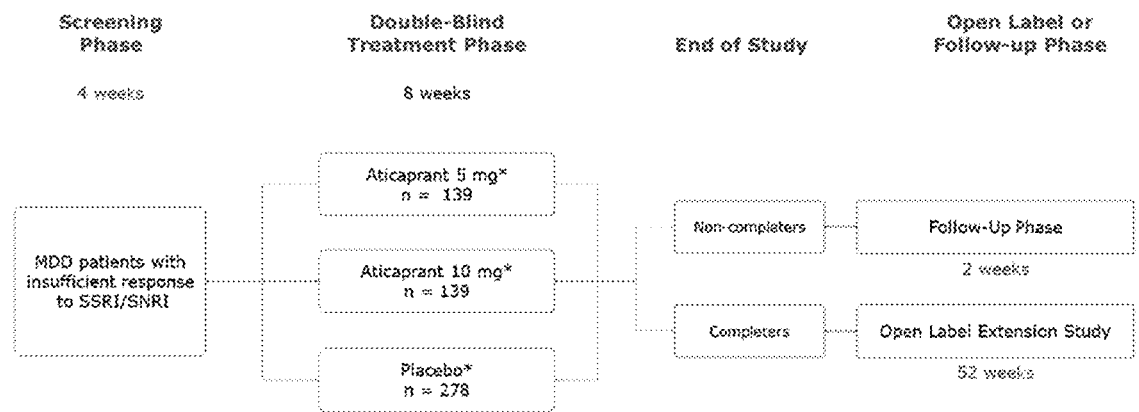
FIG. 22 is the study scheme for Example 3. All patients will continue their oral antidepressant SSRI/SNRT during the entire study. Approximately an additional 68 elderly participants will be randomized.

Example 3: A Randomized, Double-Blind, Multicenter, Placebo-Controlled Study to Evaluate the Efficacy, Safety, and Tolerability of Fixed Doses of Aticaprant 5 mg and 10 mg as Adjunctive Therapy in Adult and Elderly Subjects with MDD with Prominent Anhedonia and Inadequate Response to Current Antidepressant Therapy Study Design: An 8-week, multicenter, double-blind, randomized, placebo-controlled study to assess the efficacy, safety, and tolerability of aticaprant in adult and elderly subjects (18 to 74 years) who have MDD with prominent anhedonia and who have had an inadequate response to a SSRI or a SNRT in the current depressive episode. See, FIG. 22.

For all subjects, this study will consist of 3 phases:
an eligibility screening phase (up to 4 weeks prior to first dose administration),
a double-blind treatment phase of 8 weeks,
and a follow-up phase of 1-2 weeks.

Approximately 624 subjects (randomized in a 2:1:1 ratio to placebo, aticaprant 5 mg, and aticaprant 10 mg) will be enrolled in the study. This enrolment is targeted to achieve a minimum of 556 adult subjects with MDD with prominent anhedonia and approximately 68 elderly subjects (≥65 years) with MDD with prominent anhedonia.

Subjects who have completed the double-blind treatment phase may participate in an open-label long-term safety study.

Sample Size and Randomization: Approximately 624 adult (<65 years) and elderly (≥65 years) subjects with MDD with prominent anhedonia will be randomized in a 2:1:1 ratio to adjunctive placebo, 5-mg aticaprant, or 10-mg aticaprant to achieve a minimum of 556 adult subjects meeting predefined criteria for MDD with prominent anhedonia eligible to be included in the primary efficacy analysis set. Randomization will be stratified by study site, age group (adult, elderly) and baseline MADRS total score. All subjects will continue their baseline antidepressant (SSRI/SNRI) during the entire study.

Doses and Administration: All eligible subjects will receive aticaprant 5 mg, aticaprant 10 mg or placebo in addition to their baseline SSRI/SNRI which will be continued during the entire study. Study medication will be taken daily.

Inclusion Criteria:
1. Age of 18 to 74 years (inclusive).
2. Medically stable on the basis of physical examination (including a brief neurological examination), medical history, vital signs (including blood pressure), and 12-lead ECG performed at screen and baseline.
3. Medically stable on the basis of clinical laboratory tests performed at screening. If the results of the serum chemistry panel, hematology, or urinalysis are outside the normal reference ranges, retesting of an abnormal lab values that may lead to exclusion will be allowed once during the screening phase.
4. Meet DSM-5 diagnostic criteria for recurrent or single episode MDD, without psychotic features (DSM-5 296.22, 296.23, 296.32, or 296.33), based upon clinical assessment and confirmed by the SCID-CT. Subjects 65 years of age or older must have had the first onset of depression prior to 55 years of age. The length of the current depressive episode must be ≤18 months.
5. Symptoms of anhedonia based on clinical assessment and confirmed by a positive response for anhedonia (MDE symptoms Item 2) on the SCID-CT at screening and baseline (Day 1 prior to randomization).
6. SHAPS total score of ≥38 at screening and baseline (Day 1 prior to randomization) corresponding to prominent (high level) of anhedonia.
7. Inadequate response to at least 1 but no more than 2 antidepressants (SSRI/SNRI), administered at an adequate dose and duration in the current episode of depression. An inadequate response is defined as 26% to <50% reduction in depressive symptom severity and overall good tolerability, as assessed by the MGH-ATRQ. An adequate trial is defined as an antidepressant treatment for at least 6 weeks (and no greater than 12 months in the current episode) at or above the stable therapeutic dose specified in the MGH-ATRQ, must include the subject's current antidepressant treatment. If the subject has received 2 SSRI/SNRI treatments of sufficient dose and duration in the current episode, and has shown ≤25% improvement to both, then the subject would not qualify based on exclusion criterion (first exclusion criterion).
8. The current major depressive episode, depression symptom severity, presence of anhedonia and antidepressant treatment response in the current depressive episode, must be confirmed. Is receiving and tolerating well any one of the following SSRI or SNRI for depressive symptoms, in any formulation and available in the participating county citalopram, duloxetine, escitalopram, fluvoxamine, fluoxetine, milnacipran, levomilnacipran, paroxetine, sertraline, venlafaxine, desvenlafaxine at a stable dose (at therapeutic dose level) for at least 6 weeks, and for no greater than 12 months in the current episode, at screening. The SSRI/SNRI needs to be approved for the treatment of MDD.
9. HDRS-17 total score≥22 at start of the screening and must not demonstrate a clinically significant improvement (which is defined as an improvement of >20% on their HDRS-17 total score) from the start to end of screening (from the first to the last independent HDRS-17 rating).
10. BMI between 18 and 40 kg/m$^2$ (inclusive).
11. Outpatient at screening.
12. A woman of childbearing potential must have a negative highly sensitive serum (β human chorionic gonadotropin [β-hCG]) pregnancy test at screening and a negative urine pregnancy test predose on Day 1 of the double-blind phase prior to randomization.
13. Contraceptive use by men or women should be consistent with local regulations regarding the use of contraceptive methods for subjects in clinical studies.

14. A woman must be either:
   Postmenopausal: A postmenopausal state is defined as no menses for 12 months without an alternative medical cause. A high FSH level in the postmenopausal range based on the reference range of the central laboratory may be used to confirm a postmenopausal state in woman not using hormonal contraception or hormonal replacement therapy, however in the absence of 12 months of amenorrhea, a single FSH measurement is insufficient.
   Permanently sterile
   Of childbearing potential and practicing a highly effective method of contraception (failure rate of <1% per year when used consistently and correctly).
   Remains on a highly effective method and for at least 1 month after the last dose of study medication.
   A woman must not donate eggs (ova, oocytes) or freeze for future use for the purposes of assisted reproduction during the study and for a period of at least 1 month after receiving the last dose of study medication.
   During the study and for a minimum of 1 spermatogenesis cycle (defined as approximately 3 months) after receiving the last dose of study medication, a man (a) who is sexually active with a woman of childbearing potential must use a barrier method of contraception and his female partner must use a highly effective method of contraception; (b) who is sexually active with a woman who is pregnant must use a condom; (c) must not donate sperm.

Exclusion Criteria:
1. History of treatment-resistant MDD, defined as a lack of response to 2 or more adequate antidepressant treatments in the current episode, as indicated by no or minimal improvement (≤25% improvement) when treated with an antidepressant of adequate dose (per MGH-ATRQ) and duration (at least 6 weeks).
2. Current or prior DSM-5 diagnosis of a psychotic disorder or MDD with psychotic features, bipolar or related disorders (confirmed by the SCID-CT), intellectual disability (DSM-5 diagnostic codes 317, 318.0, 318.1, 318.2, 315.8, and 319), autism spectrum disorder, borderline personality disorder, antisocial personality disorder, histrionic personality disorder, narcissistic personality disorders or somatoform disorders.
3. Current active DSM-5 diagnosis of obsessive-compulsive disorder, post-traumatic stress disorder, anorexia nervosa, or bulimia nervosa.
4. Primary DSM-5 diagnosis of panic disorder, generalized anxiety disorder, social anxiety disorder, or specific phobia which has been the primary focus of psychiatric treatment within the past 2 years. These are allowed as secondary diagnoses if MDD is the primary focus of treatment.
5. History or evidence of clinically meaningful noncompliance with current antidepressant therapy.
6. History of moderate to severe substance use disorder including alcohol use disorder according to DSM-5 criteria within 6 months before screening or positive test results for alcohol and/or drugs of abuse (e.g., opiates [including methadone], cocaine, amphetamines, methamphetamines, cannabinoids, CBD, barbiturates, MDMA) at screening or at baseline. One retest during screening is allowed. Tobacco and caffeine use are not exclusionary.
7. Has within the last 5 years received any prior anti depressant treatment with ketamine/esketamine, electroconvulsive therapy, vagal nerve stimulation, or a deep brain stimulation device. Subjects who previously had taken up to 2 doses of ketamine/esketamine and did not continue (e.g., did not benefit from the treatment or experienced tolerability issues) can be considered for enrollment.
8. Homicidal ideation/intent or has suicidal ideation with some intent to act within 3 months prior to the start of the screening phase, per clinical judgment or based on the C-SSRS, corresponding to a response of "Yes" on Item 4 (active suicidal ideation with some intent to act, without specific plan) or Item 5 (active suicidal ideation with specific plan and intent) for suicidal ideation on the C-SSRS, or a history of suicidal behavior within the past year prior to the start of the screening phase. Subjects reporting suicidal ideation with intent to act or suicidal behavior prior to the start of the double-blind treatment phase should be excluded.
9. Cognitive impairment that would render the informed consent invalid or limit the ability of the subject to comply with the study requirements. Subject has neurodegenerative disorder (e.g., Alzheimer's disease, vascular dementia, Parkinson's disease with clinical evidence of cognitive impairment) or evidence of MCI. Subjects of age ≥65 years: has a MMSE <25 or <23 for those subjects with less than high school equivalent education.
10. Current or history of seizures (uncomplicated childhood febrile seizures with no sequelae are not exclusionary).
11. Clinically significant ECG abnormalities at screening or Day 1 prior to randomization that may jeopardize the subjects' safety or the integrity of the study defined as:
    During screening and/or Day 1, a QT interval corrected according to Fridericia's formula (QTcF): ≥450 msec (males); ≥470 msec (females).
    Evidence of second- and third-degree atrioventricular block.
    Features of new ischemia.
    Other clinically important arrhythmia or cardiac abnormalities.
12. History of, or symptoms and signs suggestive of, liver cirrhosis (e.g., esophageal varices, ascites, and increased prothrombin time) OR ALT or AST values≥3×the ULN or total bilirubin<1.5×the ULN in the screening phase. Repeat of screening test for abnormal ALT and AST is permitted during the screening period provided there is an alternative explanation for the out of range value.
13. For elevations in bilirubin if the elevation in bilirubin is consistent with Gilbert's disease, the subject may participate.
14. Positive test result for drugs of abuse (e.g., barbiturates, methadone, opiates, cocaine, PCP, MDMA, and amphetamine/methamphetamine) at the start of the screening phase or Day 1 of the double-blind treatment phase prior to randomization.
15. Subjects who have a positive test result at screening due to prescribed psychostimulants taken for any indication must discontinue the medication at least 2 weeks before Day 1 of the double-blind treatment phase (prior to randomization). The result of the Day 1 (prior to randomization) test for drugs of abuse must be negative for the subject to be randomized. Otherwise, subjects who have a positive test result at screening due to prescribed/over-the-counter opiates or barbiturates may be permitted to continue in the screening phase if the medication is discontinued at least 1 week or 5 half-lives, whichever is longer, before Day 1 of the double-blind treatment phase (prior to randomization). The result of the Day 1 (prior to randomization) test for drugs of abuse must be negative for the subject to be randomized.

16. Intermittent use of cannabinoids prior to the start of the screening phase is not exclusionary as long as the subject does not meet the criteria for substance use disorder. A positive test for cannabinoids at the start of the screening phase is not exclusionary; however, a positive test result for cannabinoids predose on Day 1 of the double-blind treatment phase is exclusionary.

17. Taking a total daily dose of benzodiazepines greater than the equivalent of 6 mg/day of lorazepam at the start of the screening phase.

18. Recent (last 3 months) history of, or current signs and symptoms of:
    Severe renal insufficiency (creatinine clearance <30 mL/min)
    Clinically significant or unstable cardiovascular, respiratory, gastrointestinal, neurologic, hematologic, rheumatologic, immunologic or endocrine disorders.
    Uncontrolled Type 1 or Type 2 diabetes mellitus. Subjects with Type 1 or Type 2 diabetes mellitus who are controlled (hemoglobin A1c ≤8.0% and glucose ≤150 mg/dL at screening) may be eligible to participate if otherwise medically healthy, and if on a stable regimen of glucose-lowering medications for at least 2 months prior to screening).

19. Current signs/symptoms of hypothyroidism or hyperthyroidism. For subjects with a history of thyroid disease and for subjects who, regardless of thyroid history have the TSH value out of range, a $FT_4$ test will be conducted. If the FT4 value is abnormal and considered to be clinically significant the subject is not eligible.

20. Subjects with a pre-existing history of thyroid disease/disorder who are treated with thyroid hormones need to be on a stable dosage for 3 months prior to the start of the screening phase. Subjects taking thyroid supplementation for antidepressant purposes are not allowed.

21. Cushing's Disease, Addison's Disease, primary amenorrhea, or other evidence of significant medical disorders of the hypothalamic-pituitary-adrenal axis.

22. Significant medical illness, particularly unstable medical problem

23. Ongoing psychological treatments (e.g., Cognitive Behavior Therapy, Interpersonal Psychotherapy, Psychodynamic Psychotherapy etc.), initiated within 6 weeks prior to start of screening. A subject who has been receiving ongoing psychological treatment for a period of greater than 6 weeks is eligible.

24. Significant medical illness, particularly unstable medical problem.

25. Clinically-relevant GI complaints (unless symptoms of Axis I disorder) at screening or baseline or history of gastric disease (including but not limited to documented peptic ulcer disease, gastritis [including atrophic gastritis], upper GI bleeding, Barret's esophagus, Crohn's disease, ulcerative colitis, GI precancerous conditions or any other clinically-relevant GI disease irritable bowel syndrome).

26. Requires chronic use of a PPIs. A history of chronic NSAID or aspirin use. (Low dose aspirin e.g., in cardiovascular disease prevention is allowed).

27. History of malignancy within 5 years before the start of the screening phase (exceptions are squamous and basal cell carcinomas of the skin and carcinoma in situ of the cervix, or malignancy that is considered cured with minimal risk of recurrence).

28. Known allergies, hypersensitivity, intolerance, or contraindications to aticaprant and/or its excipients.

29. Has taken any prohibited therapies that would not permit dosing on Day 1.

30. Taking a total daily dose of benzodiazepines greater than the equivalent of 6 mg/day of lorazepam at the start of the screening phase.

31. Received an investigational drug (including investigational vaccines) or used an invasive investigational medical device within 60 days before the start of the screening phase, or has participated in 2 or more MDD or other psychiatric condition clinical interventional studies (with different investigational medication) in the previous 1 year before the start of the screening phase, or is currently enrolled in an investigational interventional study.

32. A woman who is pregnant, breastfeeding, or planning to become pregnant while enrolled in this study or within 6 weeks after the last dose of the study medication.

33. Plans to father a child while enrolled in this study or within 90 days after the last dose of study intervention.

34. Diagnosis of acquired immunodeficiency syndrome. Human immunodeficiency virus testing is not required for this study.

35. Any condition or situation/circumstance for which participation would not be in the best interest of the subject (e.g., compromise the well-being) or that could prevent, limit, or confound the protocol specified assessments.

A. Efficacy Objectives and Endpoints

The assessment of primary and secondary (key and other) endpoints will be conducted on the full analysis set (FAS) which includes adult (not elderly) subjects with MDD with prominent anhedonia who took at least 1 dose of study medication.

Primary: Evaluate the efficacy of 2 fixed doses of aticaprant (5 mg and 10 mg) compared with placebo as adjunctive therapy to an antidepressant (SSRI or SNRI) in improving depressive symptoms in adult subjects (18-64 years) with MDD with prominent anhedonia and inadequate response to the current antidepressant
    Change from baseline to Day 43 in the MADRS total score.

Key Secondary: To assess efficacy of aticaprant 10 mg compared with placebo in adult subjects with MDD with prominent anhedonia as adjunctive therapy to an antidepressant on patient-reported assessment of anhedonia outcomes:
    Change from baseline to Day 43 in the Dimensional Anhedonia Rating Scale (DARS) total score.

Other Secondary: Assess the efficacy of aticaprant compared with placebo as adjunctive therapy to an antidepressant (SSRI or SNRI) in adult subjects with MDD with prominent anhedonia:
    Proportion of responders at Day 43 and Day 57 (≥50% reduction in MADRS total score).
    Proportion of subjects with remission of depressive symptoms, defined as a MADRS total score≤12 at Day 43 and Day 57.
    Change from baseline to Day 43 and Day 57 in MADRS-6
    Change from baseline to Day 43 and Day 57 in Patient Health Questionnaire, 9-Item (PHQ-9) total score.

Exploratory: To assess the efficacy of aticaprant compared with placebo in adult subjects with MDD with prominent anhedonia as adjunctive therapy on the following:

Change from baseline over time in the MADRS total score.

Change from baseline over time in MADRS anhedonia items factor score.

Change from baseline over time in patient-reported outcomes of anhedonia (SHAPS, DARS).

Change from baseline over time in PHQ-9 total score.

Change from baseline to Day 43 in health-related quality of life and health status, as assessed by the EQ-5D-5L questionnaire.

Change from baseline to Day 43 in the Sheehan Disability Scale (SDS) total score.

Change from baseline over time in the CGI-S score.

Change from baseline over time in symptoms of anxiety using the GAD-7.

Change from baseline over time in depressive symptoms using the PGI-S.

Change from baseline to Day 43 in patient-reported sexual functioning using the ASEX.

Safety Objectives (All): The following safety endpoints will be assessed separately for the adult and elderly subjects; the safety analysis set for each age group will include all randomized subjects who have received at least one dose of study medication:

AEs including AESI

Vital signs

ECG

Laboratory Values

Weight/BMI

Suicidality assessment using the C-SSRS

Withdrawal symptoms assessment using the PWC-20

Other Objectives (Exploratory):

To identify diagnostic biomarkers and to investigate changes in MDD-related biomarkers in relation to clinical response on depression symptoms and anhedonia upon monotherapy with aticaprant.

To identify genetic and other factors that may influence the pharmacokinetics (PK), safety, or tolerability of aticaprant.

B. Concomitant Therapies and Prohibited Therapies

Background therapy: All subjects will continue their baseline antidepressant (SSRI/SNRI) during the entire study. The following antidepressants are permitted: citalopram, duloxetine, escitalopram, fluvoxamine, fluoxetine, milnacipran, levomilnacipran, paroxetine, sertraline, venlafaxine, and desvenlafaxine. Subjects will only continue one of these allowed antidepressants at an adequate and tolerated dose (i.e., monotherapy) during the study. No changes in antidepressant or dose are permitted from screening until the end of the study.

Prohibited Therapies:

Subjects must not use the following medications or food supplements prior to or during the study, as indicated, except to treat an AE or breakthrough symptoms, preferably after the EOT visit:

MAOIs within 4 weeks before screening until the first follow-up visit.

Antipsychotic drugs from at least 14 days before Day 1 until the first follow-up visit.

Hypnotic drugs or food supplements (from at least 7 days prior to Day 1 until the first follow-up visit), including but not limited to benzodiazepines, non-benzodiazepine hypnotics (e.g., zolpidem, zopiclone, zaleplon, eszopiclone, suvorexant and ramelteon), sedating antihistamines including over-the-counter hypnotics (e.g., diphenhydramine, doxylamine, and hydroxyzine), and melatonin. Subjects who were taking benzodiazepines and/or permitted non-benzodiazepine sleep medications during the screening phase can continue these medications (at dosages equal to or less than the equivalent of 6 mg/day of lorazepam) during the double-blind treatment phase. No dose increases beyond the equivalent of 6 mg/day of lorazepam, or new benzodiazepine medications are permitted during the double-blind treatment phase.

Non-SSRI/SNRI antidepressants (e.g., doxepin, trazodone, mirtazapine, bupropion, tricyclic antidepressants, agomelatine, and SAMe) from at least 7 days before Day 1 until the first follow-up visit.

Any form of new psychotherapy or change in current psychotherapy is prohibited during the screening and double-blind phase of this study.

Opiates and mood stabilizers (e.g., lithium and anticonvulsants) from at least 7 days prior to Day 1 until the first follow-up visit.

Stimulants (e.g., dexamphetamine, methylphenidate, dexmethylphenidate), oral systemic steroids, and appetite suppressants (ephedrine), and isoxsuprine from at least 7 days before Day 1 until EOT.

Magnetic and electrical stimulation therapies: electroconvulsive therapy, vagal nerve stimulation, deep brain stimulations, TMS of any type, or DCS or electrical stimulation, from screening to End-of-Study visit. TMS or DCS or electrical stimulation use prior to screening is not exclusionary.

T3, thyroid hormone or other thyroid function supplementation prescribed for depression. These medications are allowed when given to control pre-existing thyroid disease/disorder.

Ketamine or esketamine within 5 years prior to and during the study (up to 2 doses are allowed in lifetime prior to screening).

Psychedelics (e.g., psilocybin).

Memantine.

Other investigational drugs within 30 days prior to and during the study.

What is claimed is:

1. A method for treating major depressive disorder in a human patient having anhedonia, the method comprising administering to the patient in need thereof an effective amount of aticaprant, or a pharmaceutically acceptable salt thereof, wherein the patient had an inadequate response to other antidepressant therapy prior to treatment with the aticaprant, or a pharmaceutically acceptable salt thereof, wherein the effective amount of the aticaprant is less than about 60 mg.

2. The method of claim 1, wherein the other antidepressant therapy comprised one or more antidepressants.

3. The method of claim 2, wherein the one or more antidepressants comprised a selective serotonin reuptake inhibitor (SSRI), serotonin-norepinephrine reuptake inhibitor (SNRI), or a combination thereof.

4. The method of claim 1, further comprising treatment with an effective amount of one or more antidepressants.

5. The method of claim 4, wherein the one or more antidepressants is a selective serotonin reuptake inhibitor (SSRI), serotonin-norepinephrine reuptake inhibitor (SNRI), or a combination thereof.

6. The method of claim 1, wherein the aticaprant is S-aticaprant, or a pharmaceutically acceptable salt thereof.

7. The method of claim 1, wherein the effective amount of the aticaprant is about 5 to about 50 mg.

8. The method of claim 1, wherein the effective amount of the aticaprant is about 2 to about 15 mg.

9. The method of claim 1, wherein the effective amount of the aticaprant is about 5 to about 15 mg.

10. The method of claim 1, wherein the effective amount of aticaprant is about 5 to about 10 mg.

11. The method of claim 1, wherein the effective amount of aticaprant is about 5 mg.

12. The method of claim 1, wherein the aticaprant, or a pharmaceutically acceptable salt thereof, is administered orally.

13. The method of claim 1, wherein the aticaprant, or a pharmaceutically acceptable salt thereof, is administered once daily.

14. The method of claim 1, wherein the patient has mild anhedonia, moderate anhedonia, severe anhedonia, moderate to severe anhedonia, or prominent anhedonia.

15. The method of claim 1, wherein the patient has moderate or severe anhedonia.

16. The method of claim 2, further comprising treatment with an effective amount of one or more antidepressants.

17. The method of claim 16, wherein the one or more antidepressants is a selective serotonin reuptake inhibitor (SSRI), serotonin-norepinephrine reuptake inhibitor (SNRI), or a combination thereof.

18. The method of claim 17, wherein the patient has moderate or severe anhedonia.

19. The method of claim 18, wherein the effective amount of the aticaprant is about 5 to about 10 mg.

20. The method of claim 19, wherein the effective amount of the aticaprant is about 5 mg.

21. The method of claim 19, wherein the aticaprant, or a pharmaceutically acceptable salt thereof, is administered orally and once daily.

22. The method of claim 20, wherein the aticaprant, or a pharmaceutically acceptable salt thereof, is administered orally and once daily.

23. The method of claim 3, further comprising treatment with an effective amount of one or more antidepressants.

24. The method of claim 23, wherein the one or more antidepressants is a selective serotonin reuptake inhibitor (SSRI), serotonin-norepinephrine reuptake inhibitor (SNRI), or a combination thereof.

25. The method of claim 24, wherein the patient has moderate or severe anhedonia.

26. The method of claim 25, wherein the effective amount of the aticaprant is about 5 to about 10 mg.

27. The method of claim 26, wherein the effective amount of the aticaprant is about 5 mg.

28. The method of claim 26, wherein the aticaprant, or a pharmaceutically acceptable salt thereof, is administered orally and once daily.

29. The method of claim 27, wherein the aticaprant, or a pharmaceutically acceptable salt thereof, is administered orally and once daily.

* * * * *